(12) United States Patent
Sands

(10) Patent No.: US 7,875,622 B2
(45) Date of Patent: Jan. 25, 2011

(54) METHODS AND COMPOSITIONS FOR TREATING PULMONARY HYPERTENSION AND RELATED DISEASES AND DISORDERS

(75) Inventor: Arthur T. Sands, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 219 days.

(21) Appl. No.: 12/169,815

(22) Filed: Jul. 9, 2008

(65) Prior Publication Data

US 2009/0054308 A1 Feb. 26, 2009

Related U.S. Application Data

(60) Provisional application No. 60/949,040, filed on Jul. 11, 2007.

(51) Int. Cl.
*A61K 31/505* (2006.01)
(52) U.S. Cl. ..................................... 514/269
(58) Field of Classification Search ................... 514/269
See application file for complete search history.

(56) References Cited

U.S. PATENT DOCUMENTS

| 4,156,734 | A | 5/1979 | Stone |
|---|---|---|---|
| 7,553,840 | B2 | 6/2009 | Devasagayaraj |
| 7,709,493 | B2 | 5/2010 | Devasagayaraj |
| 7,723,345 | B2 | 5/2010 | Devasagayaraj |
| 2003/0130349 | A1 | 7/2003 | Lobl |
| 2003/0191118 | A1 | 10/2003 | Sircar |
| 2004/0142991 | A1 | 7/2004 | Nag |
| 2004/0158076 | A1 | 8/2004 | Jackson |
| 2004/0209897 | A1 | 10/2004 | Vernier |
| 2005/0276803 | A1 | 12/2005 | Chan |
| 2006/0154936 | A1 | 7/2006 | Lasky |
| 2009/0005381 | A1 | 1/2009 | Brown |
| 2009/0048280 | A1 | 2/2009 | Burgoon |
| 2009/0054308 | A1 | 2/2009 | Sands |

FOREIGN PATENT DOCUMENTS

| EP | 1097711 | 5/2001 |
|---|---|---|
| WO | WO 91/01724 | 2/1991 |
| WO | WO 2004/017993 | 3/2004 |
| WO | WO 2004/058762 | 7/2004 |
| WO | WO 2005/044780 | 5/2005 |
| WO | WO 2008/073928 | 6/2008 |

OTHER PUBLICATIONS

Driscoll, J.A. and Chakinala, M.M., *Expert Opin. Pharmacother.* 9(1):65-81 (2008).
Eddahibi, S. et al., *Circulation* 113(15):1857-1864 (2006).
Izikki, M. et al., *Am. J. Physiol. Lung Cell Mol. Physiol.* 293:L1045-L1052 (2007).
Liu, Q. et al., *J. Pharmacol. Exp. Ther.* 325(1):47-55 (2008).
MacLean, M.R., *Int. J. Clin. Pract.* 61(suppl. 156):27-31 (2007).
MacLean, M.R. and Dempsie, Y., *Curr. Opin. Pharmacol.* 9:1-6 (2009).
Morecroft, I. et al, *Hypertension* 49:232-236 (2007).
Olsson, K.M. and Hoeper, M.M., *Drug DiSc. Today* 00(00) (2008).
Shi, Z-C., et al., *J. Med. Chem.* 51(13):3684-3687 (2008).
International Search Report and Written Opinion for Corresponding International Application Publication WO2008/069471, dated Sep. 7, 2008.

*Primary Examiner*—Raymond J Henley, III
(74) *Attorney, Agent, or Firm*—Max Bachrach

(57) ABSTRACT

Methods of treating pulmonary hypertension are disclosed. Particular methods comprise the administration of a tryptophan hydroxylase inhibitor and at least one other active pharmaceutical ingredient to patient in need thereof. Pharmaceutical formulations are also disclosed.

16 Claims, 1 Drawing Sheet

Figure 1:
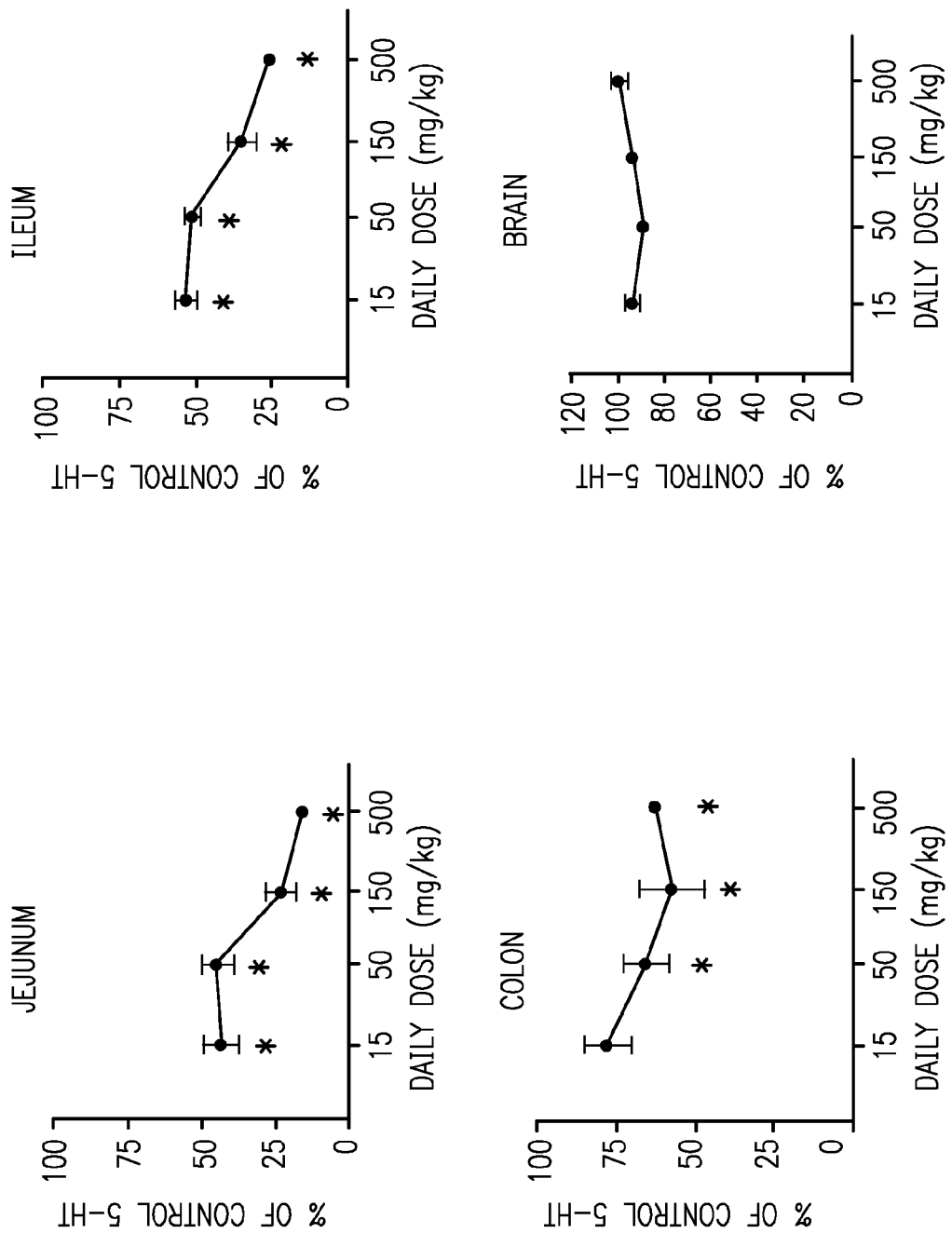

METHODS AND COMPOSITIONS FOR TREATING PULMONARY HYPERTENSION AND RELATED DISEASES AND DISORDERS

This application claims priority to U.S. provisional application No. 60/949,040, filed Jul. 11, 2007, the entirety of which is incorporated herein by reference.

1. FIELD OF THE INVENTION

This invention relates to methods and compositions for the treatment of pulmonary hypertension and related diseases and disorders.

2. BACKGROUND

Pulmonary hypertension (PH), or pulmonary arterial hypertension (PAH), is a disease characterized by increased pulmonary artery pressure and pulmonary vascular resistance. *Harrison's Principles of Internal Medicine*, 15th ed., pp. 1506-1507 (McGraw-Hill, 2001). Left untreated, PH "usually has a dismal prognosis culminating in right ventricular failure and death." Ulrich, S., et al., *Swiss Med. Wkly* 137:73-82, 73 (2007).

In 2003, the World Health Organization (WHO) sponsored the development of guidelines, called the "Venice classification," which are now used to classify types of PH. http://www.tracleer.com/default.asp?page=CouldHave_WHO (accessed Jun. 29, 2007). The first type, WHO Group 1.1, is idiopathic pulmonary arterial hypertension (IPAH). This refers to PAH that occurs at random, without an apparent cause. IPAH used to be called "primary pulmonary hypertension" or PPH. Id.

The second type, WHO Group 1.2, is familial pulmonary arterial hypertension (FPAH). With this type of PAH, a faulty gene is passed on through the family, which causes the PAH to develop over time. It is estimated that at least 6 to 10 percent of PAH cases occur in families where at least one other person has had the disease. Id.

The third type, WHO Group 1.3, is pulmonary arterial hypertension associated with other diseases or conditions (APAH). This used to be called "PAH secondary to other conditions" or Secondary PAH. This category includes PAH associated with collagen vascular disease or "connective tissue disease" (e.g., scleroderma (SSc)-including CREST syndrome-lupus (SLE)), congenital systemic-to-pulmonary shunts (congenital heart disease), portal hypertension, HIV infection, drugs and toxins, and other diseases and disorders (e.g., thyroid disorders, glycogen storage diseases, Gaucher disease, hereditary hemorrhagic telangiectasia, hemoglobinopathies, myeloproliferative disorders, splenectomy). Id.

The fourth type, WHO Group 1.4, is pulmonary arterial hypertension associated with significant venous or capillary involvement, and includes pulmonary veno-occlusive disease (PVOD) and pulmonary capillary hemangiomatosis (PCH).

The fifth and final type, WHO Group 1.5, is persistent pulmonary hypertension of the newborn. Id.

Drugs currently used to treat PH include pulmonary vasodilators, calcium channel blockers, and inhibitors of platelet aggregation. *The Merck Manual*, 17th ed., pp. 1703-4 (Merck Research Laboratories, 1999). Diuretics, nitric oxide, phosphodiesterase 5 inhibitors (e.g., sildenafil) and endothelin receptor antagonists (ERAs) are also used for its treatment. Ulrich, S., et al., *Swiss Med. Wkly* 137:73-82, 76-77 (2007). Endothelin receptor antagonists work by binding to the $ET_A$ and/or $ET_B$ receptor sites in the endothelium and vasculature smooth muscle, thereby preventing the neurohormone endothelin-1 (ET-1) from binding to these same receptor sites and triggering vasoconstriction. Id. at 76-77. An example of an ERA is bosentan (TRACLEER®).

Other methods of treating PH have been investigated. For example, selective serotonin reuptake inhibitors (SSRIs) reportedly reverse PH in rats. Id. at 79. These compounds, which are widely used to treat depression, affect the reuptake of the neurotransmitter serotonin (5-HT).

Serotonin is synthesized in two steps from the amino acid tryptophan. *Goodman & Gilman's The Pharmacological Basis of Therapeutics*, 10th ed., p. 270 (McGraw-Hill, 2001). The first step is rate-limiting, and is catalyzed by the enzyme tryptophan hydroxylase (TPH), which has two known isoforms: TPH1, which is expressed in the periphery, and TPH2, which is expressed primarily in the brain. Walther, D. J., et al., *Science* 299:76 (2003). Mice genetically deficient for the tph1 gene ("knockout mice") have been reported. In one case, the mice reportedly expressed normal amounts of serotonin in classical serotonergic brain regions, but largely lacked serotonin in the periphery. Id. In another, the knockout mice exhibited abnormal cardiac activity, which was attributed to a lack of peripheral serotonin. Côté, F., et al., *PNAS* 100(23): 13525-13530 (2003). Recently, TPH knockout mice were studied in a hypoxia-induced pulmonary arterial hypertension model. Morecroft, I., et al., Hypertension 49:232-236 (2007). The results of those studies suggest that TPH1 and peripheral serotonin "play an essential role in the development of hypoxia-induced elevations in pulmonary pressures and hypoxia-induced pulmonary vascular remodeling." Id. at 232.

3. SUMMARY OF THE INVENTION

This invention is directed, in part, to methods of treating pulmonary hypertension and related diseases and disorders, which comprise administering to a patient therapeutically effective amounts of a tryptophan hydroxylase (TPH) inhibitor and at least one other active pharmaceutical ingredient.

One embodiment encompasses a method of treating, managing or preventing pulmonary hypertension, which comprises administering to a patient in need thereof therapeutically or prophylactically effective amounts of an endothelin receptor antagonist and a tryptophan hydroxylase inhibitor.

Another encompasses a method of treating, managing or preventing pulmonary hypertension, which comprises administering to a patient in need thereof therapeutically or prophylactically effective amounts of an anticoagulant and a tryptophan hydroxylase inhibitor.

Another encompasses a method of treating, managing or preventing pulmonary hypertension, which comprises administering to a patient in need thereof therapeutically or prophylactically effective amounts of a calcium channel blocker and a tryptophan hydroxylase inhibitor.

Another encompasses a method of treating, managing or preventing pulmonary hypertension, which comprises administering to a patient in need thereof therapeutically or prophylactically effective amounts of a prostacyclin and a tryptophan hydroxylase inhibitor.

Another encompasses a method of treating, managing or preventing pulmonary hypertension, which comprises administering to a patient in need thereof therapeutically or prophylactically effective amounts of nitric oxide or a nitric oxide precursor or releasing compound, and a tryptophan hydroxylase inhibitor.

Another encompasses a method of treating, managing or preventing pulmonary hypertension, which comprises administering to a patient in need thereof therapeutically or prophylactically effective amounts of a phosphodiesterase 5 inhibitor and a tryptophan hydroxylase inhibitor.

Another encompasses a method of treating, managing or preventing pulmonary hypertension, which comprises administering to a patient in need thereof therapeutically or prophylactically effective amounts of a diuretic and a tryptophan hydroxylase inhibitor.

Another encompasses a method of treating, managing or preventing pulmonary hypertension, which comprises administering to a patient in need thereof therapeutically or prophylactically effective amounts of a platelet derived growth factor and a tryptophan hydroxylase inhibitor.

The invention also encompasses pharmaceutical formulations (e.g., single unit dosage forms) comprising a TPH inhibitor and at least one other active pharmaceutical ingredient.

4. BRIEF DESCRIPTION OF THE FIGURE

Aspects of the invention may be understood with reference to the attached FIGURE.

FIG. 1 shows the effects of a potent TPH1 inhibitor of the invention in the mouse gastrointestinal tract and brain after oral administration. All data are presented as percentage of the mean of the control (vehicle-dosed) group. Error bars are S.E.M. N=5 per group. The symbols are *, p<0.05 vs control group. For the brain data, p=0.5, one-way ANOVA.

5. DETAILED DESCRIPTION

This invention is based, in part, on studies of tph1 knockout mice and the discovery of compounds that inhibit tryptophan hydroxylase (e.g., TPH1).

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "biohydrolyzable amide," "biohydrolyzable ester," "biohydrolyzable carbamate," "biohydrolyzable carbonate," "biohydrolyzable ureido" and "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include lower alkyl esters, alkoxyacyloxy esters, alkyl acylamino alkyl esters, and choline esters. Examples of biohydrolyzable amides include lower alkyl amides, α-amino acid amides, alkoxyacyl amides, and alkylaminoalkyl-carbonyl amides. Examples of biohydrolyzable carbamates include lower alkylamines, substituted ethylenediamines, aminoacids, hydroxyalkylamines, heterocyclic and heteroaromatic amines, and polyether amines.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkylalkyl" refers to a heterocycloalkyl moiety bound to an alkyl moiety.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18$^{th}$ ed. (Mack Publishing, Easton Pa.: 1990) and *Remington: The Science and Practice of Pharmacy*, 19$^{th}$ ed. (Mack Publishing, Easton Pa.: 1995).

Unless otherwise indicated, the term "potent TPH1 inhibitor" is a compound that has a TPH1_IC$_{50}$ of less than about 10 μM.

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., *Design of Prodrugs*, Bundgaard, A. Ed., Elseview, 1985; Bundgaard, H., "Design and Application of Prodrugs," *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., *Protective Groups in Organic Synthesis* (3$^{rd}$ ed., John Wiley & Sons: 1999); Larock, R. C., *Comprehensive Organic Transformations* (2$^{nd}$ ed., John Wiley & Sons: 1999). Some examples include benzyl, diphenylmethyl, trityl, Cbz, Boc, Fmoc, methoxycarbonyl, ethoxycarbonyl, and pthalimido.

Unless otherwise indicated, the term "pseudohalogen" refers to a polyatomic anion that resembles a halide ion in its acid-base, substitution, and redox chemistry, generally has low basicity, and forms a free radical under atom transfer radical polymerization conditions. Examples of pseudohalogens include azide ions, cyanide, cyanate, thiocyanate, thiosulfate, sulfonates, and sulfonyl halides.

Unless otherwise indicated, the term "selective TPH1 inhibitor" is a compound that has a TPH2_IC$_{50}$ that is at least about 10 times greater than its TPH1_IC$_{50}$.

Unless otherwise indicated, the term "serotonin-mediated adverse effect" refers to an adverse effect that is attributable to increased levels of peripheral 5-hydroxytryptamine (5-HT).

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the term "TPH1_IC$_{50}$" is the IC$_{50}$ of a compound for TPH1 as determined using the in vitro inhibition assay described in the Examples, below.

Unless otherwise indicated, the term "TPH2_IC$_{50}$" is the IC$_{50}$ of a compound for TPH2 as determined using the in vitro inhibition assay described in the Examples, below.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

Unless otherwise indicated, the term "include" has the same meaning as "include" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. TPH Inhibitors

Particular embodiments of this invention utilize compounds capable of inhibiting tryptophan hydroxylase (TPH). Preferred compounds are potent TPH1 inhibitors. Examples of potent TPH1 inhibitors are disclosed in U.S. patent application Ser. No. 11/638,677, filed Dec. 12, 2006.

Particular embodiments utilize compounds of formula I:

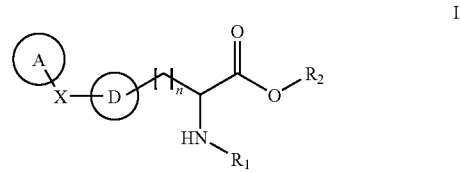

and pharmaceutically acceptable salts and solvates thereof, wherein: A is optionally substituted cycloalkyl, aryl, or heterocycle; X is a bond, —O—, —S—, —C(O)—, —C(R$_4$)═, ═C(R$_4$)—, —C(R$_3$R$_4$)—, —C(R$_4$)═C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; and n is 0-3.

Particular compounds are of formula I(A):

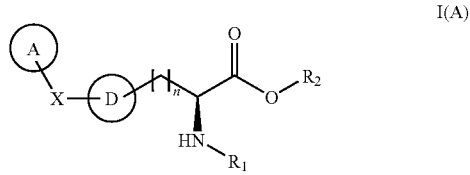

Others are of formula II:

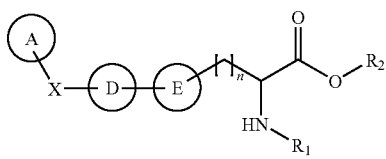

and pharmaceutically acceptable salts and solvates thereof, wherein: A is optionally substituted cycloalkyl, aryl, or heterocycle; X is a bond, —O—, —S—, —C(O)—, —C(R$_4$)═, ═C(R$_4$)—, —C(R$_3$R$_4$)—, —C(R$_4$)═C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R$_1$ is hydrogen or optionally substituted alkyl, alkyl-aryl, alkyl-heterocycle, aryl, or heterocycle; R$_2$ is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; R$_5$ is hydrogen or optionally substituted alkyl or aryl; and n is 0-3.

Particular compounds are of formula II(A):

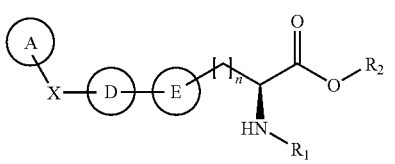

With regard to the formulae disclosed herein (e.g., I, I(A), II and II(A)), particular compounds include those wherein A is optionally substituted cycloalkyl (e.g., 6-membered and 5-membered). In some, A is optionally substituted aryl (e.g., phenyl or naphthyl). In others, A is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, A is aromatic. In others, A is not aromatic. In some, A is an optionally substituted bicyclic moiety (e.g., indole, iso-indole, pyrrolo-pyridine, or napthylene).

Particular compounds are of the formula:

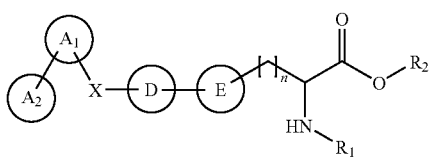

wherein: each of A$_1$ and A$_2$ is independently a monocyclic optionally substituted cycloalkyl, aryl, or heterocycle. Compounds encompassed by this formula include those wherein A$_1$ and/or A$_2$ is optionally substituted cycloalkyl (e.g., 6-membered and 5-membered). In some, A$_1$ and/or A$_2$ is optionally substituted aryl (e.g., phenyl or naphthyl). In others, A$_1$ and/or A$_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, A$_1$ and/or A$_2$ is aromatic. In others, A$_1$ and/or A$_2$ is not aromatic.

With regard to the formulae disclosed herein, particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

With regard to the various formulae disclosed herein, particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

With regard to the various formulae disclosed herein, particular compounds include those wherein R$_1$ is hydrogen or optionally substituted alkyl.

In some, R$_2$ is hydrogen or optionally substituted alkyl.

In some, n is 1 or 2.

In some, X is a bond or S. In others, X is —C(R$_4$)═, ═C(R$_4$)—, —C(R$_3$R$_4$)—, —C(R$_4$)═C(R$_4$)—, or —C≡C—, and, for example, R$_4$ is independently hydrogen or optionally substituted alkyl. In others, X is —O—, —C(R$_3$R$_4$)O—, or —OC(R$_3$R$_4$)—, and, for example, R$_3$ is hydrogen or optionally substituted alkyl, and R$_4$ is hydrogen or optionally substituted alkyl. In some, R$_3$ is hydrogen and R$_4$ is trifluoromethyl. In some compounds, X is —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—, and, for example, R$_3$ is hydrogen or optionally substituted alkyl, R$_4$ is hydrogen or optionally substituted alkyl, and R$_5$ is hydrogen or optionally substituted alkyl. In others, X is —N(R$_5$)—, —N(R$_5$)C(O)N(R$_5$)—, —C(R$_3$R$_4$)N(R$_5$)—, or —N(R$_5$)C(R$_3$R$_4$)—, and, for example, R$_3$ is hydrogen or optionally substituted alkyl, R$_4$ is hydrogen or optionally substituted alkyl, and each R$_5$ is independently hydrogen or optionally substituted alkyl.

Other compounds are of the formula:

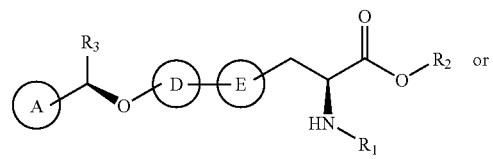

-continued

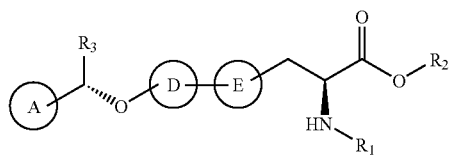

wherein, for example, $R_3$ is trifluoromethyl. Others are encompassed by the formula:

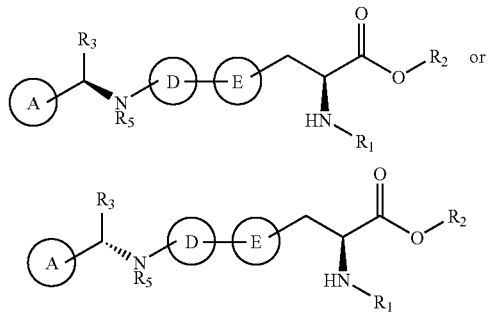

wherein, for example, $R_3$ is hydrogen.

Some compounds are encompassed by the formula:

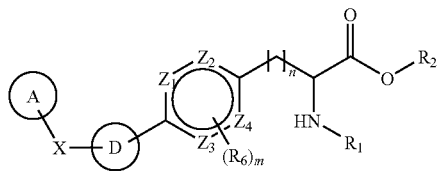

wherein: each of $Z_1$, $Z_2$, $Z_3$, and $Z_4$ is independently N or $CR_6$; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and m is 1-4. Certain such compounds are of the formula:

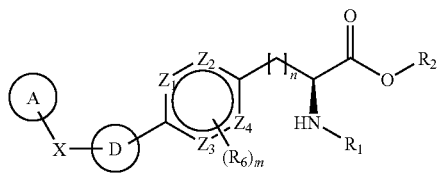

Others are of the formula:

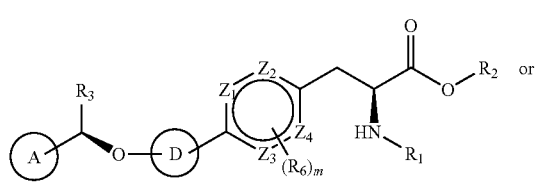

-continued

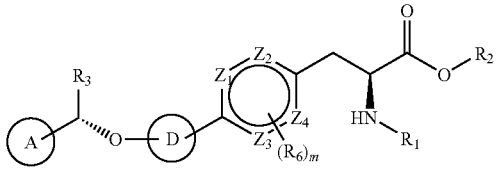

wherein, for example, $R_3$ is trifluoromethyl. Others are of the formula:

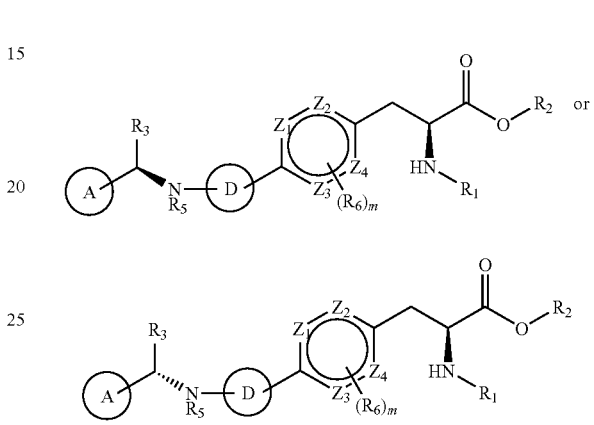

wherein, for example, $R_3$ is hydrogen.

Referring to the various formulae above, some compounds are such that all of $Z_1$, $Z_2$, $Z_3$, and $Z_4$ are N. In others, only three of $Z_1$, $Z_2$, $Z_3$, and $Z_4$ are N. In others, only two of $Z_1$, $Z_2$, $Z_3$, and $Z_4$ are N. In others, only one of $Z_1$, $Z_2$, $Z_3$, and $Z_4$ is N. In others, none of $Z_1$, $Z_2$, $Z_3$, and $Z_4$ are N.

Some compounds are of the formula:

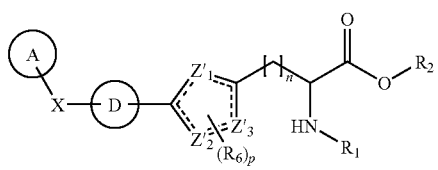

wherein: each of $Z'_1$, $Z'_2$, and $Z'_3$ is independently N, NH, S, O or $CR_6$; each $R_6$ is independently amino, cyano, halogen, hydrogen, $OR_7$, $SR_7$, $NR_8R_9$, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and p is 1-3. Certain such compounds are of the formula:

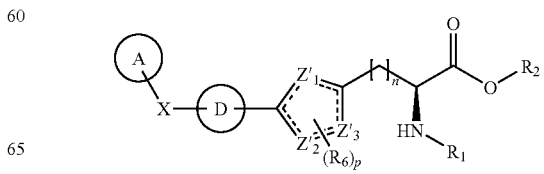

Others are of the formula:

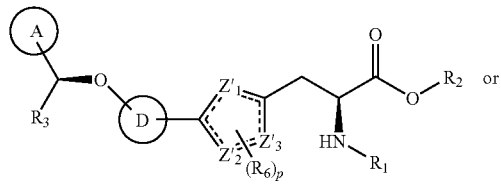

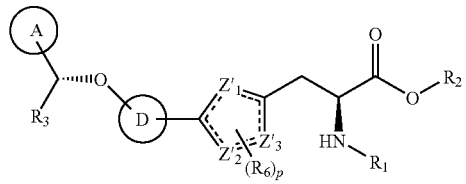

wherein, for example, $R_3$ is trifluoromethyl. Others are of the formula:

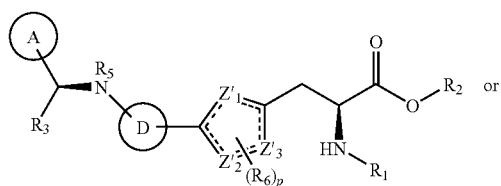

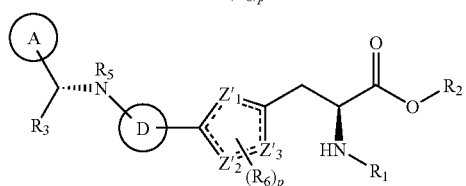

wherein, for example, $R_3$ is hydrogen.

Referring to the various formulae above, some compounds are such that all of $Z'_1$, $Z'_2$, and $Z'_3$ are N or NH. In others, only two of $Z'_1$, $Z'_2$, and $Z'_3$ are N or NH. In others, only one of $Z'_1$, $Z'_2$, and $Z'_3$ is N or NH. In others, none of $Z'_1$, $Z'_2$, and $Z'_3$ are N or NH.

Some compounds are encompassed by the formula:

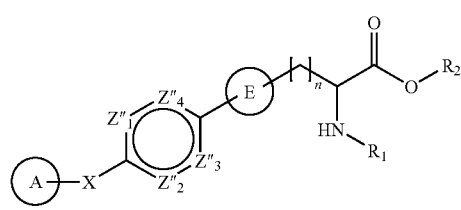

wherein: each of $Z''_1$, $Z''_2$, $Z''_3$, and $Z''_4$ is independently N or $CR_{10}$; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle. Certain such compounds are of the formula:

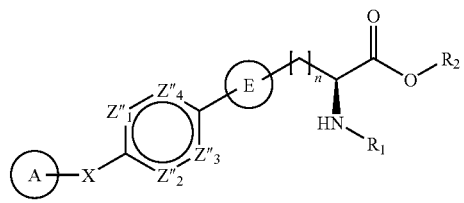

Others are of the formula:

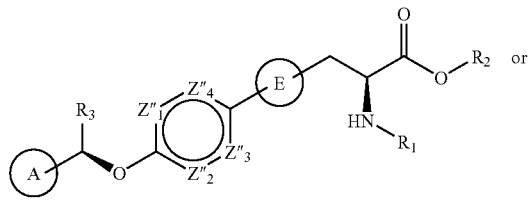

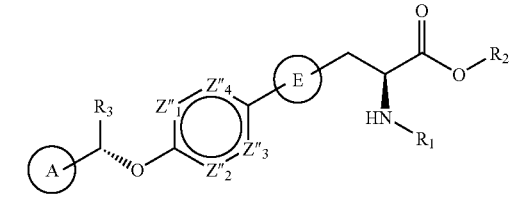

wherein, for example, $R_3$ is trifluoromethyl. Others are of the formula:

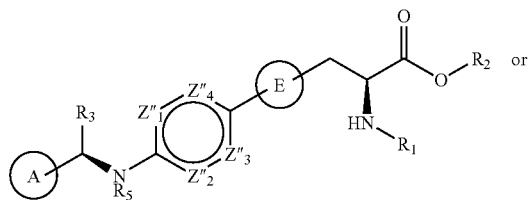

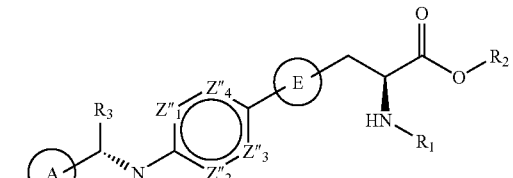

wherein, for example, $R_3$ is hydrogen.

Referring to the various formulae above, some compounds are such that all of $Z''_1$, $Z''_2$, $Z''_3$, and $Z''_4$ are N. In others, only three of $Z''_1$, $Z''_2$, $Z''_3$, and $Z''_4$ are N. In others, only two of $Z''_1$, $Z''_2$, $Z''_3$, and $Z''_4$ are N. In others, only one of $Z''_1$, $Z''_2$, $Z''_3$, and $Z''_4$ is N. In others, none of $Z''_1$, $Z''_2$, $Z''_3$, and $Z''_4$ are N.

Some compounds are of the formula:

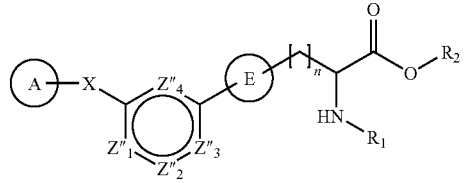

wherein: each of $Z''_1$, $Z''_2$, $Z''_3$, and $Z''_4$ is independently N or $CR_{10}$; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle. Certain such compounds are of the formula:

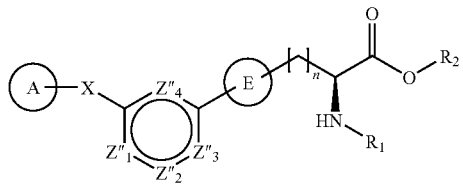

Others are of the formula:

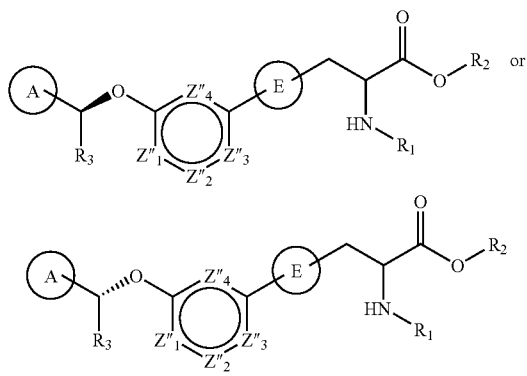

wherein, for example, $R_3$ is trifluoromethyl. Others are of the formula:

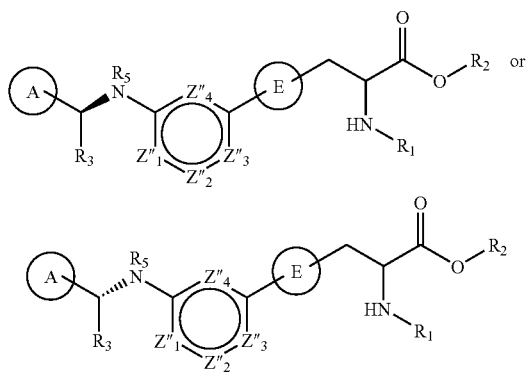

wherein, for example, $R_3$ is hydrogen.

Referring to the various formulae above, some compounds are such that all of $Z''_1$, $Z''_2$, $Z''_3$, and $Z''_4$ are N. In others, only three of $Z''_1$, $Z''_2$, $Z''_3$, and $Z''_4$ are N. In others, only two of $Z''_1$, $Z''_2$, $Z''_3$, and $Z''_4$ are N. In others, only one of $Z''_1$, $Z''_2$, $Z''_3$, and $Z''_4$ is N. In others, none of $Z''_1$, $Z''_2$, $Z''_3$, and $Z''_4$ are N.

Some are of the formula:

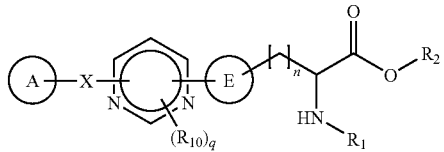

the substituents of which are defined herein. Others are of the formula:

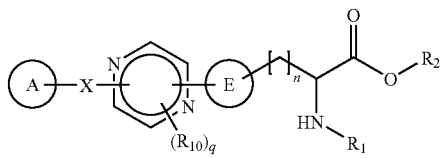

the substituents of which are defined herein. Others are of the formula:

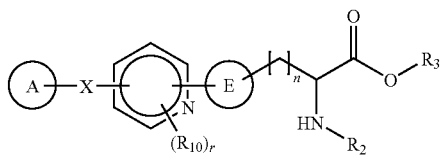

the substituents of which are defined herein. Others are of the formula:

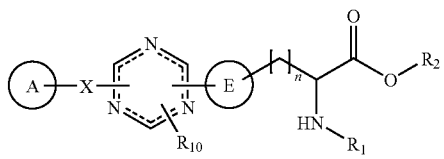

the substituents of which are defined herein.

Referring to the various formulae disclosed herein, particular compounds include those wherein both A and E are optionally substituted phenyl and, for example, X is —O—, —$C(R_3R_4)O$—, or —$OC(R_3R_4)$— and, for example, $R_3$ is hydrogen and $R_4$ is trifluoromethyl and, for example, n is 1.

This invention encompasses stereomerically pure compounds and stereomerically enriched compositions of them. Stereoisomers may be asymmetrically synthesized or resolved using standard techniques such as chiral columns, chiral resolving agents, or enzymatic resolution. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972).

Particular compounds of the invention are potent TPH1 inhibitors. Specific compounds have a TPH1_$IC_{50}$ of less than about 10, 5, 2.5, 1, 0.75, 0.5, 0.4, 0.3, 0.2, 0.1, or 0.05 μM.

Particular compounds are selective TPH1 inhibitors. Specific compounds have a TPH1_$IC_{50}$ that is about 10, 25, 50, 100, 250, 500, or 1000 times less than their TPH2_$IC_{50}$.

Particular compounds do not significantly inhibit human tyrosine hydroxylase (TH). For example, specific compounds have an $IC_{50}$ for TH of greater than about 100, 250, 500 or 1000 μm.

Particular compounds do not significantly inhibit human phenylalanine hydroxylase (PAH). For example, specific compounds have an $IC_{50}$ for PAH of greater than about 100, 250, 500 or 1000 μM.

Particular compounds of the invention do not significantly bind (e.g., inhibit with an $IC_{50}$ of greater than about 10, 25, 50, 100, 250, 500, 750, or 1000 μM) to one or more of the following: angiotensin converting enzyme, erythropoietin (EPO) receptor, factor IX, factor XI, integrin (e.g., α4), isoxazoline or isoxazole fibrinogen receptor, metalloprotease, neutral endopeptidase (NEP), phosphatase (e.g., tyrosine phosphatase), phosphodiesterase (e.g., PDE-4), polymerase, PPARγ, TNF-α, vascular cell adhesion molecule-1 (VCAM-1), or the vitronectin receptor. The ability of a compound to bind to (e.g., inhibit) any of these targets can be readily determined using methods known in the art, as described in references cited above. Specific compounds of the invention do not inhibit cell adhesion.

When administered to mammals (e.g., mice, rats, dogs, monkeys or humans), certain compounds of the invention do not readily cross the blood/brain barrier (e.g., less than about 5, 2.5, 2, 1.5, 1, 0.5, or 0.01 percent of compound in the blood passes into the brain). The ability or inability of a compound to cross the blood/brain barrier can be determined by methods known in the art. See, e.g., Riant, P. et al., *Journal of Neurochemistry* 51:421-425 (1988); Kastin, A. J., Akerstrom, V., *J. Pharmacol. Exp. Therapeutics* 294:633-636 (2000); W. A. Banks, W. A., et al., *J. Pharmacol. Exp. Therapeutics* 302: 1062-1069 (2002).

5.3. Synthesis of TPH Inhibitors

Compounds of the invention can be prepared by methods known in the art, and by methods described herein.

For example, with reference to formula I, compounds in which E is phenyl and D is optionally substituted pyrazine, pyridiazine, pyridine or phenyl can generally be prepared by the method shown in Scheme 1:

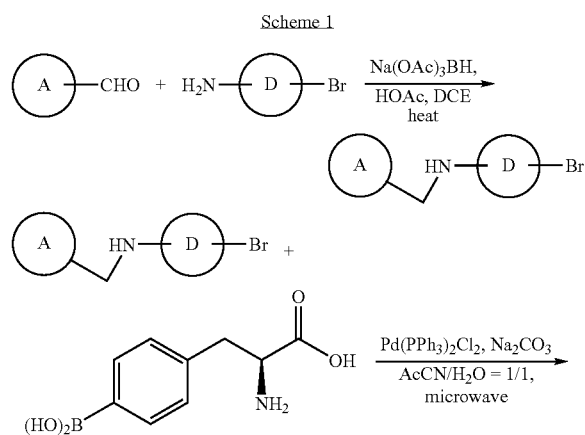

-continued

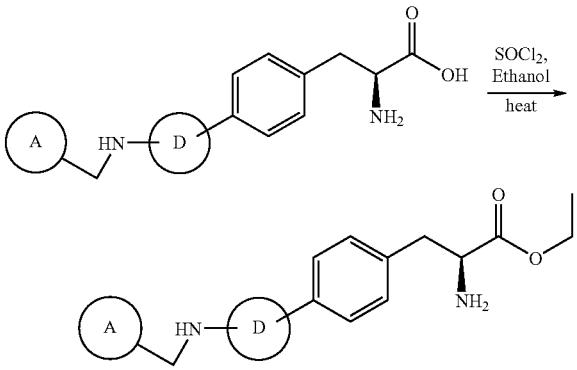

wherein, for example:

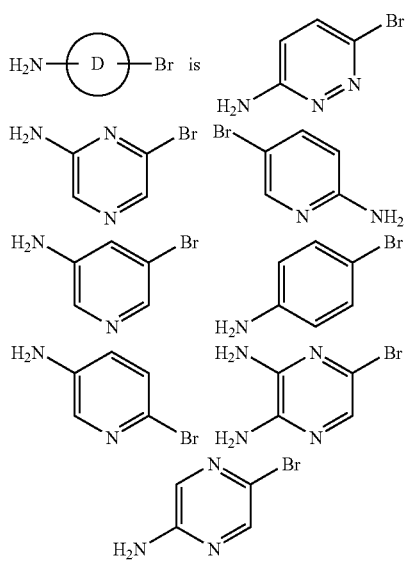

Compounds wherein X is —$OCR_3$— can generally be prepared using the method shown in Scheme 2, wherein $R_3$ is $CF_3$ and D is pyrimidine:

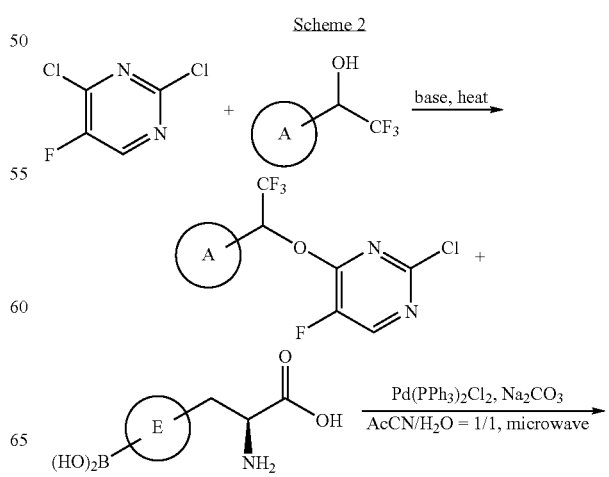

-continued

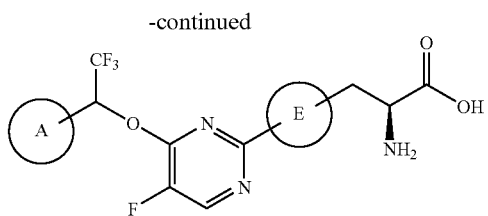

wherein, for example, A is optionally substituted phenyl, biphenyl or napthyl.

Compounds of the invention can also be prepared using the approach shown below in Scheme 3:

wherein $P_1$ is $R_1$ or a protecting group; $P_2$ is a protecting group; $P_3$ is $OR_2$ or a protecting group; X' is, for example, O or N; $Y_1$ and $Y_3$ are halogen (e.g., Br, Cl) or an appropriate pseudohalide (e.g., triflate); and each R' is independently hydrogen or optionally substituted alkyl, alkyl-aryl, alkyl-heterocycle, aryl, or heterocycle, or are taken together with the oxygen atoms to which they are attached to provide a cyclic dioxaborolane (e.g., 4,4,5,5-tetramethyl-1,3,2-dioxaborolane). The groups A, $R_1$, $R_2$, $R_3$, $R_6$ and m are defined elsewhere herein. The moieties $Z''_1$, $Z''_2$, $Z''_3$, and $Z''_4$ are also defined herein, although it is to be understood that with regard to the scheme shown above, one of them is attached to the phenyl ring. For example, $Z''_1$ and $Z''_4$ may be independently $CR_{10}$ (which is defined herein), while $Z''_2$ is N and $Z''_3$ is a carbon atom bound to the adjacent phenyl ring.

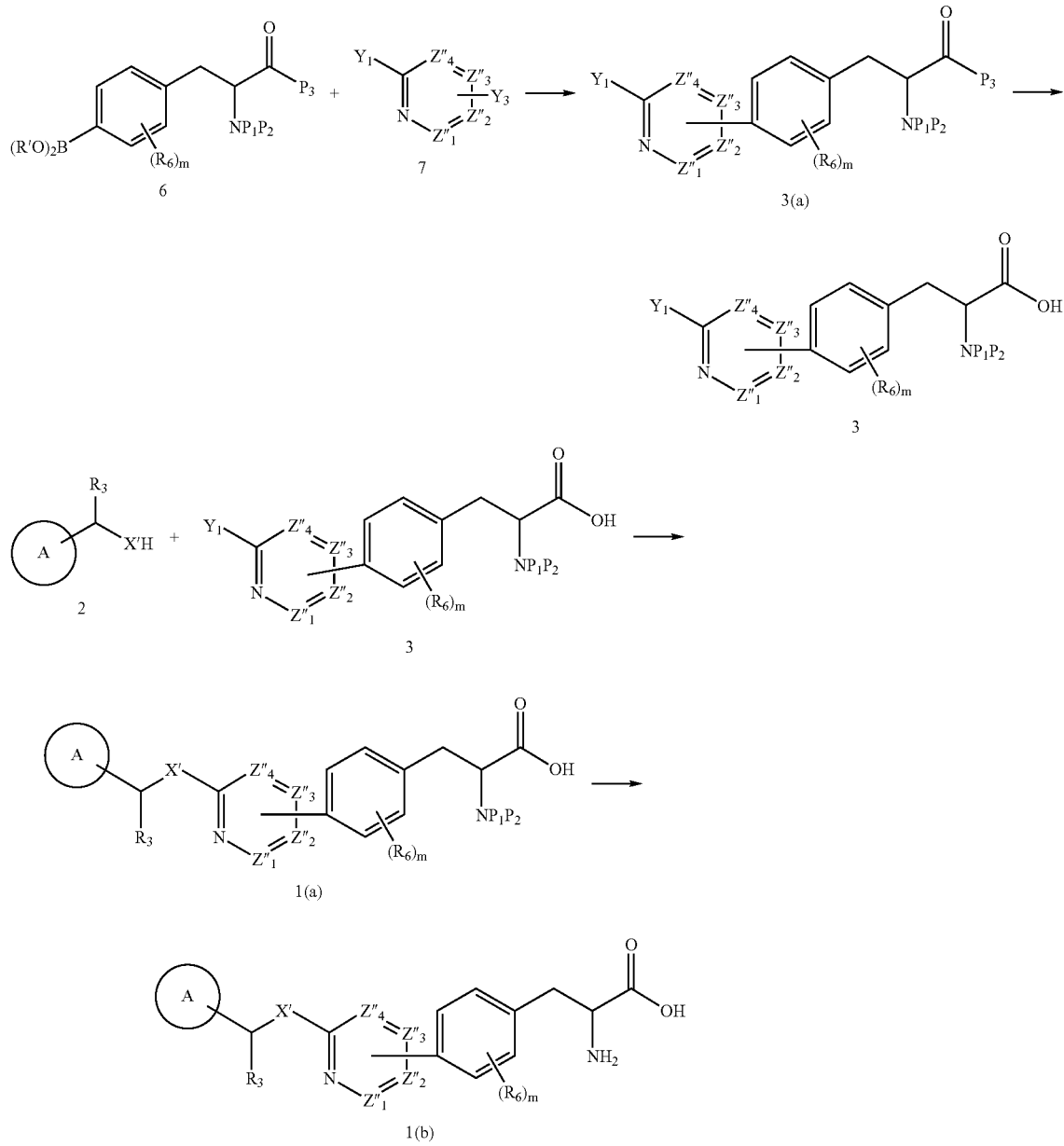

The individual reactions shown above can be performed using conditions known in the art. For example, palladium catalysts and conditions suitable for the Suzuki coupling of the boron and halogen-containing moieties are well known, and examples are provided below. In addition, types and appropriate uses of protecting groups are well known, as are methods of their removal and replacement with moieties such as, but not limited to, hydrogen (e.g., hydrolysis under acidic or basic conditions).

The A moiety can be bicyclic (e.g., optionally substituted biphenyl). In such cases, the starting material containing A can be prepared as shown below:

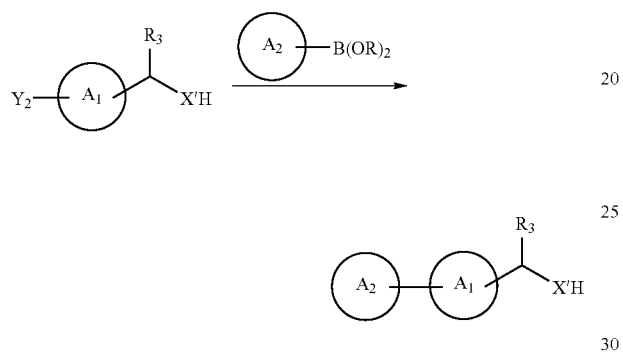

wherein $Y_2$ is halogen or pseudohalogen, and each R is independently hydrogen or optionally substituted alkyl, alkyl-aryl, alkyl-heterocycle, aryl, or heterocycle, or are taken together with the oxygen atoms to which they are attached to provide a cyclic dioxaborolane (e.g., 4,4,5,5-tetramethyl-1,3,2-dioxaborolane).

Another approach to the preparation of compounds wherein D is optionally substituted pyrimidine or triazine is shown below in Scheme 4:

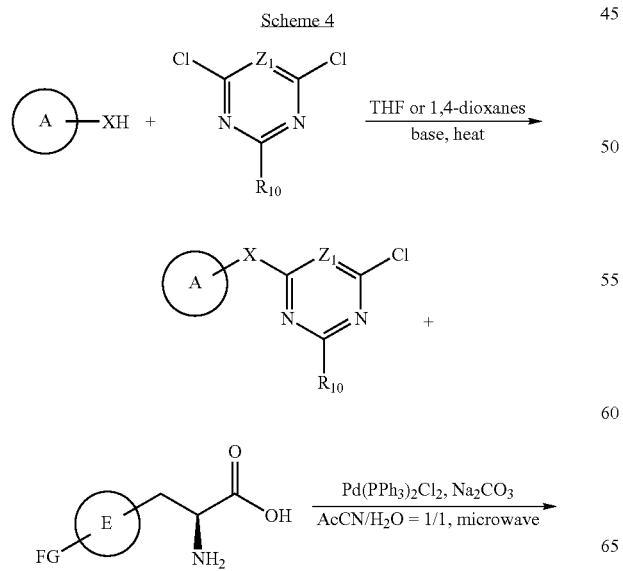

-continued

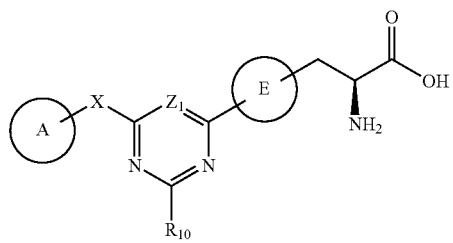

wherein, for example, X is N, O or S, and FG is defined below:

FG=B(OH)$_2$ when E is optionally substituted Phenyl

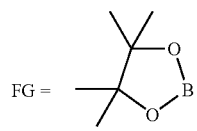

when E is:

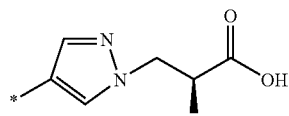

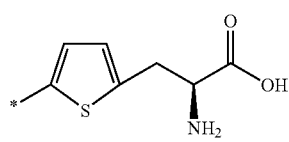

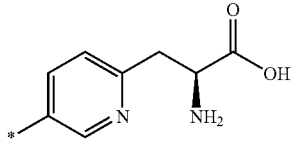

FG=H when E is:

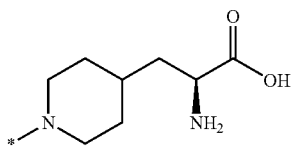

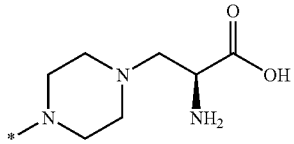

Ester derivatives of these and other compounds of the invention can be readily prepared using methods such as that shown below in Scheme 5, wherein E is optionally substituted phenyl:

Scheme 5
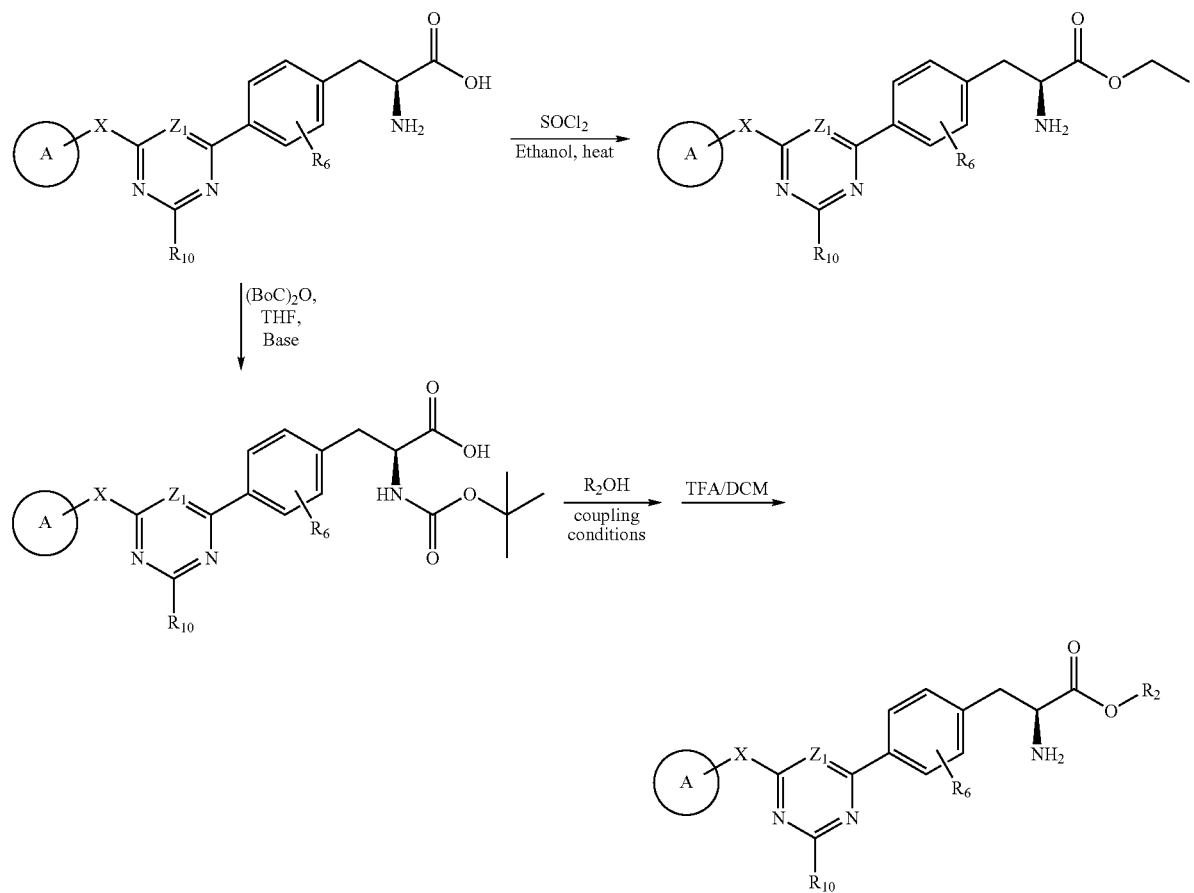
An alternate approach to the preparation of triazine-based compounds is shown below in Scheme 6:
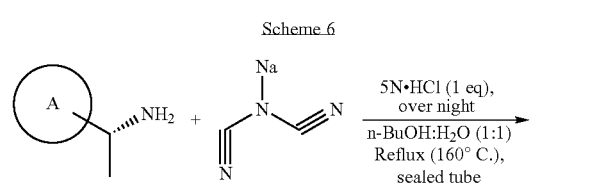
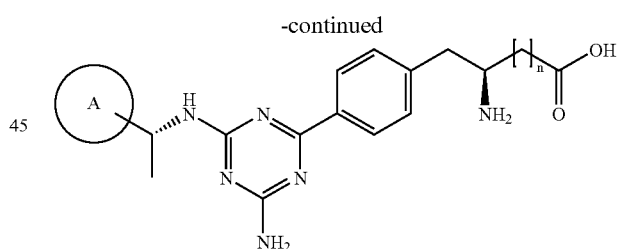
The cyclic moiety D can be any of a variety of structures, which are readily incorporated into compounds of the invention. For example, compounds wherein D is oxazole can be prepared as shown below in Scheme 7:
Scheme 7
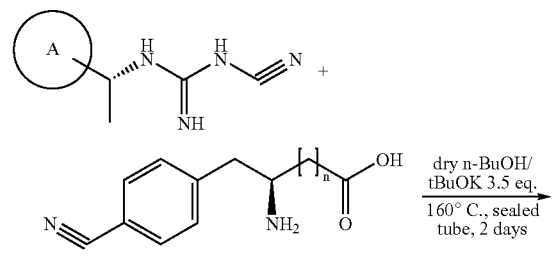
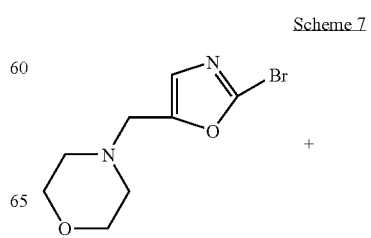

-continued

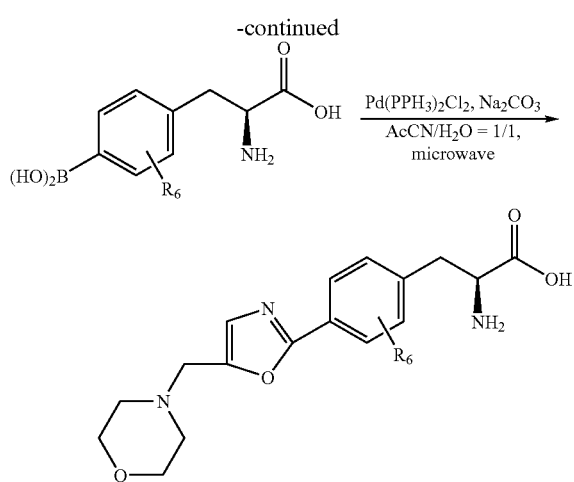

Using methods known in the art, the synthetic approaches shown above are readily modified to obtain a wide range of compounds. For example, chiral chromatography and other techniques known in the art may be used to separate stereoisomers of the final product. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972). In addition, as shown in some of the schemes above, syntheses may utilize chiral starting materials to yield stereomerically enriched or pure products.

5.4. Methods of Use

This invention is directed, in part, to methods of treating pulmonary hypertension and related diseases and disorders. Pulmonary hypertension includes idiopathic and familial PH. It also includes PH associated with other diseases or conditions (e.g., collagen vascular disease, congenital systemic-to-pulmonary shunts, a drug or toxin, Gaucher disease, a glycogen storage disease, hereditary hemorrhagic telangiectasia, hemoglobinopathies, HIV infection, a myeloproliferative disorder, portal hypertension, splenectomy, a thyroid disorder). It also includes PAH and PAH associated with significant venous or capillary involvement. It also includes PH associated with pulmonary veno-occlusive disease or pulmonary capillary hemangiomatosis. It also includes persistent PH of the newborn.

Particular methods comprise administering to a patient therapeutically or prophylactically effective amounts of a tryptophan hydroxylase (TPH) inhibitor and at least one second active pharmaceutical ingredient. Second active pharmaceutical ingredients include those that can affect vasodilation or vasoconstriction.

One embodiment of the invention encompasses a method of treating, managing or preventing pulmonary hypertension, which comprises administering to a patient in need thereof therapeutically or prophylactically effective amounts of an endothelin receptor antagonist and a tryptophan hydroxylase inhibitor. Examples of endothelin receptor antagonists include those which antagonize the $ET_A$ receptor, the $ET_B$ receptor, or both the $ET_A$ and $ET_B$ receptors. Particular endothelin receptor antagonists include ambrisentan, BMS-193884, bosentan, darusentan, SB-234551, sitaxsentan, and tezosentan.

Another embodiment encompasses a method of treating, managing or preventing pulmonary hypertension, which comprises administering to a patient in need thereof therapeutically or prophylactically effective amounts of an anticoagulant and a tryptophan hydroxylase inhibitor. Examples of anticoagulants include vitamin K antagonists (e.g., warfarin, acenocoumarol, phenprocoumon, phenindione), herparin and derivatives thereof (e.g., fondaparinux), and direct thrombin inhibitors (e.g., argatroban, bivalirudin, lepirudin, ximelagatran).

Another embodiment encompasses a method of treating, managing or preventing pulmonary hypertension, which comprises administering to a patient in need thereof therapeutically or prophylactically effective amounts of a calcium channel blocker and a tryptophan hydroxylase inhibitor. Examples of calcium channel blockers include dihydropyridines (e.g., amlodipine, felodipine, nicardipine, nifedipine, nimodipine, nisoldipine, nitrenidipine, lacidipine, lercanidipine), phenylalkylamines (e.g., verapamil, gallopamil), benzothiazepines (e.g., diltiazem), and menthol.

Another embodiment encompasses a method of treating, managing or preventing pulmonary hypertension, which comprises administering to a patient in need thereof therapeutically or prophylactically effective amounts of a prostacyclin and a tryptophan hydroxylase inhibitor. Examples of prostacyclind include epoprostenol, iloprost and treprostinil.

Another embodiment encompasses a method of treating, managing or preventing pulmonary hypertension, which comprises administering to a patient in need thereof therapeutically or prophylactically effective amounts of nitric oxide or a nitric oxide precursor or releasing compound, and a tryptophan hydroxylase inhibitor.

Another encompasses a method of treating, managing or preventing pulmonary hypertension, which comprises administering to a patient in need thereof therapeutically or prophylactically effective amounts of a phosphodiesterase 5 inhibitor and a tryptophan hydroxylase inhibitor. Examples of phosphodiesterase 5 inhibitors include sildenafil, tadalafil, and vardenafil.

Another embodiment encompasses a method of treating, managing or preventing pulmonary hypertension, which comprises administering to a patient in need thereof therapeutically or prophylactically effective amounts of a diuretic and a tryptophan hydroxylase inhibitor. Examples of diuretics include high ceiling loop diuretics (e.g., furosemide, ethacrynic acid, torasemide, bumetanide), thiazides (e.g., hydrochlorothiazide), potassium sparing diuretics (e.g., spironolactone), and osmotic diuretics (e.g., mannitol).

Another embodiment encompasses a method of treating, managing or preventing pulmonary hypertension, which comprises administering to a patient in need thereof therapeutically or prophylactically effective amounts of a platelet derived growth factor and a tryptophan hydroxylase inhibitor. An example of a platelet derived growth factor is imatinib.

The dose and method of administration of a TPH inhibitor can be readily determined by those of ordinary skill in the art. For example, an inhibitor can be titrated until the severity of a serotonin-mediated adverse effect diminishes. Alternatively, blood 5-HT levels can be directly measured and correlated to the amount of TPH inhibitor administered.

5.5. Pharmaceutical Compositions

This invention encompasses pharmaceutical compositions comprising a TPH inhibitor (e.g., a potent TPH1 inhibitor) and at least one other active pharmaceutical ingredient that can affect vasodilation or vasoconstriction. Examples of such other active pharmaceutical ingredients include those described herein, as well as other known by those skilled in the art.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, the oral administration of a compound susceptible to degradation in the stomach may be achieved using an enteric coating. Similarly, a formulation may contain ingredients that facilitate delivery of the active ingredient(s) to the site of action. For example, compounds may be administered in liposomal formulations in order to protect them from degradative enzymes, facilitate transport in circulatory system, and effect their delivery across cell membranes.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol®, and Encapsin™ (see, e.g., Davis and Brewster, *Nat. Rev. Drug Disc.* 3:1023-1034 (2004)), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO: cornoil).

Poorly soluble compounds may also be incorporated into suspensions using other techniques known in the art. For example, nanoparticles of a compound may be suspended in a liquid to provide a nanosuspension (see, e.g., Rabinow, *Nature Rev. Drug Disc.* 3:785-796 (2004)). Nanoparticle forms of compounds described herein may be prepared by the methods described in U.S. Patent Publication Nos. 2004-0164194, 2004-0195413, 2004-0251332, 2005-0042177 A1, 2005-0031691 A1, and U.S. Pat. Nos. 5,145,684, 5,510,118, 5,518,187, 5,534,270, 5,543,133, 5,662,883, 5,665,331, 5,718,388, 5,718,919, 5,834,025, 5,862,999, 6,431,478, 6,742,734, 6,745,962, the entireties of each of which are incorporated herein by reference. In one embodiment, the nanoparticle form comprises particles having an average particle size of less than about 2000 nm, less than about 1000 nm, or less than about 500 nm.

The composition, shape, and type of a dosage form will typically vary depending with use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. How to account for such differences will be apparent to those skilled in the art. See, e.g., *Remington's Pharmaceutical Sciences*, 18th ed., Mack Publishing, Easton Pa. (1990).

5.5.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.5.2. Parenteral Dosage Forms

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

6. EXAMPLES

6.1. Production of tph1 Gene Disrupted Mice

Exon 3 of the murine TPH1 gene was removed by gene targeting essentially as described by Wattler et al., *Biotechniques* 26(6):1150-6 (1999). The resulting knockout animals displayed normal TPH activity in the brain but drastically reduced TPH expression in the gut.

6.2. Physiological Effects of tph1 Gene Disruption

Mice homozygous (−/−) for the disruption of tph1 were studied in conjunction with mice heterozygous (+/−) for the disruption of the gene, along with wild-type (+/+) litter mates. During this analysis, the mice were subject to a medical work-up using an integrated suite of medical diagnostic procedures designed to assess the function of the major organ systems in a mammalian subject. By studying the homozygous (−/−) knockout mice in the described numbers and in conjunction with heterozygous (+/−) and wild-type (+/+) litter mates, more reliable and repeatable data was obtained.

Disruption of tph1 gene primarily affected the GI tract isoform of TPH (TPH1), and had little or no effect on the brain isoform of TPH (TPH2). Disruption of the gene caused no measurable adverse effects on the central nervous system. This was confirmed by serotonin immunochemistry, which showed that serotonin was greatly reduced or absent in the stomach, duodenum, jejunum, ileum, cecum and colon, while serotonin levels were unaffected in raphe neurons.

Mice homozygous (−/−) for the disruption of the tph1 gene had a decrease in thrombosis without a significant increase in bleeding or other adverse indications.

6.3. HPLC Characterization

In some of the following synthetic examples, high performance liquid chromatography (HPLC) retention times are provided. Unless otherwise noted, the various conditions used to obtain those retention times are described below:

Method A: YMC-PACK ODS-A 3.0×50 mm; Solvent A=90% water, 10% MeOH, 0.1% TFA; Solvent B=90% MeOH, 10% water, 0.1% TFA; B % from 0 to 100% over 4 min.; flow rate=2 ml/min; observation wavelength=220 nm.

Method B: YMC-PACK ODS-A 3.0×50 mm; Solvent A=90% water, 10% MeOH, 0.1% TFA; Solvent B=90% MeOH, 10% water, 0.1% TFA; % B from 10 to 100% over 4 min.; flow rate=3 ml/min; observation wavelength=220 nm.

Method C: YMC-PACK ODS-A 3.0×50 mm; Solvent A=90% water, 10% MeOH, 0.1% TFA; Solvent B=90% MeOH, 10% water, 0.1% TFA; B % from 0 to 100% over 5 min.; flow rate=2 ml/min.; observation wavelength=220 nm.

Method D: Shim VP ODS 4.6×50 mm; Solvent A=90% water, 10% MeOH, 0.1% TFA; Solvent B=90% MeOH, 10% water, 0.1% TFA; B % from 0 to 100% over 4 min.; flow rate=3 ml/min; observation wavelength=220 nm.

Method E: Shim VP ODS 4.6×50 mm; Solvent A=90% water, 10% MeOH, 0.1% TFA; Solvent B=90% MeOH, 10% water, 0.1% TFA; B % from 0 to 100% over 4 min.; flow rate=3 ml/min; observation wavelength=254 nm.

Method F: YMC-PACK ODS-A 4.6×33 mm; Solvent A=90% water, 10% MeOH, 0.1% TFA; Solvent B=90% MeOH, 10% water, 0.1% TFA; B % from 0 to 100% over 4 min.; flow rate=3 ml/min.; observation wavelength=220 nm.

Method G: YMC-PACK ODS-A 4.6×50 mm; Solvent A=90% water, 10% MeOH, 0.1% TFA; Solvent B=90% MeOH, 10% water, 0.1% TFA; B % from 0 to 100% over 2 min.; flow rate=2.5 ml/min.; observation wavelength=220 nm.

Method H: C18 4.6×20 mm; Solvent A=90% water, 10% MeOH, 0.1% TFA; Solvent B=90% MeOH, 10% water, 0.1% TFA; B % from 0 to 100% over 2 min. flow rate=2 ml/min.; observation wavelength=220 nm.

Method I: YMC PACK ODS-A 3.0×50 mm; Solvent A=90% water, 10% MeOH, 0.1% TFA; Solvent B=90% MeOH, 10% water, 0.1% TFA; B % from 10 to 100% over 4 min.; flow rate=2 ml/min.; observation wavelength=220 nm.

Method J: YMC Pack ODS-A 3.0×50 mm; Solvent A=$H_2O$, 0.1% TFA; Solvent B=MeOH, 0.1% TFA; % B from about 10 to about 90% over 4 min.; flow rate=2 ml/min.; observation wavelength=220 nm.

Method K: Sunfire C18 50 mm×4.6 mm×3.5 μm; Solvent A=10 mM $NH_4OAc$ in water; Solvent B=MeCN; B % from 10 to 95% over 2 min.; flow rate=4.5 ml/min.; observation wavelength=220 nm.

Method L: Sunfire C18 50 mm×4.6 mm×3.5 μm; Solvent A=10 mM $NH_4OAc$; Solvent B=MeCN; B % from 2 to 20% over 0.8 min, then to 95% B over 2 min; flow rate=4.5 ml/min.; observation wavelength=220 nm.

Method M: YMC-PACK ODS-A 4.6×33 mm; Solvent A=90% water, 10% MeOH, 0.1% TFA; Solvent B=90% MeOH, 10% water, 0.1% TFA; B % from 0 to 100% over 5 min.; flow rate=2.5 ml/min.; observation wavelength=254 nm.

Method N: YMC-PACK ODS-A 3.0×50 mm; Solvent A=$H_2O$, 0.1% TFA; Solvent B=MeOH, 0.1% TFA; B % from 10 to 90% over 4 min.; flow rate=2 ml/min.; observation wavelength=220 and 254 nm.

Method O: YMC-PACK ODS-A 3.0×50 mm; Solvent A=90% water, 10% MeOH with 0.1% TFA; Solvent B=90% MeOH, 10% water with 0.1% TFA; B % from 0 to 100% over 4 min.; flow, rate=2 ml/min.; observation wavelength=220 and 254 nm.

Method P: ShimPack VP ODS 4.6×50 mm; Solvent A=90% $H_2O$, 10% MeOH, 1% TFA; Solvent B=10% $H_2O$, 90% MeOH, 1% TFA; B % from 0 to 100% over 2 min.; flow rate=3.5 ml/min.; observation wavelength=220 and 254 nm.

Method Q: Shim VP ODS 4.6×50 mm; Solvent A=$H_2O$ with 0.1% TFA; Solvent B=MeOH with 0.1% TFA; B % from 0 to 100% over 4 min.; flow rate=3 ml/min.; observation wavelength=254 nm.

Method R: YMC Pack ODS-A 4.6×33 mm; Solvent A=$H_2O$, 0.1% TFA; Solvent B=MeOH with 0.1% TFA; B % from 10 to 90% over 3 min.; flow rate 2 ml/min.; observation wavelength 220 and 254 nm.

Method S: YMC-Pack ODS-A 3.0×50 mm; Solvent A=90% $H_2O$, 10% MeOH, 1% TFA; Solvent B=10% $H_2O$, 90% MeOH, 1% TFA; B % from 10 to 90% over 4 min.; flow rate=2 ml/min. observation wavelength=220 and 254 nm.

6.4. Synthesis of (S)-2-Amino-3-(4-(4-amino-6-((R)-1-(naphthalen-2-yl)ethylamino)-1,3,5-triazin-2-yl)phenyl)propanoic acid

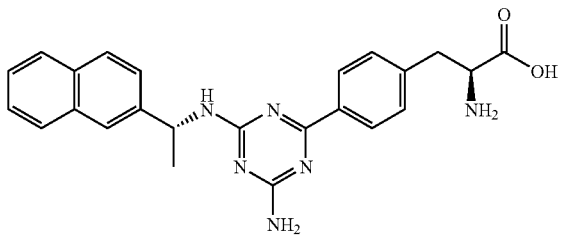

A mixture of 2-amino-4,6-dichloro-[1,3,5]triazine (200 mg, 1.21 mmol), (R)-(+)-1-(2-naphthyl)ethylamine (207 mg, 1.21 mmol) and diisopropyl-ethylamine (3.63 mmol) was dissolved in 150 ml of 1,4-dioxane. The solution was refluxed at 90° C. for 3 hours. After the completion of reaction (monitored by LCMS), solvent was removed and the reaction mixture was extracted with $CH_2Cl_2$ (100 ml) and $H_2O$ (100 ml). The organic layer was separated and washed with $H_2O$ (2×100 ml), dried over $Na_2SO_4$, and concentrated in vacuo to give crude intermediate. The crude compound was dissolved in 5 ml of MeCN and 5 ml of $H_2O$ in a 20 ml microwave reaction vial. To this solution were added L-p-borono-phenylalanine (253 mg, 1.21 mmol), sodium carbonate (256 mg, 2.42 mmol) and catalytic amount of dichlorobis(triphenylphosphine)-palladium(II) (42.1 mg, 0.06 mmol). The mixture was sealed and stirred in the microwave reactor at 150° C. for 5 minutes, followed by the filtration through celite. The filtrate was concentrated and dissolved in MeOH and $H_2O$ (1:1) and purified by preparative HPLC using MeOH/$H_2O$/TFA solvent system. The combined pure fractions were evaporated in vacuo and further dried on a lyophilizer to give 238 mg of 2-amino-3-{4-[4-amino-6-(1-naphthalen-2-yl)-ethylamino)-[1,3,5]triazin-2-yl]-phenyl}-propionic acid (yield: 46%, LC: Column: YMC Pack ODS-A 3.0×50 mm, % B=0~100%, Gradient time=4 min, Flow Rate=2 ml/min, wavelength=220, Solvent A=90:10 water:MeOH w/0.1% TFA, Solvent B=90:10 MeOH:water w/0.1% TFA, RT=2.785 min, MS: M+1=429). NMR: $^1$H-NMR (400 MHz, $CD_3OD$): δ 1.65 (d, 3H), 3.22-3.42 (m, 2H), 4.3 (m, 1H), 5.45 (m, 1H), 7.4 (m, 1H), 7.6 (m 4H), 7.8 (m, 4H), 8.2 (m, 2H).

6.5. Alternative Synthesis of (S)-2-Amino-3-(4-(4-amino-6-((R)-1-(naphthalen-2-yl)ethylamino)-1,3,5-triazin-2-yl)phenyl)propanoic acid (R)-1-(1-(Napthalen-2-yl)ethyl) cyanoguanidine was prepared by forming a mixture of naphthalene amine (1 equivalent), sodium dicyanide (0.95 eq.) and followed by 5N HCl (1 eq.) in n-BuOH: $H_2O$ (1:1). The mixture was refluxed for 1 day in a sealed tube at 160° C., and progress of reaction was monitored by LCMS. After completion of reaction, solvent (n-BuOH) was removed under reduced pressure and 1N HCl was added to adjust pH to 3-5 range. The aqueous solution was extracted with EtOAc (2×100) and combined organic phase was dried over $Na_2SO_4$. Solvent was removed in vacuo to give crude product. The compound was purified by ISCO column chromatography using as the solvent system EtOAc:hexane (7:3 and 1:1), to obtain white solid 48-71% yield for 1 g to 22.5 gram scale. NMR: $^1$H-NMR (400 MHz, $CD_3OD$): δ 1.5 (d, 3H), 5.1 (m, 1H), 7.5 (m, 4H), 7.8 (s, 1H), 7.9 (m, 2H); LCMS: RT 1.69, M+1: 239, Yield: 71%.

The title compound was prepared from (R)-1-(1-(naphtalen-2-yl)ethyl) cyanoguanidine according to the method shown in Scheme 6.

6.6. Synthesis of (S)-2-Amino-3-(4-(4-amino-6-((4'-methylbiphenyl-4-yl)methylamino)-1,3,5-triazin-2-yl)phenyl)propanoic acid

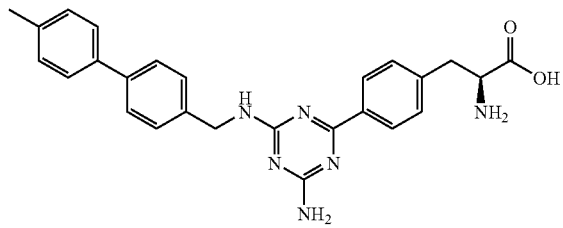

A mixture of 2-amino-4,6-dichloro-[1,3,5]triazine (100 mg, 0.606 mmol), 4'-methyl-biphenyl-4-yl-methylamine (142 mg, 0.606 mmol), and cesium carbonate (394 mg, 1.21 mmol) was dissolved in 1,4-dioxane (1.5 ml) and $H_2O$ (1.5 ml) in a 5 ml microwave vial. The mixture was stirred in microwave reactor at 100° C. for 15 minutes. Solvent was removed and the residue was dissolved in $CH_2Cl_2$ (20 ml) and washed with $H_2O$ (2×20 ml), dried over $Na_2SO_4$ and then removed in vacuo. The crude intermediate was then dissolved in 1.5 ml of MeCN and 1.5 ml of $H_2O$ in a 5 ml microwave vial. To this solution were added L-p-borono-phenylalanine (126 mg, 0.606 mmol), sodium carbonate (128 mg, 1.21 mmol) and catalytic amount of dichlorobis(triphenylphosphine)-palladium(II) (21.1 mg, 0.03 mmol). The mixture was sealed and stirred in the microwave reactor at 150° C. for 5 minutes followed by the filtration through celite. The filtrate was concentrated and dissolved in MeOH and $H_2O$ (1:1) and purified by preparative HPLC using MeOH/$H_2O$/TFA solvent system. The combined pure fractions were evaporated in vacuo and further dried on a lyophilizer to give 21.6 mg of 2-amino-3-(4-{4-amino-6-[(4'-methyl-biphenyl-4-ylmethyl)-amino]-[1,3,5]triazin-2-yl}-phenyl)-propionic acid (LC: Column: YMC Pack ODS-A 3.0×50 mm, % B=0~100%, Gradient time=4 min, Flow Rate=2 ml/min, wavelength=220, Solvent A=90:10 water:MeOH w/ 0.1% TFA, Solvent B=90:10 MeOH:water w/0.1% TFA, RT=3.096 min, MS: M+1=455). $^1$H NMR (400 MHz, $CD_3OD$) δ 2.33 (s, 3H), 3.24-3.44 (m, 2H), 4.38 (m, 1H), 7.02 (d, 2H), 7.42 (m, 2H), 7.50-7.60 (m, 6H), 8.22 (m, 2H).

6.7. Synthesis of (S)-2-Amino-3-(4-(4-morpholino-6-(naphthalen-2-ylmethylamino)-1,3,5-triazin-2-yl)phenyl)propanoic acid

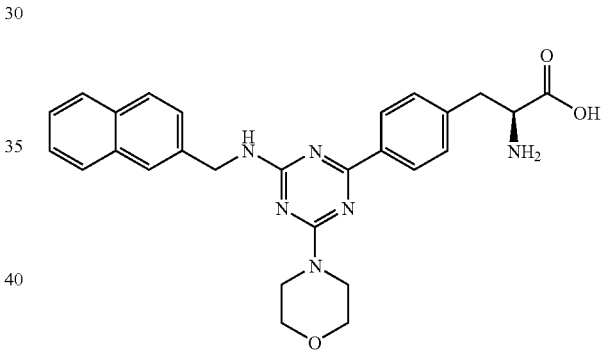

A mixture of 2,4-dichloro-6-morpholin-4-yl-[1,3,5]triazine (121 mg, 0.516 mmol), C-naphthalen-2-yl-methylamine hydrochloride (100 mg, 0.516 mmol), cesium carbonate (336 mg, 1.03 mmol) was dissolved in 1,4-Dioxane (1.5 ml) and $H_2O$ (1.5 ml) in a 5 ml microwave vial. The mixture was stirred in microwave reactor at 180° C. for 600 seconds. Solvent was removed, and the residue was dissolved in $CH_2Cl_2$ (10 ml) and washed with $H_2O$ (2×10 ml), dried over $Na_2SO_4$ and then in vacuo. The residue was purified by preparative HPLC to give 20 mg intermediate (yield 11%, M+1=356). The intermediate was then dissolved in 0.5 ml of MeCN and 0.5 ml of $H_2O$ in a 2 ml microwave vial. To this solution were added L-p-borono-phenylalanine (11.7 mg, 0.0562 mmol), sodium carbonate (11.9 mg, 0.112 mmol) and a catalytic amount of dichlorobis(triphenylphosphine)-palladium(II) (2.0 mg, 5%). The mixture was sealed and stirred in the microwave reactor at 150° C. for 5 minutes followed by the filtration through celite. The filtrate was concentrated and dissolved in MeOH and $H_2O$ (1:1) and purified by preparative HPLC using MeOH/$H_2O$/TFA solvent system. The combined pure fractions were evaporated in vacuo and further dried on lyophilizer to give 17 mg of 2-amino-3-(4-{4-morpholin-4-yl-6-[(naphthalene-2-ylmethyl)-amino]-[1,3,5]triazin-2-yl}-phenyl)-propionic acid (yield: 63%, LC: Method B, RT=3.108 min, MS: M+1=486).

6.8. Synthesis of (2S)-2-Amino-3-(4-(2-amino-6-(2,2,2-trifluoro-1-(2-(trifluoromethyl)phenyl)ethoxy)pyrimidin-4-yl)phenyl)propanoic acid

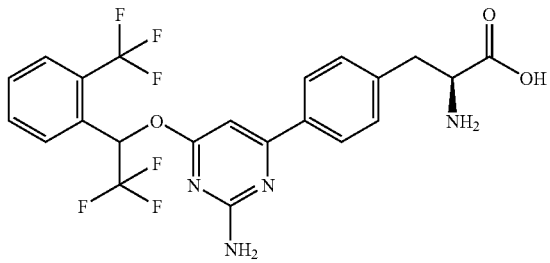

Tetrabutylammonium fluoride (0.1 ml; 1.0 M solution in tetrahydrofuran) was added to a solution of 2-trifluoromethyl-benzaldehyde (1.74 g, 10 mmol) and trifluoromethyltrimethylsilane (TMSCF$_3$) (1.8 ml, 12 mmol) in 10 ml THF at 0° C. The formed mixture was warmed up to room temperature and stirred for 4 hours. The reaction mixture was then treated with 12 ml of 1N HCl and stirred overnight. The product was extracted with ethyl acetate (3×20 ml). The organic layer was separated and dried over sodium sulfate. The organic solvent was evaporated to give 2.2 g of 1-(2-trifluoromethylphenyl)-2,2,2-trifluoro-ethanol, yield 90%.

NaH (80 mg, 60%, 3.0 mmol) was added to a solution of 1-(2-trifluoromethylphenyl)-2,2,2-trifluoro-ethanol (244 mg, 1 mmol) in 10 ml of anhydrous THF. The mixture was stirred for 20 minutes, 2-amino-4,6-dichloro-pyrimidine (164 mg, 1 mmol) was added and then the reaction mixture was heated at 70° C. for 1 hour. After cooling, 5 ml water was added and ethyl acetate (20 ml) was used to extract the product. The organic layer was dried over sodium sulfate. The solvent was removed by rotovap to give 267 mg of 4-chloro-6-[2,2,2-trifluoro-1-(2-trifluoromethylphenyl)-ethoxy]-pyrimidin-2-ylamine, yield 71%.

In a microwave vial, 4-chloro-2-amino-6-[1-(2-trifluoromethylphenyl)-2,2,2-trifluoro-ethoxy]-pyrimidine (33 mg, 0.1 mmol), 4-borono-L-phenylalanine (31 mg, 0.15 mmol) and 1 ml of acetonitrile, 0.7 ml of water. 0.3 ml of 1N aqueous sodium carbonate was added to above solution followed by 5 mole percent of dichlorobis(triphenylphosphine)-palladium (II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 5.6 mg of 2-amino-3-(4-{2-amino-6-[2,2,2-trifluoro-1-(2-triifluoromethylphenyl)-ethoxy]-pyrimidin-4-yl}-phenyl)-propionic acid. $^1$H NMR (400 MHz, CD$_3$OD) δ 7.96 (m, 3H), 7.80 (d, J=8.06 Hz, 1H), 7.74 (t, J=7.91 Hz 1H), 7.63 (t, J=8.06 Hz, 1H), 7.41 (d, J=8.3 Hz, 2H), 7.21 (m, 1H), 6.69 (s, 1H), 3.87 (m, 1H), 3.34 (m, 1H), 3.08 (m, 1H).

6.9. Synthesis of (2S)-2-Amino-3-(4-(2-amino-6-(2,2,2-trifluoro-1-p-tolylethoxy)pyrimidin-4-yl)phenyl)propanoic acid

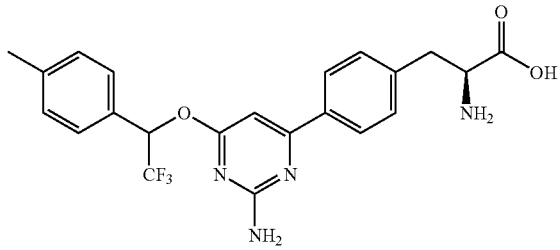

Tetrabutylammonium fluoride (0.1 ml; 1.0 M solution in tetrahydrofuran) was added to a solution of 4-methyl-benzaldehyde (1.2 g, 10 mmol) and TMSCF$_3$ (1.8 ml, 12 mmol) in 10 ml THF at 0° C. The formed mixture was warmed up to room temperature and stirred for 4 hours. The reaction mixture was then treated with 12 ml of 1N HCl and stirred overnight. The product was extracted with ethyl acetate (3×20 ml). The organic layer was separated and dried over sodium sulfate. The organic solvent was evaporated to give 1.6 g of 1-(4-methylphenyl)-2,2,2-trifluoro-ethanol, yield 86%.

NaH (80 mg, 60%, 3.0 mmol) was added to a solution of 1-(4-methylphenyl)-2,2,2-trifluoro-ethanol (190 mg, 1 mmol) in 10 ml of anhydrous THF. The mixture was stirred for 20 minutes, 2-amino-4,6-dichloro-pyrimidine (164 mg, 1 mmol) was added and then the reaction mixture was heated at 70° C. for 1 hour. After cooling, 5 ml water was added and ethyl acetate (20 ml) was used to extract the product. The organic layer was dried over sodium sulfate. The solvent was removed by rotovap to give 209 mg of 4-chloro-6-[1-(4-methylphenyl)-2,2,2-trifluoro-ethoxy]-pyrimidin-2-ylamine, yield 66%.

A microwave vial was charged with 4-chloro-2-amino-6-[1-(4-methylphenyl)-2,2,2-trifluoro-ethoxy]-pyrimidine (33 mg, 0.1 mmol), 4-borono-L-phenylalanine (31 mg, 0.15 mmol) and 1 ml of acetonitrile, 0.7 ml of water. Aqueous sodium carbonate (0.3 ml, 1N) was added to above solution followed by 5 mol percent of dichlorobis(triphenylphosphine)-palladium(II). The reaction vessel was sealed and heated to 150° C. for 5 minutes with microwave. After cooling, the reaction mixture was evaporated to dryness. The residue was dissolved in 2.5 ml of methanol, was then purified by Prep-LC to give 14.6 mg of 2-amino-3-(4-{2-amino-6-[2,2,2-trifluoro-1-(4-methylphenyl)-ethoxy]-pyrimidin-4-yl}-phenyl)-propionic acid. $^1$H NMR (300 MHz, CD$_3$OD) δ 7.94 (d, J=8.20 Hz, 2H), 7.47 (d, J=7.24 Hz, 4H), 7.27 (d, J=8.01 Hz, 2H) 6.80 (s, 1H), 6.75 (m, 1H), 4.30 (t, 1H), 3.21-3.44 (m, 2H), 2.37 (s, 3H).

6.10. Synthesis of (2S)-2-Amino-3-(4-(2-amino-6-(1-cyclohexyl-2,2,2-trifluoroethoxy)pyrimidin-4-yl)phenyl)propanoic acid

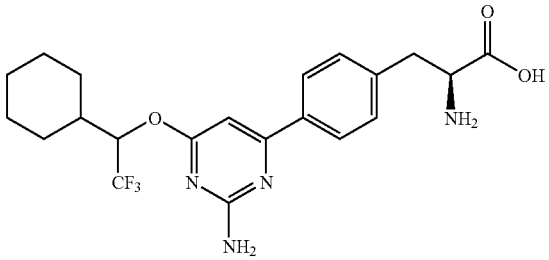

Cyclohexanecarbaldehyde (0.9 g, 5 mmol) was dissolved in 10 ml aqueous 1,4-dioxane, to which 200 mg (10 mmol) sodium borohydride was added. The reaction was run overnight at room temperature. After completion of the reaction, 5 ml 10% HCl solution was added and the product was extracted with ethyl acetate. The organic layer was separated and dried over sodium sulfate. The organic solvent was evaporated to give 0.8 g of 1-cyclohexyl-2,2,2-trifluoro-ethanol, yield 88%.

NaH (80 mg, 60%, 3.0 mmol) was added to the solution of 1-cyclohexyl-2,2,2-trifluoro-ethanol (182 mg, 1 mmol) in 10 ml of anhydrous THF, the mixture was stirred for 20 minutes, 2-amino-4,6-dichloro-pyrimidine (164 mg, 1 mmol) was added and then the reaction mixture was heated at 70° C. for 1 hour. After cooling, 5 ml water was added and ethyl acetate (20 ml) was used to extract the product. The organic layer was dried over sodium sulfate. The solvent was removed by rotovap to give 202 mg of 4-chloro-6-[1-cyclohexyl-2,2,2-trifluoro-ethoxy]-pyrimidin-2-ylamine, yield 65%.

In a microwave vial, 4-chloro-2-amino-6-[1-cyclohexane-2,2,2-trifluoro-ethoxy]-pyrimidine (33 mg, 0.1 mmol), 4-borono-L-phenylalanine (31 mg, 0.15 mmol) and 1 ml of acetonitrile, 0.7 ml of water, 0.3 ml of aqueous sodium carbonate (1M) was added to above solution followed by 5 mol percent of dichlorobis(triphenylphosphine)-palladium(II). The reaction vessel was sealed and heated to 150° C. for 5 minutes with a microwave. After cooling, the reaction mixture was evaporated to dryness, the residue was dissolved in 2.5 ml of methanol, and the product was purified by Prep-LC to give 4.9 mg 2-amino-3-{4-[2-amino-6-(1-cyclohexyl-2,2,2-trifluoro-ethoxy]-pyrimidin-4-yl}-phenyl)-propionic acid. $^{1}$H NMR (300 MHz, CD$_{3}$Cl) δ 7.95 (d, J=8.39 Hz, 2H), 7.49 (d, J=8.39 Hz, 2H), 6.72 (s, 1H), 5.90 (m, 1H), 4.33 (t, 1H), 3.21-3.44 (m, 2H), 1.73-2.00 (m, 6H), 1.23-1.39 (m, 5H).

6.11. Synthesis of (S)-2-Amino-3-(4-(6-(2-fluorophenoxy)pyrimidin-4-yl)phenyl)propanoic acid

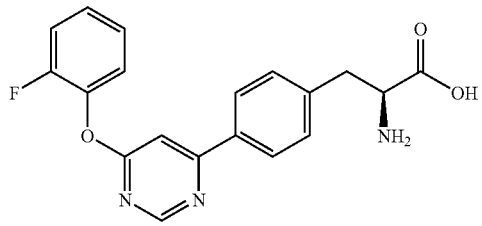

NaH (80 mg, 60%, 3.0 mmol) was added to a solution of 2-fluorophenol (112 mg, 1 mmol) in 10 ml of anhydrous THF, the mixture was stirred for 20 minutes, 4,6-dichloro-pyrimidine (149 mg, 1 mmol) was added and then the reaction mixture was heated at 70° C. for 1 hour. After cooling, 5 ml water was added and ethyl acetate (20 ml) was used to extract the product. The organic layer was dried over sodium sulfate. The solvent was removed by rotovap to give 146 mg of 4-chloro-6-(2-fluorophenoxy)-pyrimidine, yield 65%.

A microwave vial (2 ml) was charged with 4-chloro-6-[2-fluorophenoxy]-pyrimidine, (33 mg, 0.1 mmol), 4-borono-L-phenylalanine (31 mg, 0.15 mmol) and 1 ml of actonitrile, 0.7 ml of water, 0.3 ml of aqueous sodium carbonate (1M) was added to above solution followed by 5 mol % of dichlorobis(triphenylphosphine)-palladium(II). The reaction vessel was sealed and heated to 150° C. for 5 minutes by microwave. After cooling, the reaction mixture was evaporated to dryness, the residue was dissolved in 2.5 ml of methanol, and the product was purified with Prep-LC to give 4.9 mg 2-amino-3-{4-[2-amino-6-(1-2-fluorophenyl-2,2,2-trifluoro-ethoxy]-pyrimidin-4-yl}-phenyl)-propionic acid. $^{1}$H NMR (400 MHz, CD$_{3}$OD) δ 8.74 (s, 1H), 8.17 (d, J=8.06 Hz, 2H), 7.63 (s, 1H), 7.50 (d, J=8.06 Hz, 2H), 7.30 (m, 5H), 4.33 (m, 1H), 3.34 (m, 1H).

6.12. Synthesis of (2S)-2-Amino-3-(4-(4-(3-(4-chlorophenyl)piperidin-1-yl)-1,3,5-triazin-2-yl)phenyl) propanoic acid

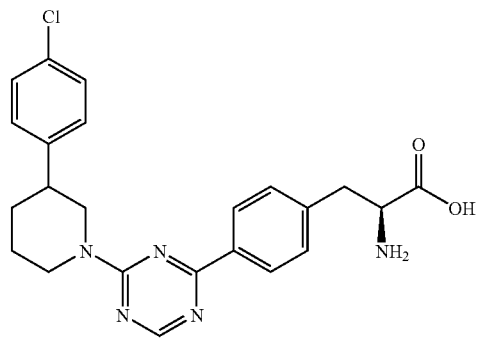

3-(4-Chlorophenyl)piperidine (232 mg, 1 mmol) was added to a solution of 2,4-dichlorotriazine (149.97 mg, 1 mmol), and 300 mg diisopropylethyl amine in 10 ml THF at 0° C. The formed mixture was warmed up to room temperature and stirred for 1 hour. The product was extracted with ethyl acetate (3×20 ml). The organic layer was separated and dried over sodium sulfate. The organic solvent was evaporated to give 328 mg of 2-chloro-4-[3-(4-chlorophenyl)-piperidin-1-yl]-[1,3,5]triazine.

A microwave vial was charged with 2-chloro-4-[3-(4-chlorophenyl)-piperidin-1-yl]-[1,3,5]triazine (62 mg, 0.2 mmol), 4-borono-L-phenylalanine (60 mg, 0.3 mmol), 1 ml of acetonitrile, and 0.7 ml of water. Aqueous sodium carbonate (0.6 ml; 1M) was added to the solution, followed by 5 mol percent dichlorobis(triphenylphosphine)-palladium(II). The reaction vessel was sealed and heated to 150° C. for 5 minutes with microwave. After cooling, the reaction mixture was evaporated to dryness. The residue was dissolved in 2.5 ml of methanol, was then purified by Prep-LC to give 5.1 mg of 2-amino-3-(4-{4-[3-(4-chlorophenyl)-piperidin-1-yl]-[1,3,5]triazin-2-yl}-phenyl)-propionic acid. $^{1}$H NMR (400 MHz, CD$_{3}$Cl) δ 8.58 (d, 2H), 8.05 (d, 2H), 7.47 (m, 5H), 4.96 (m, 1H), 4.23 (m, 2H), 3.21-3.44 (m, 4H), 2.37 (m, 5H).

6.13. Synthesis of (2S)-2-Amino-3-(4-(4-amino-6-(2,2,2-trifluoro-1-phenylethoxy)-1,3,5-triazin-2-yl) phenyl)propanoic acid

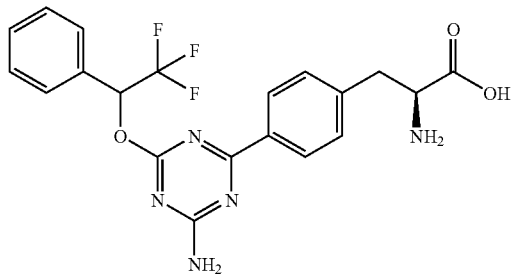

NaH (80 mg, 60%, 3.0 mmol) was added to a solution of 2,2,2-trifluoro-1-phenylethanol (176 mg, 1 mmol) in 10 ml of anhydrous 1,4-dioxane. The mixture was stirred for 20 minutes, then added to a solution of 2-amino-4,6-dichloro-triazine (164 mg, 1 mmol) in 30 ml of 1,4-dioxane at 0° C. for 1 hour. The reaction mixture was then warmed to room temperature. After completion of the reaction, 5 ml of water was added and ethyl acetate (20 ml) was used to extract the product. The organic layer was dried over sodium sulfate. The solvent was removed by rotovap to give 198 mg of 4-chloro-6-[2,2,2-trifluoro-1-phenyl-ethoxy]-[1,3,5]triazine-2-ylamine, yield 65%.

A microwave vial was charged with 4-chloro-6-[2,2,2-trifluoro-1-phenyl-ethoxy]-[1,3,5]triazine-2-ylamine (33 mg, 0.1 mmol), 4-borono-L-phenylalanine (31 mg, 0.15 mmol), 1 ml of actonitrile, and 0.7 ml of water. Aqueous sodium carbonate (0.3 ml, 1M) was added to above solution followed by 5 mol percent dichlorobis(triphenylphosphine)-palladium (II). The reaction vessel was sealed and heated to 150° C. for 5 minutes by microwave. After cooling, the reaction mixture was evaporated to dryness. The residue was dissolved in 2.5 ml of methanol, was then purified with Prep-LC to give 3.2 mg 2-amino-3-{4-[4-amino-6-(1-phenyl-2,2,2-trifluoroethoxy]-[1,3,5]triazin-2-yl]-phenyl)-propionic acid. $^{1}$H NMR (300 MHz, CD$_{3}$OD) δ 8.22 (d, J=8.20 Hz, 2H), 7.52 (m, 2H), 7.33 (m, 5H) 6.62 (m, 1H), 4.19 (t, 1H), 3.1-3.33 (m, 2H).

6.14. Synthesis of (S)-2-Amino-3-(5-(4-amino-6-((R)-1-(naphthalen-2-yl)ethylamino)-1,3,5-triazin-2-yl)pyridin-2-yl)propanoic acid

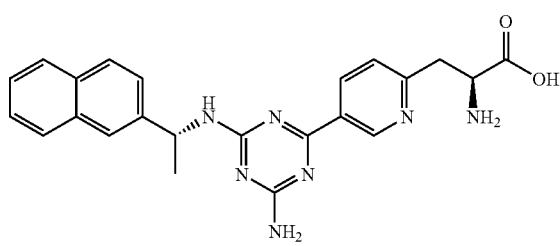

A microwave vial was charged with 6-chloro-N-[1-naphthalen-2yl-ethyl]-[1,3,5]triazine-2,4-diamine (30 mg, 0.1 mmol), 2-boc protected-amino-3-{5-[4,4,5,5,-tetramethyl-[1,3,2]dioxaborolan-2-yl)-pyridin2-yl-]-propionic acid (50 mg, 0.15 mmol) 1 ml of acetonitrile, and 0.7 ml of water. Aqueous sodium carbonate (0.3 ml; 1N) was added to the solution, followed by 5 mol percent dichlorobis(triphenylphosphine)-palladium(II). The reaction vessel was sealed and heated to 150° C. for 5 minutes by microwave. After cooling, the reaction mixture was evaporated to dryness. The residue was dissolved in 2.5 ml of methanol, and was then purified by Prep-LC to give 7 mg of boc protected 2-amino-3-{5-[4-amino-6-(1-naphthalen-2-yl-ethylamino)-[1,3,5]triazin-2-yl]-pyridin-2-yl}proionic acid.

The above product (7.0 mg) was dissolved in 0.1 ml of 10% TFA/DCM solution for 2 hours to provide 1.1 mg of 2-amino-3-{3-[4-amino-6-(1-naphthalen-2-yl-ethylamino)-[1,3,5]triazin-2-yl]-pyridin-2-yl}proionic acid. $^1$H NMR (300 MHz, $CD_3Cl$) δ 9.35 (d, 1H), 8.57 (m, 1H), 7.85 (m, 4H), 7.45 (m, 4H), 6.94 (s, 1H), 5.58 (m, 1H), 4.72 (m, 2H), 4.44 (m, 1H), 1.42 (d, 3H).

6.15. Synthesis of (S)-2-Amino-3-(3-(4-amino-6-((R)-1-(naphthalen-2-yl)ethylamino)-1,3,5-triazin-2-yl)-1H-pyrazol-1-yl)propanoic acid 6-Chloro-N-[1-naphthalen-2-yl-ethyl]-[1,3,5]triazine-2,4-diamine (30 mg, 0.1 mmol), 2-boc-protected amino-3-{3-[4,4,5,5,-tetramethyl-[1,3,2]dioxaborolan-2-yl)-pyrazol-1-yl]-propionic acid (50 mg, 0.15 mmol), 1 ml of acetonitrile, and 0.7 ml of water. Aqueous sodium carbonate (0.3 ml and 1N) was added to a microwave vial, followed by 5 mol percent of dichlorobis(triphenylphosphine)-palladium(II). The reaction vessel was sealed and heated to 150° C. for 5 minutes with microwave. After cooling, the reaction mixture was evaporated to dryness, the residue was dissolved in 2.5 ml of methanol, and then was purified with Prep-LC to give 6.8 mg of boc protected 2-amino-3-{3-[4-amino-6-(1-naphthalen-2-yl-ethylamino)[1,3,5]triazin-2-yl]-pyrazol-1-yl}proionic acid.

The above product (6.8 mg) was stirred in 0.1 ml 10% TFA/DCM solution for 2 hours to provide 3 mg of 2-amino-3-{3-[4-amino-6-(1-naphthalen-2-yl-ethylamino)-[1,3,5]triazin-2-yl]-pyrazol-1-yl}proionic acid. $^1$H NMR (300 MHz, $CD_3Cl$) δ 8.52 (s, 1H), 8.21 (s, 1H), 7.74 (m, 4H), 7.36 (m, 3H), 5.35 (m, 1H), 4.72 (m, 2H), 4.44 (m, 1H), 1.55 (d, 3H).

6.16. Synthesis of (S)-2-Amino-3-(4'-(3-(cyclopentyloxy)-4-methoxybenzylamino)biphenyl-4-yl)propanoic acid

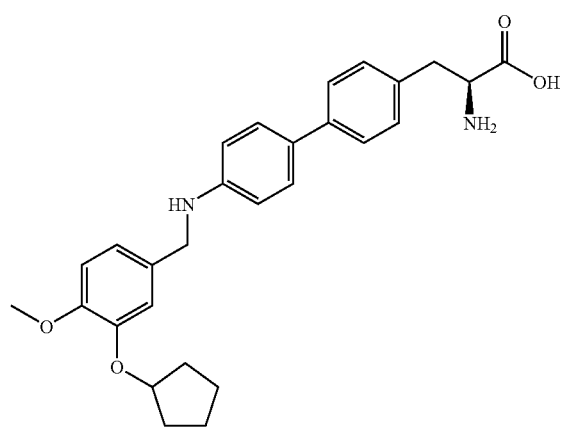

Sodium triacetoxyl-borohydride (470 mg, 2.21 mmol) was added to a solution of 4-bromo-phenylamine (252 mg, 1.47 mmol) and 3-cyclopentyloxy-4-methoxy-benzaldehyde (324 mg, 1.47 mmol) in 10 ml of 1,2-dichloroethane (DCE), 0.5 ml of HOAc was added. The mixture was stirred overnight at room temperature, followed by addition of 15 ml of DCE. The organic phase was washed with water and dried over sodium sulfate. The solvent was removed by rotovap to give 656 mg of crude (4-bromo-phenyl)-(3-cyclopentyloxy-4-methoxy-benzyl)-amine. It was used for next step without further purification.

An Emrys process vial (2-5 ml) for microwave was charged with (4-bromo-phenyl)-(3-cyclopentyloxy-4-methoxy-benzyl)-amine (84 mg, 0.22 mmol), 4-borono-L-phenylalanine (46 mg, 0.22 mmol) and 2 ml of acetonitrile. Aqueous sodium carbonate (2 ml, 1M) was added to above solution, followed by 5 mol percent of dichlorobis-(triphenylphosphine)-palladium(II). The reaction vessel was sealed and heated to 150° C. for 5 minutes by microwave. After cooling, the reaction mixture was evaporated to dryness. The residue was dissolved in 2.5 ml of methanol and purified with Prep-LC to give 5 mg of 2-amino-3-[4'-(3-cyclophentyloxy-4-methoxy-benzylamino)-biphenyl-4-yl]-propionic acid, yield 5%. $^1$H-NMR (400 MHz, DMSO-$d_6$): δ 1.46 (m, 2H), 1.62 (m, 4H), 3.01 (m, 2H), 3.64 (s, 3H), 4.14 (s, 3H), 4.66 (m, 1H), 6.61 (d, 2H), 6.81 (s, 2H), 6.88 (s, 1H), 7.18 (d, 2H), 7.31 (d, 2H), 7.44 (d, 2H), 7.60 (m, 1H), 8.19 (s, 3H).

6.17. Synthesis of (S)-2-Amino-3-(4-(6-(3-(cyclopentyloxy)-4-methoxybenzylamino)pyrimidin-4-yl)phenyl)propanoic acid

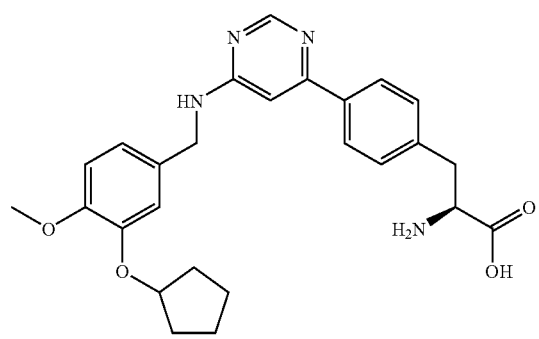

Sodium tiracetoxyl-borohydride (985 mg, 4.65 mmol) was added to a solution of 6-chloro-pyrimidin-4-ylamine (200 mg, 1.55 mmol) and 3-cyclopentyloxy-4-methoxybenzaldehyde (682 mg, 3.1 mmol) in 25 ml of DCE. 1 ml of HOAc was added, and the mixture was stirred overnight at 50° C., followed by addition of 25 ml of DCE. The organic phase was washed with water, and the product was purified with column (silica gel, hexane:EtOAc 5:1) to give 64 mg of (6-chloro-pyrimidin-4-yl)-(3-cyclopentyloxy-4-methoxy-benzyl)-amine, yield 12%.

An Emrys process vial (2-5 ml) for microwave was charged with (6-chloro-pyrimidin-4-yl)-(3-cyclopentyloxy-4-methoxy-benzyl)-amine (64 mg, 0.19 mmol), 4-borono-L-phenylalanine (40 mg, 0.19 mmol) and 2 ml of acetonitrile. Aqueous sodium carbonate (2 ml, 1M) was added to above solution followed by 5 mol percent of dichlorobis-(triphenylphosphine)-palladium(II). The reaction vessel was sealed and heated to 150° C. for 5 minutes with microwave. After cooling, the reaction mixture was evaporated to dryness. The residue was dissolved in 2.5 ml of methanol and purified with Prep-LC to give 5.3 mg of 2-amino-3-{4-[6-(3-cyclopentyloxy-4-methoxy-benzylamino)-pyrimidin-4-yl]-phenyl}-propionic acid, yield 6%. $^1$H-NMR (400 MHz, DMSO-$d_6$): δ 1.46 (m, 2H), 1.62 (m, 4H), 3.01 (m, 2H), 3.08 (m, 2H), 3.65 (s, 3H), 4.20 (m, 1H), 4.46 (d, 2H), 4.68 (m, 1H), 6.82 (t, 2H), 6.87 (d, 2H), 7.40 (d, 2H), 7.90 (s, 2H), 8.25 (s, 2H), 8.6 (s, 1H).

6.18. Synthesis of (S)-2-Amino-3-(4-(6-(3-(cyclopentyloxy)-4-methoxybenzylamino)pyrazin-2-yl)phenyl)propanoic acid

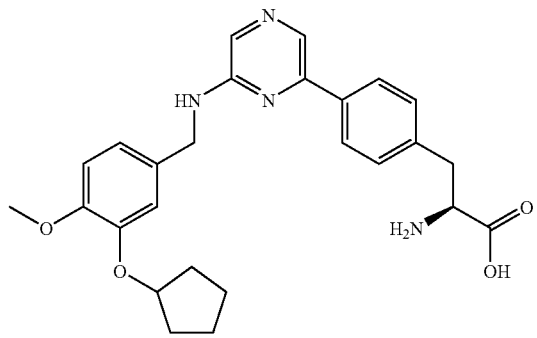

Sodium triacetoxyl-borohydride (1315 mg, 6.2 mmol) was added to a solution of 6-chloro-pyrazin-2-yl-amine (400 mg, 3.10 mmol) and 3-cyclopentyloxy-4-methoxybenzaldehyde (818 mg, 3.7 mmol) in 50 ml of DCE, 1 ml of HOAc was added and the mixture was stirred overnight at 50° C., followed by addition of another 50 ml of DCE. The organic phase was washed with water, and the product was purified with column (silica gel, hexane:EtOAc 6:1) to give 50 mg of (6-chloro-pyrazin-2-yl)-(3-cyclopentyloxy-4-methoxy-benzyl)-amine, yield 10%.

An Emrys process vial (2-5 ml) for microwave was charged with (6-chloro-pyrazin-2-yl)-(3-cyclopentyloxy-4-methoxy-benzyl)-amine (50 mg, 0.15 mmol), 4-borono-L-phenylalanine (31 mg, 0.15 mmol) and 2 ml of acetonitrile. Aqueous sodium carbonate (2 ml, 1M) was added to the solution followed by 5 mol percent of dichlorobis(triphenylphosphine)-palladium(II). The reaction vessel was sealed and heated to 150° C. for 5 minutes by microwave. After cooling, the reaction mixture was evaporated to dryness. The residue was dissolved in 2.5 ml of methanol, and the product was purified with Prep-LC to give 5.5 mg of 2-amino-3-{4-[6-(3-cyclopentyloxy-4-methoxy-benzylamino)-pyrazin-2-yl]-phenyl}-propionic acid, yield 6%. $^1$H-NMR (400 MHz, DMSO-$d_6$): δ 1.46 (m, 2H), 1.62 (m, 4H), 3.01 (m, 2H), 3.08 (m, 2H), 3.65 (s, 3H), 4.0 (m, 1H), 4.45 (d, 2H), 4.65 (m, 1H), 6.90 (s, 2H), 6.95 (s, 1H), 7.32 (d, 2H), 7.60 (t, 1H), 7.90 (s, 1H), 7.95 (d, 2H), 8.25 (s, 1H).

6.19. Synthesis of (S)-2-Amino-3-(4-(5-((4'-methylbiphenyl-2-yl)methylamino)pyrazin-2-yl)phenyl) propanoic acid

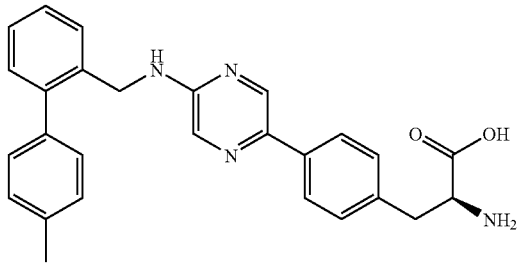

Sodium tiracetoxyl borohydride (215 mg, 1.02 mmol) was added to the solution of 4'-methyl-biphenyl-2-carbaldehyde and 5-bromo-pyrazin-2-ylamine in 5 ml of DCE, 0.1 ml of HOAc was added and the mixture was stirred overnight at room temperature, followed by addition of 5 ml of DCE. The organic phase was washed with water, and purified with column (silica gel, hexane:EtOAc 6:1) to give 100 mg of (5-bromo-pyrazin-2-yl)-(4'-methyl-biphenyl-2-ylmethyl)-amine, yield 55%.

An Emrys process vial (2-5 ml) for microwave was charged with (5-bromo-pyrazin-2-yl)-(4'-methyl-biphenyl-2-ylmethyl)-amine (25 mg, 0.071 mmol), 4-borono-L-phenylalanine (22 mg, 0.11 mmol) and 1 ml of acetonitrile. Aqueous sodium carbonate (1 ml, 1M) was added to the solution followed by 5 mol percent dichlorobis(triphenylphosphine)-palladium(II). The reaction vessel was sealed and heated to 150° C. for 5 minutes by microwave. After cooling, the reaction mixture was evaporated to dryness. The residue was dissolved in 2.5 ml of methanol, and the product was purified with Prep-LC to give 19 mg of 2-amino-3-{4-[6-(3-cyclopentyloxy-4-methoxy-benzylamino)-pyrazin-2-yl]-phenyl}-propionic acid, yield 63%. $^1$H-NMR (400 MHz, $CD_3OD$): δ 2.22 (s, 3H), 3.09 (m, 1H), 3.25 (m, 1H), 4.18 (t, 1H), 4.40 (s, 2H), 7.07 (d, 2H), 7.14 (m, 3H), 7.24 (m, 4H), 7.36 (m, 1H), 7.72 (d, 2H), 7.84 (s, 1H), 8.20 (d, 1H).

6.20. Synthesis of (2S)-2-Amino-3-(4-(6-(2,2,2-trifluoro-1-phenylethoxy)-pyrimidin-4-yl)phenyl)propanoic acid

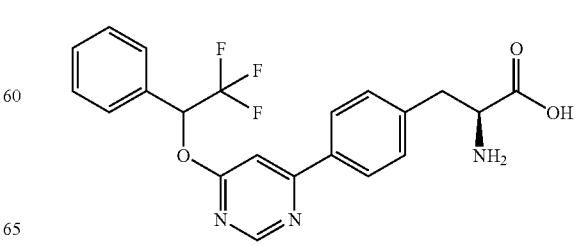

NaH (60%, 120 mg, 3.0 mmol) was added to a solution of 2,2,2-trifluoro-1-phenyl-ethanol (350 mg, 2.03 mmol) in 5 ml of THF. The mixture was stirred for 20 minutes at room temperature. 4,6-Dichloro-pyrimidine (300 mg, 2.03 mmol) was added and then the reaction mixture was heated at 70° C. for 1 hour. After cooling, the THF was evaporated to provide a residue, which was dissolved in 15 ml of EtOAc, and then washed with water, and dried over sodium sulfate. The solvent was removed by rotovap to give 550 mg of 4-chloro-6-(2,2,2-trifluoro-1-phenyl-ethoxy)-pyrimidine, yield 95%.

An Emrys process vial (2-5 ml) for microwave was charged with 4-chloro-6-(2,2,2-trifluoro-1-phenyl-ethoxy)-pyrimidine (30 mg, 0.1 μmol), 4-borono-L-phenylalanine (32 mg, 0.16 mmol), 1 ml of acetonitrile and 0.6 ml of water. Aqueous sodium carbonate (0.42 ml, 1M) was added to above solution followed by 10 mol percent of POPd$_2$ (dihydrogen di-μ-chlorodichlorobis(di-tert-butylphosphinito-κP)dipalladate. The reaction vessel was sealed and heated to 120° C. for 30 minutes by microwave. After cooling, the reaction mixture was evaporated to dryness. The residue was dissolved in 2.5 ml of methanol, and the product was purified with Prep-LC to give 4.8 mg of 2-amino-3-{4-[6-(2,2,2-trifluoro-1phenyl-ethoxy)-pyrimidin-4-yl]-phenyl}-propionic acid, yield 11%. $^1$H-NMR (400 MHz, CD$_3$OD): δ 3.20 (m, 1H), 3.40 (m, 1H), 4.25 (t, 1H), 6.82 (dd, 1H), 7.43 (m, 5H), 7.57 (s, 1H), 7.60 (m, 2H), 8.10 (d, 2H), 8.75 (s, 1H).

6.21. Synthesis of (2S)-2-Amino-3-(4-(6-(1-(3,4-difluorophenyl)-2,2,2-trifluoroethoxy)pyrimidin-4-yl)phenyl)propanoic acid

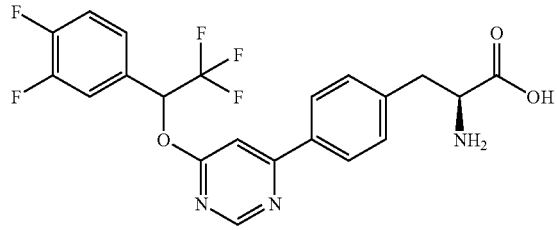

Tetrabutylammonium fluoride (TBAF: 0.1 ml, 1M) in THF was added to a solution of 3,4-difluoro-benzaldehyde (1.42 g, 10 mmol) and (trifluoromethyl)trimethylsilane (1.70 g, 12 mmol) in 10 ml THF at 0° C. The mixture was warmed up to room temperature and stirred for 4 hours. The reaction mixture was treated with 12 ml of 1M HCl and stirred overnight. The product was extracted with dichloromethane (3×20 ml), the organic layer was combined and passed through a pad of silica gel. The organic solvent was evaporated to give 1.9 g of 1-(3,4-difluoro-phenyl)-2,2,2-trifluoro-ethanol, yield 90%.

NaH (80 mg, 60%, 3.0 mmol) was added to a solution of 1-(3,4-Difluoro-phenyl)-2,2,2-trifluoro-ethanol (212 mg, 1 mmol) in 5 ml of THF, the mixture was stirred for 20 minutes at room temperature. 4,6-Dichloro-pyrimidine (149 mg, 1 mmol) was added and then the reaction mixture was heated at 70° C. for 1 hour. After cooling, THF was evaporated. The residue was dissolved in 15 ml of EtOAc, and then washed with water, dried over sodium sulfate. The solvent was removed by rotovap to give 230 mg of 4-chloro-6-[1-(3,4-difluoro-phenyl)-2,2,2-trifluoro-ethoxy]-pyrimidine, yield 70%.

An Emrys process vial (2-5 ml) for microwave was charged with 4-chloro-6-[1-(3,4-difluoro-phenyl)-2,2,2-trifluoro-ethoxy]-pyrimidine (33 mg, 0.1 mmol), 4-borono-L-phenylalanine (31 mg, 0.15 mmol), 1 ml of acetonitrile and 0.7 ml of water. Aqueous sodium carbonate (0.3 ml, 1M) was added to above solution followed by 5 mol % of dichlorobis(triphenylphosphine)-palladium(II). The reaction vessel was sealed and heated to 150° C. for 5 minutes by microwave. After cooling, the reaction mixture was evaporated to dryness. The residue was dissolved in 2.5 ml of methanol, then purified with Prep-LC to give 10 mg of 2-amino-3-(4-{6-[1-(3,4-difluoro-phenyl)-2,2,2-trifluoro-ethoxy]-pyridin-4-yl}-phenyl)-propionic acid, yield 21%. $^1$H-NMR (400 MHz, CD$_3$OD): δ 3.11 (m, 1H), 3.27 (m, 1H), 4.19 (dd, 1H), 6.78 (q, 1H), 7.26 (m, 2H), 7.35 (d, 3H), 7.49 (m, 2H), 8.02 (d, 2H), 8.66 (s, 1H).

6.22. Synthesis of (S)-2-Amino-3-(4-(5-(3-(cyclopentyloxy)-4-methoxybenzylamino)-pyrazin-2-yl)phenyl)propanoic acid

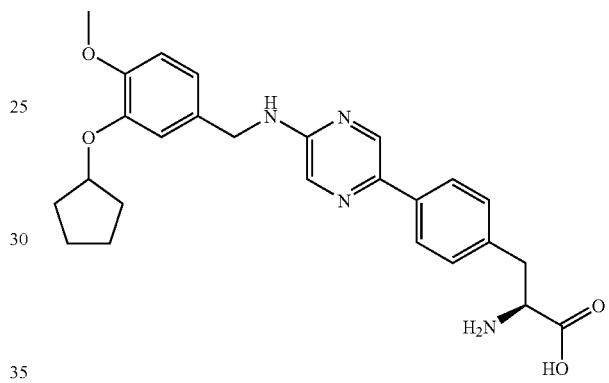

A mixture of 3-cyclopentyloxy-4-methoxy-benzaldehyde (417 mg, 1.895 mmol), 2-amino-5-bromopyrazine (300 mg, 1.724 mmol), sodium triacetoxyborohydride (1.5 eq) and glacial acetic acid (3 eq) in dichloromethane (10 ml) was stirred at room temperature overnight. Then the reaction mixture was diluted with ethyl acetate, and washed with water. The organic layer was dried over MgSO$_4$ and filtered. The filtrate was concentrated to give the crude product, which was purified by ISCO (SiO$_2$ flash column chromatography) (Hexane/ethyl acetate=100/0 to 3/2) to give about 400 mg of 6-bromo-pyrazin-2-yl)-(3-cyclopentyloxy-4-methoxy-benzyl)-amine. Yield: 61%.

To a 5 ml microwave vial, the above 6-bromo-pyrazin-2-yl)-(3-cyclopentyloxy-4-methoxy-benzyl)-amine (50 mg, 0.132 mmol), 4-borono-L-phenylalanine (30 mg, 0.144 mmol), Na$_2$CO$_3$ (31 mg, 0.288 mmol), acetonitrile (2 ml) and water (2 ml). Dichlorobis (triphenylphosphine)-palladium (5 mg, 0.007 mmol) was added. The vial was capped and stirred at 150° C. for 5 minutes under microwave radiation. The reaction mixture was cooled, filtered through a syringe filter and then separated by a reverse phase preparative-HPLC using YMC-Pack ODS 100×30 mm ID column (MeOH/H$_2$O/TFA solvent system). The pure fractions were concentrated in vacuum. The product was then suspended in 5 ml of water, frozen and lyophilized to give the title compound as a trifluoro salt (12 mg, 20%). $^1$H NMR (CD$_3$OD) δ 8.41 (s, 1H), 7.99 (s, 1H), 7.83 (d, J=9.0 Hz, 2H), 7.37 (d, J=6.0 Hz, 2H), 6.90-6.95 (m, 3H), 4.78 (m, 1H), 4.50 (s, 2H), 4.22-4.26 (m, 1H), 3.79 (s, 3H), 3.12-3.39 (m, 2H), 1.80-1.81 (m, 6H), 1.60 (m, 2H). M+1=463.

6.23. Synthesis of (S)-2-Amino-3-(4-(5-((3-(cyclopentyloxy)-4-methoxybenzyl)-(methyl)amino)pyrazin-2-yl)phenyl)propanoic acid

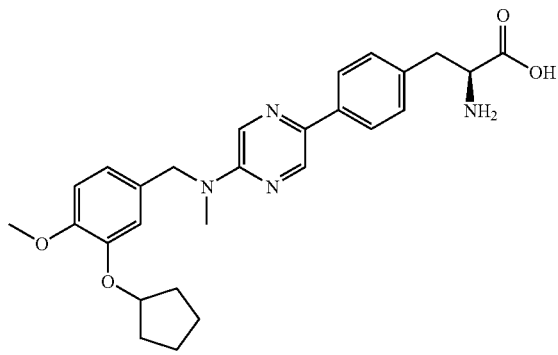

To a solution of (6-bromo-pyrazin-2-yl)-(3-cyclopentyloxy-4-methoxy-benzyl)-amine (70 mg, 0.185 mmol) in acetonitrile (10 ml) was added formaldehyde (18.5 mmol) and sodium cyanoborohydride (17 mg, 0.278 mmol). Then, concentrated aqueous HCl was added dropwise until the pH 2. The mixture was stirred for about 6 hours at room temperature. It was then diluted with ethyl acetate, washed with water (3×5 ml), dried over MgSO₄. The solvent was removed by vacuum to give 70 mg of crude product 5-(bromo-pyrazin-2-yl)-(3-cyclopentyloxy-4-methoxy-benzyl)-methyl-amine (95% crude yield), which was used in the next step without further purification.

The 5-(bromo-pyrazin-2-yl)-(3-cyclopentyloxy-4-methoxy-benzyl)-methyl-amine (37 mg, 0.094 mmol) was subjected to a Suzuki coupling reaction as described above to afford 6 mg of the title compound. Yield: 13%. $^1$H NMR (CD$_3$OD) δ 8.59 (s, 1H), 8.12 (s, 1H), 7.85 (d, 2H), 7.39 (d, 2H), 6.81-6.91 (m, 3H), 4.72 (m, 1H), 4.30 (m, 1H), 3.79 (s, 3H), 3.20-3.40 (m, 2H), 3.18 (s, 3H), 3.79 (s, 3H), 1.80 (m, 6H), 1.58 (m, 2H). M+1=477.

6.24. Synthesis of (S)-2-Amino-3-(4-(5-((1,3-dimethyl-1H-pyrazol-4-yl)methylamino)pyrazin-2-yl)phenyl)propanoic acid

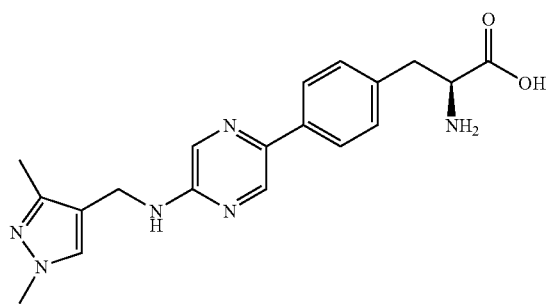

A mixture of 1,3-dimethyl-1H-pyrazole-4-carbaldehyde (142 mg, 1.145 mmol), 2-amino-5-bromopyrazine (200 mg, 1.149 mmol), borane trimethylamine complex (126 mg, 1.73 mmol) and glacial acetic acid (137 mg, 2.29 mmol) in anhydrous methonol (3 ml) was stirred at room temperature overnight. The reaction mixture was then diluted with ethyl acetate, washed with water, dried over MgSO₄ and filtered. The filtrate was concentrated to give 300 mg of (5-bromo-pyrazin-2-yl)-(1,3-dimethyl-1H-pyrazol-4-ylmethyl)amine as crude product, which was used for next step reaction without further purification. Crude yield: 93%.

The (5-bromo-pyrazin-2-yl)-(1,3-dimethyl-1H-pyrazol-4-ylmethyl)amine (40 mg, 0.142 mmol) was used in the Suzuki coupling reaction described above to afford 19 mg of the title compound. Yield: 36.5%. $^1$H NMR (CD$_3$OD) δ 8.48 (s, 1H), 8.05 (s, 1H), 7.87 (d, 2H), 7.39 (d, 2H), 6.10 (s, 1H), 4.81 (s, 2H), 4.30 (m, 1H), 3.83 (s, 3H), 3.11-3.38 (m, 2H), 2.10 (s, 3H). M+1=367.

6.25. Synthesis of (S)-2-Amino-3-(4-(4-amino-6-((S)-1-(naphthalen-2-yl)ethylamino)-1,3,5-triazin-2-yloxy)phenyl)propanoic acid

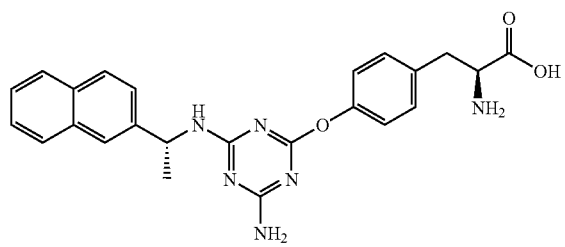

To a 250 ml flask, R-(+)-1-(2-naphthyl)ethylamine (400 mg, 2.424 mmol), 2-amino-4,6-dichloro triazine (373 mg, 2.181 mmol), anhydrous 1,4-dioxane (40 ml), and N,N-diisopropylethylamine (1 ml, 5.732 mmol) were added and heated to mild reflux for about 4 hours. The reaction was monitored carefully in order to avoid the formation of the disubstituted product. (It was observed that the longer the reaction, the more disubstituted product is formed). After 4 hours, the reaction mixture was cooled and the solvent was removed under reduced pressure. Water was added to the residue, and the solution was sonicated for 2-3 minutes. The solvent was then filtered, washed with water and dried to give 540 mg (83% crude yield) of the mono-chloride, 6-chloro-N-(1-naphthalen-2yl-ethyl)-[1,3,5]triazine-2,2-diamine, which was used for the next step reaction without further purification.

A mixture of 6-chloro-N-(1-naphthalen-2yl-ethyl)-[1,3,5]triazine-2,2-diamine (90 mg, 0.300 mmol), 2-tert-butoxycarbonylamino-3-(4-hydroxy-phenyl)-propionic acid tert-butyl ester (102 mg, 0.303 mmol) and potassium carbonate (82 mg, 0.594 mmol) in isopropanol (8 ml) was refluxed over night. The solvent was removed under reduced pressure and the residue was suspended in ethyl acetate. The solid was filtered and washed with ethyl acetate. The filtrate was concentrated and then redissolved in a mixture of methanol/water (90:10) and purified by a preparative-LC using a Sunfire C18 OBD 100×30 mm ID column (MeOH/H₂O/TFA solvent system). The pure fractions were combined and concentrated to give 50 mg of pure product, 3-{4-[4-amino-6-(1-naphthalen-2-yl-ethylamino)-[1,3,5]triazin-2yloxy]-phenyl}2-tert-butoxycarbonylamino-propionic acid tert-butyl ester, (28% yield).

The above product (50 mg, 0.083 mmol) was dissolved in trifluoro acetic acid/dichloromethane (8 ml/2 ml) and stirred at room temperature over night. The solvent was removed under reduced pressure. The residue was then redissolved in a mixture of methanol/water (90:10) and purified by a preparative-LC using a Sunfire C18 OBD 100×30 mm ID column (MeOH/H₂O/TFA solvent system). The pure fractions were combined and concentrated under reduced pressure to afford about 4 ml, which was frozen and lyophilized to give 4 mg of the title compound as a TFA salt (11% yield). $^1$H NMR (CD$_3$OD) δ 7.37-7.81 (m, 8H), 7.19 (m, 2H), 6.98 (m, 1H), 5.37 (m, 1H), 4.19 (m, 1H), 3.17-3.38 (m, 2H), 1.56 (m, 3H). M+1=445.

6.26. Synthesis of (S)-2-Amino-3-(4-(4-amino-6-((R)-1-(biphenyl-2-yl)-2,2,2-trifluoroethoxy)-1,3,5-triazin-2-yl)phenyl)propanoic acid

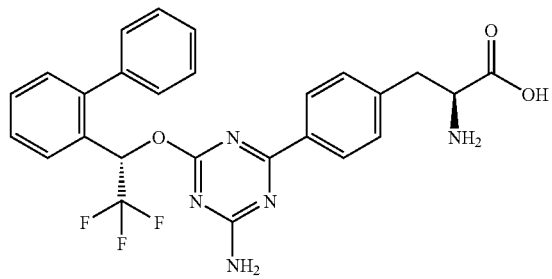

A mixture of 1-biphenyl-2-yl-2,2,2-trifluoro-ethanone (300 mg, 1.2 mmol), borane tetrahydrofuran complexes (1.2 ml, 1M in THF, 1.2 mmol) and S-2-methyl-CBS-oxazaborolidine (0.24 ml, 1M in toluene, 0.24 mmol) in THF (8 ml) was stirred at room temperature over night. Several drops of concentrated HCl were added and the mixture was stirred for 30 minutes. The product was purified by SiO$_2$ chromatography (hexane/ethyl acetate=100/0 to 3/1) to give 290 mg of 1-biphenyl-2-yl-2,2,2-trifluoro-ethanol (96% yield).

The above alcohol (290 mg, 1.151 mmol) was dissolved in anhydrous THF (10 ml). Sodium hydride (55 mg, 1.375 mmol) was added all at once, and the mixture was stirred at room temperature for 30 minutes. The solution was then transferred into a flask that contained a suspension of 2-amino-4,6-dichloro-triazine (190 mg, 1.152 mmol) in THF (20 ml). The mixture was stirred at room temperature overnight. Water was added and the mixture was then diluted with ethyl acetate. The organic layer was washed with water, dried over MgSO$_4$ and then concentrated to give 400 mg of crude product 2-amino-4-(1-biphenyl-2-yl-2,2,2-trifluoro-ethoxy-6-chloro-triazine.

The 2-amino-4-(1-biphenyl-2-yl-2,2,2-trifluoro-ethoxy-6-chloro-triazine (40 mg, 0.105 mmol) was subjected to the same Suzuki coupling reaction as described above to afford 5 mg of the title compound. Yield: 9.4%. $^1$H NMR (CD$_3$OD) δ 8.18 (d, 2H), 7.86 (m, 1H), 7.40-7.52 (m, 9H), 7.32 (m, 1H), 7.07 (m, 1H), 4.32 (m, 1H), 3.22-3.41 (m, 2H). M+1=510.

6.27. Synthesis of (2S)-2-Amino-3-(4-(4-amino-6-(1-(6,8-difluoronaphthalen-2-yl)ethylamino)-1,3,5-triazin-2-yl)phenyl)propanoic acid

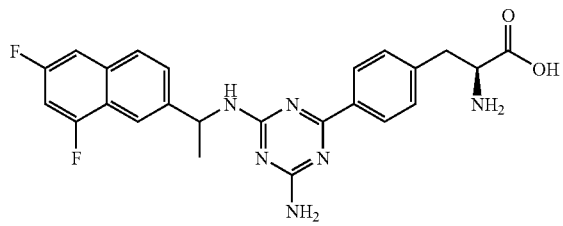

In a three-neck flask, copper iodine (CuI) (299 mg, 1.515 mmol) and lithium chloride (LiCl) (145 mg, 3.452 mmol) were added under nitrogen to anhydrous THF (60 ml). The mixture was stirred at room temperature until a pale yellow solution was obtained. After cooling to 0° C., methyl vinyl ketone and chlorotrimethylsilane were added, and the mixture was stirred until an orange color was observed (~20 min). After cooling to about –40° C., a solution of 3,5-difluorophenylmagnesium bromide (27.65 ml, 13.8 mmol) in THF (0.5M) was slowly added. The reaction mixture was stirred at about –40° C. for 0.5 hours, then the cold bath was removed and the temperature was allowed to rise slowly to room temperature. The solvent was evaporated and the residue was extracted with hexane (4×20 ml). The collected extractions were washed with cold 10% aqueous NaHCO$_3$ and dried over Na$_2$SO$_4$. The solvent was evaporated at reduced pressure to afford 3,5-difluorophenyl-1-trimethylsilyloxyalkene (2.03 g, 7.929 mmol, 57% crude yield), which was used in the successive reaction without further purification.

Powered calcium carbonate (3.806 g, 38.06 mmol) and ethyl vinyl ether (2.184 g, 30.329 mmol) were added to a solution of ceric ammonium nitrate (10.430 g, 19.033 mmol) in methanol (40 ml) under nitrogen atmosphere. To the resulting suspension was added a solution of above made 3,5-difluorophenyl-1-trimethylsilyloxyalkene (2.03 g, 7.929 mmol) in ethyl vinyl (6 ml, 4.518 g, 62.75 mmol) dropwise under vigorous stirring, and the mixture was stirred at room temperature overnight. The solid was filtered through a celite layer, and the filtrate was concentrated to one-fourth of its initial volume. The resulting thick mixture was slowly poured, under vigorous stirring, into 1:1 v/v diethyl ether-10% aqueous NaHCO$_3$. The precipitate was filtered off, the ethereal solution was separated, and the solvent was evaporated at reduced pressure to give clear liquid. The solution of resulting liquid (a mixture of acyclic and cyclic acetates) in methanol (4 ml) was added dropwise to a suspension of dichlorodicyanobenzoquinone (1.77 g, 7.797 mmol) in 80% aqueous sulfuric acid at 0° C. After the addition was complete, the ice bath was removed and stirring was continued for 30 minutes. The mixture was poured into ice water; and the resulting brown precipitate was filtered and dissolved in acetone. Silica gel was added to make a plug, and the crude product was purified by chromatography (hexane/ethyl acetate=100/0 to 3/1) to give 760 mg of 1-(5,7-difluoro-naphthalen-2-yl)-ethanone (48% in two-step yield) as a light yellow solid.

The above ketone (760 mg, 3.689 mmol) was dissolved in methanol (40 ml). Then, ammonium acetate (2.841 g, 36.896 mmol), sodium cyanoborohydride (232 mg, 3.389 mmol) and molecular sieves (3 Å, 7.6 g) were added. The mixture was stirred at room temperature for two days. The solid was filtered and the filtrate was concentrated. The residue was dissolved in water and concentrated aqueous HCl was added dropwise until the pH≈2. The mixture was then extracted with ethyl acetate to remove the unfinished ketone and other by-products. The water layer was basified to pH 10 with aqueous sodium hydroxide (1M), and was extracted with dichloromethane and the organic layers were combined, dried over magnesium sulfate and concentrated to afford 290 mg of 1-(5,7-difluoro-naphthalen-2-yl)-ethylamine (38% yield).

The fresh made amine (290 mg, 1.401 mmol) was added directly to a suspension of 2-amino-4,6-dichloro triazine (277 mg, 1.678 mmol) in anhydrous 1,4-dioxane (60 ml), and followed by addition of N,N-diisopropylethylamine (1 ml, 5.732 mmol). The mixture was heated to mild reflux for about 3 hours. The reaction mixture was then cooled, and the solvent was removed under reduced pressure. To the residue was added water and the mixture was sonicated for 2-3 minutes.

The resulting solid was filtered and washed with water and dried to give 395 mg (60% crude yield) of 6-chloro-N-[1-(6, 8-difluoronaphthalen-2-yl-ethyl]-[1,3,5]triazine-2,4-diamine, which was used for the next step reaction directly without further purification.

The above made mono-chloride (48 mg, 0.144 mmol) was subjected to the same Suzuki coupling reaction as described above to afford 12 mg of the title product. Yield: 17.9%. $^1$H NMR (CD$_3$OD) δ 8.14-8.22 (m, 2H), 8.05 (m, 1H), 7.92 (m, 1H), 7.63 (m, 1H), 7.32-7.51 (m, 3H), 7.11 (m, 1H), 5.48 (m, 1H), 4.13 (m, 1H), 3.13-3.41 (m, 2H), 1.66 (d, 3H). M+1=465.

6.28. Synthesis of (2S)-2-Amino-3-(4-(4-amino-6-(2, 2,2-trifluoro-1-(3'-methylbiphenyl-2-yl)ethoxy)-1,3, 5-triazin-2-yl)phenyl)propanoic acid

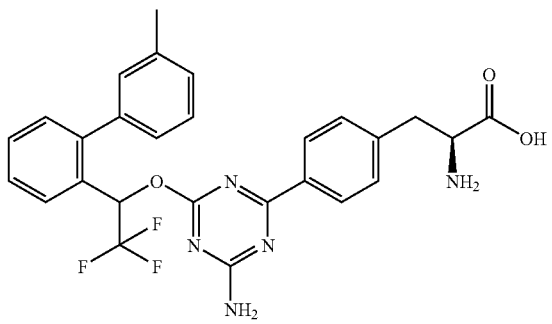

To a mixture of 3'-methyl-1-biphenyl-2-carbaldehyde (500 mg, 2.55 mmol) and trifluoromethyl trimethylsilane (435 mg, 3.061 mmol) in THF (3 ml) was added tetrabutyl ammonium fluoride (13 mg, 0.05 mmol) at 0° C. The temperature was allowed to warm to room temperature. The mixture was stirred for 5 hours at room temperature, then diluted with ethyl acetate, washed with water and brine and dried by MgSO$_4$. The solvent was removed under reduced pressure to give 660 mg (97% crude yield) of 2,2,2-trifluoro-1-(3'-methyl-biphenyl-2-yl)-ethanol as crude product, which was used for next step without further purification.

The above-made alcohol (660 mg, 2.481 mmol) was dissolved in anhydrous 1,4-dioxane (10 ml). Sodium hydride (119 mg, 60% in mineral oil, 2.975 mmol) was added all at once and the mixture was stirred at room temperature for 30 minutes. The solution was transferred into a flask containing a suspension of 2-amino-4,6-dichloro-triazine (491 mg, 2.976 mmol) in 1,4-dioxane (70 ml). The mixture was stirred at room temperature for 6 hours. The solvent was removed, and the residue was suspended in ethyl acetate, which was washed with water, dried over MgSO$_4$ and then concentrated to give 790 mg of crude product, which contained about 57% of the desired product 2-amino-4-(1-(3'-methyl-biphenyl-2-yl-2,2,2-trifluoro-ethoxy-6-chloro-triazine and about 43% byproduct (the bisubstituted product). The crude product was used without further purification.

The 2-amino-4-(1-(3'-methyl-biphenyl-2-yl-2,2,2-trifluoro-ethoxy-6-chloro-triazine (98 mg, 57% purity, 0.142 mmol) was used to run the same Suzuki coupling reaction as described above to afford 9 mg of the title compound. Yield: 12.0%. $^1$H NMR (CD$_3$OD) δ 8.09 (m, 2H), 7.85 (m, 1H), 7.50 (m, 2H), 7.28-7.43 (m, 5H), 7.17-7.26 (m, 2H), 7.18 (m, 1H), 3.85 (m, 1H), 3.08-3.44 (m, 2H), 2.33 (s, 3H). M+1=524.

6.29. Synthesis of (S)-2-Amino-3-(4-(5-(3,4-dimethoxyphenylcarbamoyl)-pyrazin-2-yl)phenyl) propanoic acid

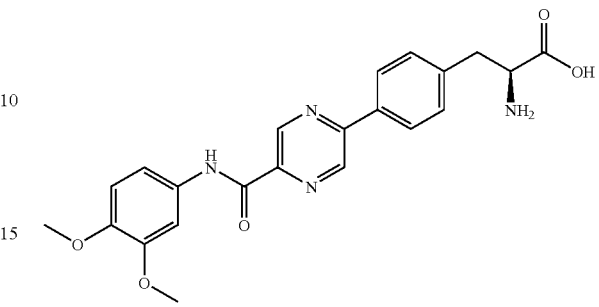

To a mixture of 3,4-dimethoxy phenylamine (0.306 g, 2 mmol) and triethylamine (0.557 ml, 4 mmol) in dichloromethane (20 ml) was added 5-chloro-pyrazine-2-carbonyl chloride (0.354 g, 2 mmol) at 0-5° C. The mixture was allowed to stir at room temperature for 3 hours. The mixture was diluted with methylene chloride (20 ml), washed with saturated NaHCO$_3$ (20 ml), brine (20 ml), dried (anhyd. Na$_2$SO$_4$) and concentrated to get 0.42 g of crude 5-chloro-pyrazine-2 carboxylic acid (3,4-dimethoxy-phenyl)-amide, which was directly used in the next reaction.

5-Chloro-pyrazine-2 carboxylic acid (3,4-dimethoxy-phenyl)-amide (0.18 g, 0.61 mmol), L-p-borono phenylalanine (0.146 g, 0.70 mmol), CH$_3$CN (2.5 ml), H$_2$O (2.5 ml), Na$_2$CO$_3$ (0.129 g, 1.22 mmol) were combined in a microwave vial. The mixture was sealed and kept at 150° C. for 5 minutes. The mixture was filtered and concentrated. The residue was dissolved in methanol/water (1:1) and purified by preparative HPLC, using MeOH/H$_2$O/TFA as solvent system to afford 2-amino-3-{4-[5-(3,4-dimethoxy-phenylcarbornyl)-pyrazin-2yl]-phenyl}-propionic acid as a TFA salt (HPLC: Method A, Retention time=2.846 min, LCMS M+1 423). $^1$H NMR (400 MHz, DMSO-d$_6$) δ 3.10-3.30 (m, 2H), 3.72 (d, 6H), 4.05 (m, 1H), 7.42-7.62 (m, 4H), 8.22 (m, 3H), 9.30 (m, 2H).

6.30. Synthesis of (S)-2-Amino-3-(4-(2-amino-6-(4-(2-(trifluoromethyl)phenyl)-piperidin-1-yl)pyrimidin-4-yl)phenyl)propanoic acid

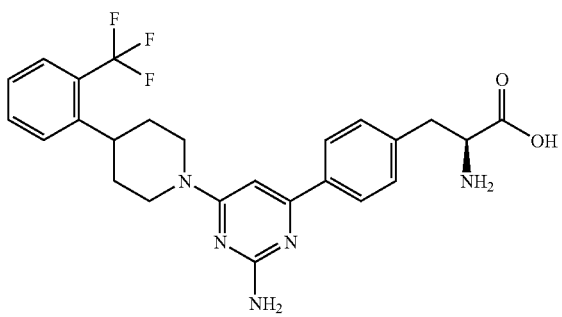

2-Amino 4,6-dichloro pyrimidine (0.164 g, 1 mmol), 4-(2-trifluoromethyl-phenyl)-piperidine hydrochloride (0.266 g, 1 mmol), and cesium carbonate (0.684 g, 2.1 mmol) were dissolved in a mixture of 1,4-dioxane (5 ml) and H$_2$O (5 ml) in a 20 ml microwave vial. The mixture was stirred at 210° C. for 20 minutes in a microwave reactor. Solvent was removed and the residue was dissolved in 5% methanol in CH$_2$Cl$_2$ (20 ml), dried over Na$_2$SO$_4$ and concentrated to get the crude intermediate, 4-chloro-6-[4-(2-trifluoromethyl-phenyl)-piperidin-1-yl]-pyrimidin-2-ylamine (0.42 g) which was directly used in the following step.

The crude intermediate (0.42 g), L-p-borono-phenylalanine (0.209 g, 1 mmol), sodium carbonate (0.210 g, 2 mmol), and dichlorobis (triphenylphosphine)-palladium(II) (35 mg, 0.05 mmol) were dissolved in a mixture of MeCN (2.5 ml) and H$_2$O (2.5 ml) in a 10 ml microwave vial. The vial was sealed and stirred in a microwave reactor at 150° C. for 6 minutes. The mixture was filtered, and the filtrate was concentrated. The residue was dissolved in MeOH and H$_2$O (1:1) and purified by preparative HPLC using MeOH/H$_2$O/TFA as the solvent system to afford 2-amino-3-(4-{4-(2-trifluoromethyl-phenyl)-piperidine-1-yl]-pyrimidin-4yl}-phenyl)-propionic acid as a TFA salt. HPLC: Method A, Retention time=3.203 min. LCMS M+1 486. $^1$H NMR (400 MHz, CD$_3$OD) δ 1.80-2.20 (m, 5H), 3.0-3.16 (m, 2H), 3.22-3.42 (m, 2H), 4.22 (t, 1H), 4.42-4.54 (m, 1H), 5.22-5.34 (m, 1H), 6.80 (s, 1H), 7.40 (t, 1H), 7.50-7.60 (m, 4H), 7.68 (d, 1H), 7.82 (d, 2H).

6.31. Synthesis of (S)-2-Amino-3-(4-(2-amino-6-((R)-1-(naphthalen-2-yl)ethylamino)pyrimidin-4-yl)phenyl)propanoic acid

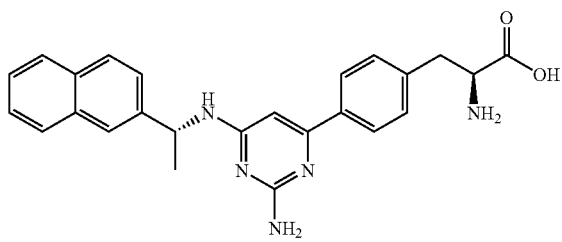

2-Amino 4,6-dichloro pyrimidine (0.164 g, 1 mmol), (R)-(+)-1-(2-naphthyl)-ethylamine (0.171 g, 1 mmol), and cesium carbonate (0.358 g, 1.1 mmol) were dissolved in a mixture of 1,4-dioxane (4 ml) and H$_2$O (4 ml) in a 20 ml microwave vial. The vial was sealed and stirred at 210° C. for 20 minutes in a microwave reactor. Solvent was removed and the residue was dissolved in CH$_2$Cl$_2$ (50 ml), washed with water (20 ml), brine (20 ml), dried (Na$_2$SO$_4$) and concentrated to afford the crude intermediate, 6-chloro-N-4-(naphthalene-2-yl-ethyl)-pyrimidine-2,4-diamine (0.270 g) which was directly used in the following step.

The crude intermediate (0.27 g), L-p-borono-phenylalanine (0.210 g, 1 mmol), sodium carbonate (0.210 g, 2 mmol), and dichlorobis(triphenylphosphine)-palladium(II) (25 mg, 0.036 mmol) were dissolved in a mixture of MeCN (2.5 ml) and H$_2$O (2.5 ml) in a microwave vial. The vial was sealed and stirred in the microwave reactor at 150° C. for 6 minutes. The mixture was filtered and the filtrate was concentrated. The residue was dissolved in MeOH and H$_2$O (1:1) and purified by preparative HPLC using MeOH/H$_2$O/TFA as the solvent system to afford 2 amino-3-{4-[2-amino-6-(1-naphthalen-2yl-ethylamino)-pyrimidin-4-yl]-phenyl}-propionic acid as a TFA salt. HPLC: Method A, Retention time=3.276 min. LCMS M+1 428. $^1$H NMR (400 MHz, CD$_3$OD) δ 1.68 (d, 3H), 3.22-3.40 (m, 2H), 4.30 (t, 1H), 5.60 (q, 1H), 6.42 (s, 1H), 7.42-7.54 (m, 5H), 7.72 (m, 2H), 7.82-7.84 (m, 4H).

6.32. Synthesis of (S)-2-Amino-3-(4-(2-amino-6-(methyl((R)-1-(naphthalen-2-yl)ethyl)amino)pyrimidin-4-yl)phenyl)propanoic acid

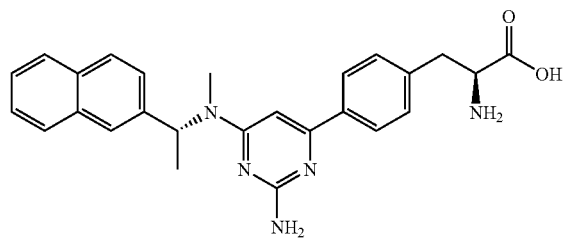

2-Amino 4,6-dichloro pyrimidine (0.327 g, 2 mmol), methyl-(1-naphthalen-2yl-ethyl)-amine (0.360 g, 2 mmol), and cesium carbonate (0.717 g, 2.2 mmol) were dissolved in a mixture of 1,4-dioxane (7.5 ml) and H$_2$O (7.5 ml) in a 20 ml microwave vial. The vial was sealed and stirred at 210° C. for 20 minutes in a microwave reactor. Solvent was removed and the residue was dissolved in CH$_2$Cl$_2$ (50 ml), washed with water (20 ml), brine (20 ml) dried (Na$_2$SO$_4$) and concentrated to get the crude intermediate, 6-chloro-N-4-methyl-N-4-(1-napthalen-2-yl-ethyl)-pyrimidine-2,4-diamine (0.600 g), which was directly used in the following step.

The crude intermediate (0.30 g), L-p-borono-phenylalanine (0.210 g, 1 mmol), sodium carbonate (0.210 g, 2 mmol), and dichlorobis(triphenylphosphine)-palladium(II) (25 mg, 0.036 mmol) were dissolved in a mixture of MeCN (2.5 ml) and H$_2$O (2.5 ml) in a microwave vial. The vial was sealed and stirred in the microwave reactor at 150° C. for 6 minutes. The mixture was filtered and the filtrate was concentrated. The residue was dissolved in MeOH and H$_2$O (1:1) and purified by preparative HPLC using MeOH/H$_2$O/TFA as the solvent system to afford 2-amino-3-(4-{2-amino-6-[methyl-(1-naphthalen-2yl-ethyl)amino]-pyrimidin-4yl}-phenyl)-propionic acid as a TFA salt (HPLC: Method C, Retention time=2.945 min, LCMS M+1 442) $^1$H NMR (400 MHz, CD$_3$OD) δ 1.70 (m, 3H), 2.92 (s, 3H), 3.22-3.42 (m, 2H), 4.28 (m, 1H), 6.60 (s, 1H), 6.72 (m, 1H), 7.40-7.92 (m, 11H).

6.33. Synthesis of (S)-2-Amino-3-(4-(2-amino-6-((S)-2,2,2-trifluoro-1-(6-methoxynaphthalen-2-yl)ethoxy)pyrimidin-4-yl)phenyl)propanoic acid

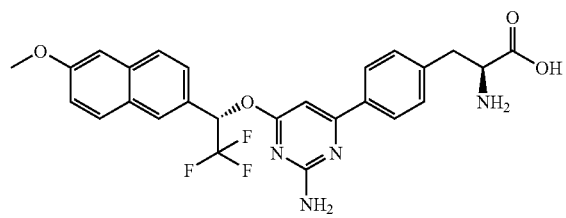

2-Amino 4,6-dichloro pyrimidine (0.096 g, 0.6 mmol), 2,2,2-trifluoro-1-(6-methoxy-naphthalen-2-yl)-ethanol (0.140 g, 0.55 mmol), and NaH (96 mg, 0.60 mmol) were added to anhydrous dioxane (20 ml) under a nitrogen atmosphere. The reaction was stirred at 80° C. for 12 hours, cooled to room temperature, and quenched with water (0.2 ml). The reaction mixture was concentrated, and the residue dissolved in CH$_2$Cl$_2$ (50 ml), washed with water (20 ml), brine (20 ml) dried (Na$_2$SO$_4$) and concentrated to afford the crude intermediate, 4-chloro-6-[2,2,2-trifluoro-1-(6-methoxy-naphthalene-2-yl)-ethoxy]-pyrimidin-2-ylamine (0.22 g) which was directly used in the following step.

The crude intermediate (0.22 g), L-p-borono-phenylalanine (0.126 g, 0.6 mmol), sodium carbonate (0.126 g, 1.2 mmol), and dichlorobis(triphenylphosphine)-palladium(II) (15 mg, 0.021 mmol) were dissolved in a mixture of MeCN (2.0 ml) and H$_2$O (2.0 ml) in a microwave vial. The vial was sealed and stirred in the microwave reactor at 150° C. for 6 minutes. The mixture was filtered and the filtrate was concentrated. The residue was dissolved in MeOH and H$_2$O (1:1) and purified by preparative HPLC using MeOH/H$_2$O/TFA as the solvent system to afford 2-amino-3-(4-{2-amino-6-[2,2,2-trifluoro-1-(6-methoxy-naphthalen-2-yl)-ethoxy]-pyrimidin-4-yl}-phenyl)-propionic acid as a TFA salt (HPLC: Method C, Retention time=3.190 min. LCMS M+1 513. $^1$H NMR (400 MHz, CD$_3$OD) δ 3.22-3.42 (m, 2H), 3.86 (s, 3H), 4.32 (1H), 6.88 (m, 1H), 6.92 (1H), 7.20 (dd, 1H), 7.26 (s, 1H), 7.50 (d, 2H), 7.63 (d, 1H), 7.80-7.90 (m, 4H), 8.05 (s, 1H).

6.34. Synthesis of (S)-2-Amino-3-(4-(5-(biphenyl-4-ylmethylamino)pyrazin-2-yl)phenyl)propanoic acid

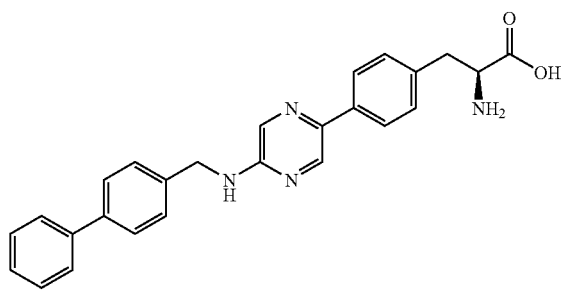

4-Phenylbenzaldehyde (0.3 g, 1.65 mmol) and 2-amino-5-bromopyrazine (0.24 g, 1.37 mmol) were treated with Na(OAc)$_3$BH (0.44 g, 2.06 mmol) in dichloroethane (7.0 mls) and acetic acid (0.25 mls) for 18 hours at room temperature. The mixture was diluted with dichloromethane, washed with 1.0 N NaOH, washed with brine, dried over MgSO$_4$, and concentrated. Chromatography (SiO$_2$, EtOAc:Hex, 1:1) gave 0.18 g of N-(biphenyl-4-ylmethyl)-5-bromopyrazin-2-amine.

N-(biphenyl-4-ylmethyl)-5-bromopyrazin-2-amine (60 mg, 0.176 mmol), L-p-boronophenylalanine (37 mg, 0.176 mmol), palladiumtriphenylphosphine dichloride (3.6 mg, 0.0052 mmol), Na$_2$CO$_3$ (37 mg, 0.353 mmol), acetonitrile (1.25 mls) and water (1.25 mls) were heated in a microwave reactor at 150° C. for 5 minutes. The mixture was concentrated, dissolved in 1.0 N HCl, washed twice with ether, concentrated and purified by preprative HPLC to give 41 mgs of the title compound. M+1=425; $^1$H NMR (CD$_3$OD) δ 8.42 (s, 1H), 8.05 (s, 1H), 7.92 (d, 2H), 7.58 (d, 4H), 7.40 (m, 7H), 4.60 (s, 2H), 4.25 (m, 1H), 3.40 (m, 1H), 3.20 (m, 1H).

6.35. Synthesis of (S)-2-Amino-3-(4-(5-(naphthalen-2-ylmethylamino)pyrazin-2-yl)phenyl)propanoic acid

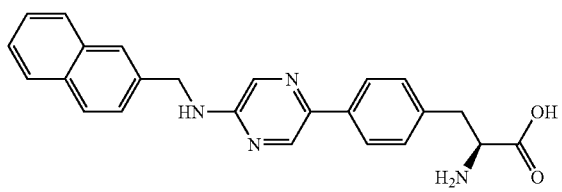

2-Napthaldehyde (0.6 g, 3.84 mmol) and 2-amino-5-bromopyrazine (0.56 g, 3.201 mmol) were treated with Na(OAc)$_3$BH (1.02 g, 4.802 mmol) in dichloroethane (15.0 mls) and acetic acid (0.5 mls) for 18 hours at room temperature. The mixture was diluted with dichloromethane, washed with 1.0 N NaOH, washed with brine, dried over MgSO$_4$, and concentrated. Chromatography (SiO$_2$, EtOAc:Hex, 1:1) gave 0.49 g 5-bromo-N-(naphthalen-2-ylmethyl)pyrazin-2-amine.

5-Bromo-N-(naphthalen-2-ylmethyl)pyrazin-2-amine (0.2 g, 0.637 mmol), L-p-boronophenylalanine (0.13 g, 0.637 mmol), palladiumtriphenylphosphine dichloride (13 mg, 0.019 mmol), Na$_2$CO$_3$ (0.13 g, 1.27 mmol), acetonitrile (5 mls) and water (5 mls) were heated in a microwave reactor at 150° C. for 5 minutes. The mixture was concentrated, dissolved in 1.0 N HCl, washed twice with ether, concentrated, dissolved in methanol, filtered and concentrated to yield 0.12 g of the captioned compound. M+1=399; $^1$H NMR (CD$_3$OD) δ 8.51 (s, 1H), 8.37 (s, 1H), 7.90 (m, 6H), 7.50 (m, 5H), 4.85 (s, 2H), 4.30 (t, 1H), 3.38 (m, 1H), 3.22 (m, 1H).

6.36. Synthesis of (S)-2-(Tert-butoxycarbonylamino)-3-(4-(5-(naphthalen-2-ylmethylamino)pyrazin-2-yl)phenyl)propanoic acid

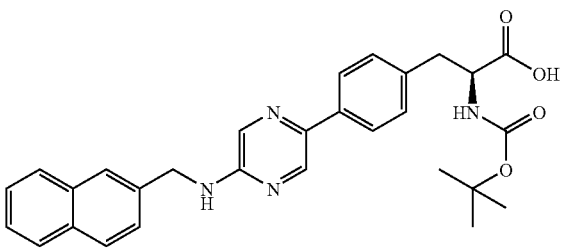

(S)-2-Amino-3-(4-(5-(naphthalen-2-ylmethylamino)pyrazin-2-yl)phenyl)propanoic acid (0.15 g, 0.345 mmol) was treated with triethylamine (87 mg, 0.862 mmol), and boc-anhydride (84 mg, 0.379) in dioxane (3 ml) and H$_2$O (3 ml) at 0° C. The mixture was warmed to room temperature and stirred overnight. The mixture was concentrated, and partitioned between EtOAc and H$_2$O. The aqueous phase was acidified to pH=1 with 1.0 N HCl and extracted with EtOAc. The organics were combined, washed with brine, dried over MgSO$_4$, and concentrated to yield 48 mg of the captioned compound.

6.37. Synthesis of (S)-2-Morpholinoethyl 2-amino-3-(4-(5-(naphthalen-2-ylmethylamino)pyrazin-2-yl)phenyl)propanoate

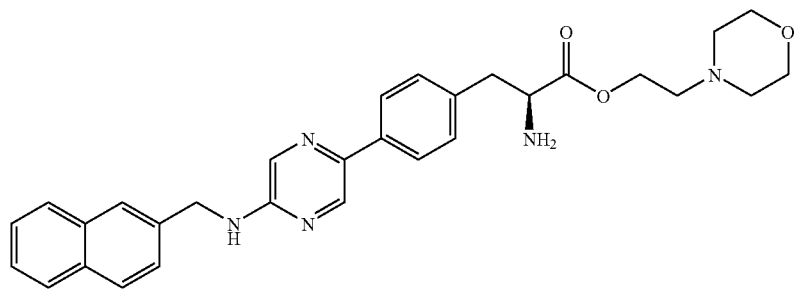

(S)-2-(Tert-butoxycarbonylamino)-3-(4-(5-(naphthalen-2-ylmethylamino)pyrazin-2-yl)phenyl)propanoic acid (48 mg, 0.090 mmol), 4-(2-hydroxyethyl)morpholine (12 mg, 0.090 mmol), triethylamine (18 mg, 0.180 mmol), and benzotriazole-1-yloxytris(dimethylamino)-phosphonium hexafluorophosphate (BOP, 18 mg, 0.090 mmol), in dichloromethane (3.0 ml) were stirred at room temperature for 5 hours. Additional triethylamine (18 mg, 0.180 mmol) and BOP (18 mg, 0.090 mmol) were added, and the mixture was stirred overnight. The mixture was concentrated and purified via prep HPLC to give 2 mg of the captioned compound.

6.38. Synthesis of (2S)-2-Amino-3-(4-(2-amino-6-(2,2,2-trifluoro-1-(3'-fluorobiphenyl-4-yl)ethoxy)pyrimidin-4-yl)phenyl)propanoic acid

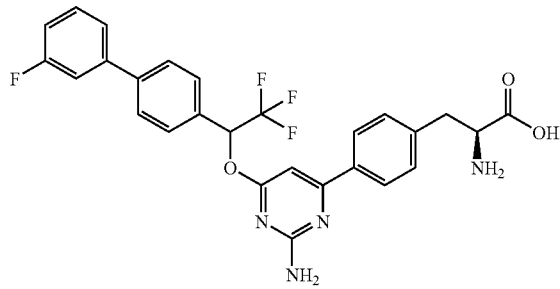

To 4'-bromo-2,2,2-trifluoroacetophenone (5.0 g, 19.76 mmol) in THF (50 mls) at 0° C. was added NaBH$_4$ (1.5 g, 39.52 mmol). The mixture was warmed to room temperature and stirred for 1 hour. The reaction was complete by TLC (CH$_2$Cl$_2$). The mixture was quenched with H$_2$O, rotary evaporated to remove most of the THF, and extracted 2 times with CH$_2$Cl$_2$. The organics were combined, washed with brine, concentrated to a small volume and filtered through a plug of silica gel. The silica was washed with CH$_2$Cl$_2$ to elute the product, and the resulting solution was concentrated to give 4.65 g of 1-(4-bromophenyl)-2,2,2-trifluoroethanol. Yield 92%.

To Pd(PPh$_3$)$_4$ (2.1 g, 1.823 mmol) was added 3-fluorophenylmagnesium bromide (55 mls, 1.0 M in THF, 55 mmol) at 0° C. over 15 minutes. The ice bath was removed and the mixture was stirred for 30 minutes. 1-(4-Bromophenyl)-2,2,2-trifluoroethanol (4.65 g, 18.23 mmol) in THF (50 mls) was added over 10 minutes. The mixture was heated to reflux for 3 hours and was shown complete by LC (Sunfire column, TFA). The mixture was cooled, quenched with H$_2$O, rotary evaporated to remove most of the THF, and extracted 3 times with CH$_2$Cl$_2$. The organics were combined washed with brine, dried over MgSO$_4$, and concentrated. Chromatography (SiO$_2$, CH$_2$Cl$_2$) gave 4.64 g of 2,2,2-trifluoro-1-(3'-fluorobiphenyl-4-yl)ethanol. Yield 94%.

To 2,2,2-trifluoro-1-(3'-fluorobiphenyl-4-yl)ethanol (1.4 g, 5.18 mmol) in THF (50 mls) at 0° C. was added NaH (60% in mineral oil, 0.31 g, 7.77 mmol). The ice bath was removed and the mixture was stirred for 30 minutes. 2-Amino-4,6-dichloropyrimidine (1.0 g, 6.22 mmol) in THF (25 mls) was added at once. The mixture was heated to 50° C. for 5 hours. The reaction was complete by LCMS (Sunfire, TFA). The mixture was cooled, quenched with brine, and extracted 3 times with CH$_2$Cl$_2$. The organics were combined, washed with brine, dried over MgSO$_4$, and concentrated. Chromatography (SiO$_2$, CH$_2$Cl$_2$) afforded 1.48 g of 4-chloro-6-(2,2,2-trifluoro-1-(3'-fluorobiphenyl-4-yl)ethoxy)pyrimidin-2-amine. Yield 73%.

4-Chloro-6-(2,2,2-trifluoro-1-(3'-fluorobiphenyl-4-yl)ethoxy)pyrimidin-2-amine (0.75 g, 1.89 mmol), L-p-boronophenylalanine (0.47 g, 2.26 mmol), Pd(PPh$_3$)$_2$Cl$_2$ (79 mgs, 0.113 mmol), Na$_2$CO$_3$ (0.44 g, 4.15 mmol), acetonitrile (10 mls), and H$_2$O (10 mls) were combined in a 20 ml microwave reactor and heated in the microwave at 150° C. for 7 minutes. The reaction was complete by LCMS (Sunfire, neutral). The mixture was concentrated, dissolved in NaOH (20 mls 0.5 N), filtered, extracted with ether three times, and cooled to 0° C. At 0° C., 1.0 N HCl was added slowly until a pH of 6.5 was attained. The mixture was stirred at 0° C. for 30 minutes and the product was filtered, dried in air, treated with excess 2.0 N HCl in ether, concentrated, then triturated with CH$_2$Cl$_2$ to give 1.12 g, 99% (95.5% purity). 385 mgs were purified via prep HPLC (Sunfire, TFA), concentrated, treated with excess 1.0 N HCl (aq.), concentrated to a small volume and lyophilized to afford 240 mgs of the captioned compound. M+1=527; $^1$H NMR 6 (CD$_3$OD) 7.86 (d, 2H), 7.64 (s, 4H), 7.49 (d, 2H), 7.36 (m, 2H), 7.28 (m, 1H), 7.02 (m, 1H), 6.95 (s, 1H), 6.75 (q, 1H), 4.26 (t, 1H), 3.32 (m, 1H), 3.21 (m, 1H).

6.39. Synthesis of (S)-2-Amino-3-(4-(2-amino-6-(benzylthio)pyrimidin-4-yl)phenyl)propanoic acid

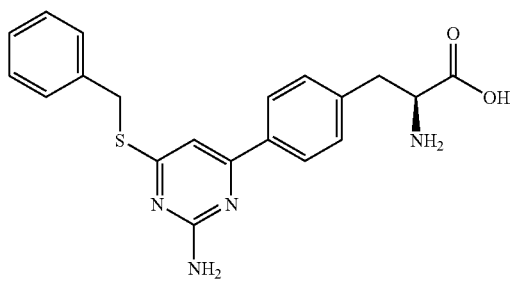

Benzylmercaptan (0.14 g, 1.11 mmol) was treated with NaH (60% in mineral oil, 67 mg, 1.66 mmol) in dry THF (15 ml) for 30 minutes. 2-Amino-4,6-dichloropyrimidine (0.2 g, 1.22 mmol) was added and the mixture was stirred overnight. The mixture was diluted with methylenechloride, washed with water, then brine, dried over MgSO$_4$, and concentrated to give 0.11 g of 4-(benzylthio)-6-chloropyrimidin-2-amine.

4-(Benzylthio)-6-chloropyrimidin-2-amine (0.1 g, 0.397 mmol), L-p-boronophenylalanine (0.1 g, 0.477 mmol), Pd(PPh$_3$)$_2$Cl$_2$ (17 mg, 0.024 mmol), Na$_2$CO$_3$ (93 mg, 0.874 mmol), MeCN (2.5 ml) and water (2.5 ml) were heated at 150° C. for 5 minutes in a microwave. The mixture was concentrated and purified via prep HPLC to give 0.42 g of the title compound. M+1=381; $^1$H NMR (CD$_3$OD) δ 7.8 (d, 2H), 7.37 (t, 4H), 7.23 (m, 2H), 7.16 (m, 1H), 6.98 (s, 1H), 4.43 (s, 2H), 4.20 (t, 1H), 3.29 (m, 1H), 3.13 (M, 1H).

6.40. Synthesis of (S)-2-Amino-3-(4-(2-amino-6-(naphthalen-2-ylmethylthio)pyrimidin-4-yl)phenyl) propanoic acid

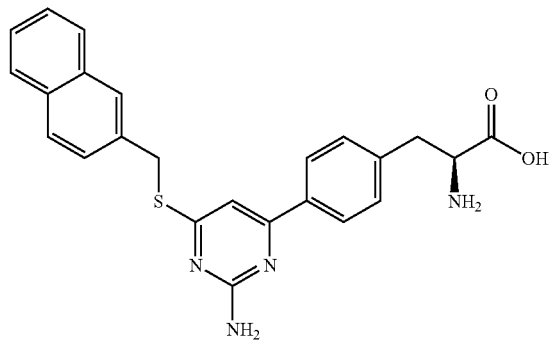

2-Mercaptonapthalene (0.2 g, 1.148) was treated with NaH (60% in Mineral oil, 92 mg, 2.30 mmol) in dry THF (10 ml) for 30 minutes. 2-Amino-4,6-dichloropyrimidine (0.21 g, 1.26 mmol) was added and the mixture was stirred overnight. The mixture was diluted with methylenechloride, washed with water, then brine, dried over MgSO$_4$, and concentrated to give 0.18 g 4-chloro-6-(naphthalen-2-ylmethylthio)pyrimidin-2-amine.

4-Chloro-6-(naphthalen-2-ylmethylthio)pyrimidin-2-amine (0.1 g, 0.331 mmol), L-p-boronophenylalanine (83 mg, 0.397 mmol), Pd(PPh$_3$)$_2$Cl$_2$ (14 mg, 0.020 mmol), Na$_2$CO$_3$ (77 mg, 0.729 mmol), MeCN (2.5 ml) and water (2.5 ml) were heated at 150° C. for 5 minutes in a microwave. The mixture was concentrated and purified via prep HPLC to give 57 mg of the title compound. M+1=431; $^1$H NMR (CD$_3$OD) δ 7.85 (s, 1H), 7.79 (d, 2H), 7.72 (d, 3H), 7.46 (dd, 1H), 7.35 (m, 4H), 6.95 (s, 1H), 4.58 (s, 2H), 4.17 (m, 1H), 3.26 (m, 1H), 3.11 (m, 1H).

6.41. Synthesis of (2S)-2-Amino-3-(4-(2-amino-6-(1-(3,4-difluorophenyl)-2,2,2-trifluoroethoxy)pyrimidin-4-yl)phenyl)propanoic acid

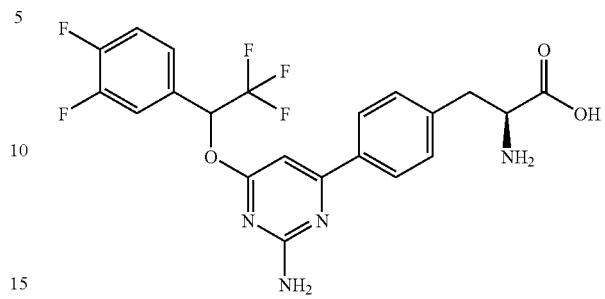

3,5-Difluorophenyl-trifluoromethyl ketone was treated with NaBH$_4$ (0.18 g, 4.76 mmol) in THF (5 ml) for 2 hours. The mixture was quenched with water, extracted with methylene chloride (2×). The organics were combined, filtered through silica gel and concentrated to give 0.46 g of 1-(3,4-difluorophenyl)-2,2,2-trifluoroethanol.

1-(3,4-Difluorophenyl)-2,2,2-trifluoroethanol (0.1 g, 0.471 mmol) was treated with NaH (60% in mineral oil, 38 mg, 0.943 mmol) in dry THF (3 ml) for 30 minutes. 2-Amino-4,6-dichloropyrimidine (77 mg, 0.471 mmol) was added and the mixture was stirred at 50° C. for 6 hours. The mixture was quenched with water and extracted with methylenechloride (2×). The organics were combined, washed with water, then brine, dried over MgSO4, and concentrated to give 0.14 g of 4-chloro-6-(1-(3,4-difluorophenyl)-2,2,2-trifluoroethoxy)-pyrimidin-2-amine.

4-Chloro-6-(1-(3,4-difluorophenyl)-2,2,2-trifluoroethoxy)pyrimidin-2-amine (0.14 g, 0.421 mmol), L-p-boronophenylalanine (110 mg, 0.505 mmol), Pd(PPh$_3$)$_2$Cl$_2$ (18 mg, 0.025 mmol), Na$_2$CO$_3$ (98 mg, 0.926 mmol), MeCN (2.5 ml) and water (2.5 ml) were heated at 150° C. for 5 minutes in a microwave. The mixture was concentrated and purified via prep HPLC to give 74 mg of the title compound. M+1=469; $^1$H NMR (CD$_3$OD) δ 7.83 (d, 2H), 7.47 (m, 1H), 7.38 (m, 4H), 7.28 (m, 1H), 4.21 (t, 1H), 3.29 (m, 1H), 3.15 (m, 1H).

6.42. Synthesis of (2S)-2-Amino-3-(4-(2-amino-6-(2,2,2-trifluoro-1-(3'-methylbiphenyl-2-yl)ethoxy)pyrimidin-4-yl)phenyl)propanoic acid

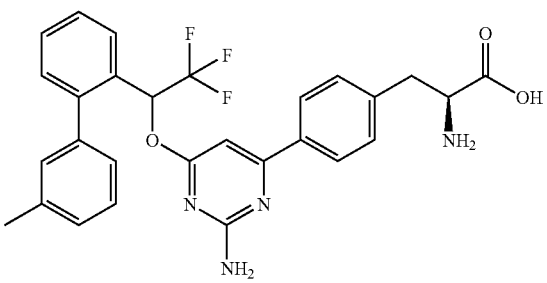

To 4'-bromo-2,2,2-trifluoroacetophenone (5.0 g, 19.76 mmol) in THF (50 mls) at 0° C. was added NaBH$_4$ (1.5 g, 39.52 mmol). The mixture was warmed to room temperature and stirred for 1 hour. The reaction was complete by TLC (CH$_2$Cl$_2$). The mixture was quenched with H$_2$O, rotary evaporated to remove most of the THF, and extracted 2 times with CH$_2$Cl$_2$. The organics were combined, washed with brine, concentrated to a small volume and filtered through a plug of silica gel. The silica was washed with CH$_2$Cl$_2$ to elute the product, and the resulting solution was concentrated to give 4.65 g of 1-(4-bromophenyl)-2,2,2-trifluoroethanol. Yield: 92%.

1-(4-Bromophenyl)-2,2,2-trifluoroethanol (0.13 g, 0.525 mmol), m-tolylboronic acid (0.1 g, 0.736 mmol), Fibercat (4.28% Pd, 47 mgs, 0.0157 mmol Pd), $K_2CO_3$ (0.22 g, 1.576 mmol), EtOH (3 mls), and $H_2O$ (0.5 mls) were combined and heated at 80° C. for 4 hours. The reaction was shown complete by TLC ($CH_2Cl_2$). The mixture was cooled, filtered, concentrated, slurried in $CH_2Cl_2$, and chromatographed over silica gel ($CH_2Cl_2$) to give 0.1 g of 2,2,2-trifluoro-1-(3'-methylbiphenyl-2-yl)ethanol. Yield: 72%.

Alternatively, 1-(4-bromophenyl)-2,2,2-trifluoroethanol (0.98 g, 3.86 mmol), m-tolylboronic acid (0.63 g, 4.63 mmol), $Pd(PPh_3)_2Cl_2$ (0.16 g, 0.232 mmol Pd), $Na_2CO_3$ (0.90 g, 8.49 mmol), AcCN (10 mls), and $H_2O$ (10 mls) were combined and heated in the microwave at 150° C. for 10 minutes. The reaction was shown complete by TLC ($CH_2Cl_2$). The mixture was cooled, concentrated, slurried in $CH_2Cl_2$, filtered, and chromatographed over silica gel ($CH_2Cl_2$) to give 0.80 g of 2,2,2-trifluoro-1-(3'-methylbiphenyl-2-yl)ethanol. Yield: 79%.

Alternatively, tetrabutylammoniumfluoride (TBAF 1.0 N in THF 13 uL, 3.3 mg, 0.013 mmol) was added to a mixture of 3-methyl-biphenyl-2-carboxaldehyde (0.25 g, 1.27 mmol) and trifluoromethytrimethyl silane (0.25 g, 1.53 mmol), in THF (1.5 ml) at 0° C. The reaction was warmed to room temperature and stirred for 4 hours. HCl (3.0 N, 2.0 ml) was added, and the mixture was stirred for 3 hours. The mixture was concentrated, dissolved in methylene chloride, filtered through silica gel, and concentrated to give 0.15 g of 2,2,2-trifluoro-1-(3'-methylbiphenyl-2-yl)ethanol.

2,2,2-Trifluoro-1-(3'-methylbiphenyl-2-yl)ethanol (0.15 g, 0.563 mmol) was treated with NaH (60% in mineral oil, 45 mg, 1.12 mmol) in dry THF (5 ml) for 30 minutes. 2-Amino-4,6-dichloropyrimidine (92 mg, 0.5633 mmol) was added and the mixture was stirred at 50° C. for 6 hours. The mixture was quenched with water and extracted with methylenechloride (2×). The organics were combined, washed with water, then brine, dried over MgSO4, and concentrated to give 0.16 g of 4-chloro-6-(2,2,2-trifluoro-1-(3'-methylbiphenyl-2-yl)ethoxy)pyrimidin-2-amine.

4-Chloro-6-(2,2,2-trifluoro-1-(3'-methylbiphenyl-2-yl)ethoxy)pyrimidin-2-amine (0.16 g, 0.406 mmol), L-p-boronophenylalanine (10 mg, 0.487 mmol), $Pd(PPh_3)_2Cl_2$ (17 mg, 0.024 mmol), $Na_2CO_3$ (95 mg, 0.894 mmol), MeCN (2.5 ml) and water (2.5 ml) were heated at 150° C. for 5 minutes in a microwave. The mixture was concentrated and purified via prep HPLC to give 105 mg of the title compound. M+1=523; $^1$H NMR ($CD_3OD$) δ 7.85 (d, 2H), 7.70 (d, 1H), 7.44 (m, 4H), 7.31 (t, 1H), 7.21 (m, 2H), 7.10 (m, 2H), 6.87 (q, 1H), 6.84 (s, 1H), 4.25 (t, 1H), 3.30 (m, 1H), 3.18 (m, 1H).

6.43. Synthesis of (S)-2-Amino-3-(4-(5-(3-(cyclopentyloxy)-4-methoxybenzylamino)pyridin-3-yl)phenyl)propanoic acid

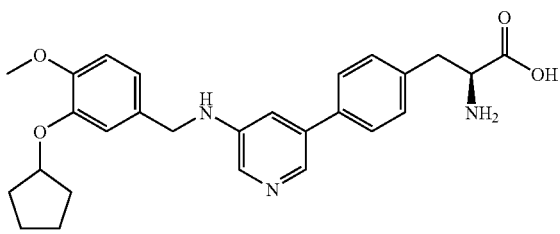

Sodium triacetoxyl-borohydride (245 mg, 1.16 mmol) was added to the solution of 5-bromo-pyridine-3-amine (100 mg, 0.57 mmol) and 3-cyclopentyloxy-4-methoxy-benzaldehyde (127 mg, 0.57 mmol) in 10 ml of 1,2-dichloroethtane (DCE), of HOAc (66 μL, 2 eq. 1.16 mmol) was added, the mixture was stirred overnight at room temperature, followed by addition of 15 ml of DCE. The organic phase was washed with water, and dried over sodium sulfate. The solvent was removed by under reduced pressure to give 200 mg of crude 5-bromo-N-(3-(cyclopentyloxy)-4-methoxybenzyl)pyridin-3-amine, which was used for the next step without further purification.

An Emrys process vial (2-5 ml) for microwave was charged with 5-bromo-N-(3-(cyclopentyloxy)-4-methoxybenzyl)pyridin-3-amine (40 mg, 0.106 mmol), 4-borono-L-phenylalanine (22 mg, 0.106 mmol) and 2 ml of acetonitrile. Aqueous sodium carbonate (2 ml, 1M) was added to above solution followed by 10 mol percent of dichlorobis (triphenylphosphine)-palladium (II). The reaction vessel was sealed and heated to 180° C. for 10 minutes with a microwave. After cooling, the reaction mixture was evaporated to dryness. The residue was dissolved in 2.5 ml of methanol and purified with Prep-LC to give 20 mg of (S)-2-amino-3-(4-(5-3-(cyclophentyloxy-4-methoxy-benzylamino)pyridine-3-yl)phenyl)-propanoic acid. NMR: $^1$H-NMR (400 MHz, $CD_3OD$): δ 1.59 (m, 2H), 1.7 (m, 6H), 3.17 (m, 1H), 3.3 (m, 1H), 3.75 (s, 3H), 4.2 (dd, 1H) 4.39 (s, 2H), 4.7 (m, 1H), 6.9 (m, 3H), 7.4 (d, 2H), 7.6 (d, 2H), 7.7 (s, 1H), 7.9 (s, 1H), 8.15 (s, 1H); Analytical HPLC: RT 2.69; M+1: 462 (RT: 1.285).

6.44. Synthesis of 2-Amino-3-(3-(4-amino-6-((R)-1-(naphthalen-2-yl)ethylamino)-1,3,5-triazin-2-yl)phenyl)propanoic acid

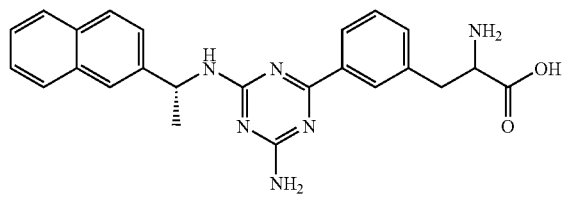

To a solution of tert-butyl 2-(diphenylmethylene-amino) acetate (400 mg, 1.35 mmol) in THF (25 ml) was added a solution of LDA (1.8M in THF, 2 eq, 2.7 mmol, fresh bottle from Aldrich) over 5 minutes at −78° C., and the resulting mixture was stirred for 20 minutes. A solution of 2-(3-(bromomethyl)phenyl)-5,5-dimethyl-1,3,2-dioxaborinane (460 mg, 1.2 eq. 1.62 mmol) in THF (10 ml) was added drop-wise to the reaction mixture over 5 minutes. The reaction was continued at same (−78° C.) temperature for 30 minutes, and left for 3 hours at room temperature. The reaction was quenched with saturated $NH_4Cl$, followed by the addition of water (30 ml), and was extracted with EtOAc (2×40 ml). The organic fractions were combined and dried over $Na_2SO_4$. The solvent was then concentrated at reduced pressure and crude tert-Butyl-3-(3-(5,5-dimethyl-1,3,2-dioxaborinan-2-yl)phenyl) 2(diphenylmethylene amino) propionate was purified by column chromatography to provide the product as a semi-solid.

An Emrys process vial (20 ml) for microwave was charged with (R)-6-chloro-$N^2$-(1-(naphthalene-2-yl)ethyl)-1,3,5-triazine-2,4-diamine (100 mg, 0.33 mmol), tert-butyl-3-(3-(5,5-dimethyl-1,3,2-dioxaborinan-2-yl)phenyl)-2-(diphenyl methyleneamino) propanoate (248 mg, 0.5 mmol, 1.5 eq.) and 6 ml of acetonitrile plus 6 ml of aqueous sodium carbonate (1M) was added to above solution followed by 10 mol percent of dichlorobis(triphenylphosphine)-palladium(II). The reaction vessel was sealed and heated to 190° C. for 10 minutes with microwave. After cooling, the reaction mixture was evaporated to dryness. The residue was dissolved in 10 ml of THF, to which was added 5N.HCl (5 ml). The mixture was refluxed for 2 hours in order to deprotect the benzophone and tert-butyl groups. The resulting reaction mixture was concentrated and dissolved in methanol (8 ml) and purified with Prep-LC to afford 15 mg of 2-amino-3-(4(4-amino-6-((R)-1-(naphthalene-2-yl)ethylamino)-1,3,5-trizin-2-yl)phenyl)propanoic acid. NMR: $^1$H-NMR (400 MHz, CD$_3$OD): δ 1.85 (d, 3H), 3.2-3.45 (m, 2H), 4.37 (m, 1H), 5.5 (m, 1H), 7.4 (m, 1H), 7.6 (m 4H), 7.9 (m, 4H), 8.18 (m, 2H), Analytical HPLC: RT 2.79 M+1: 429 (RT: 1.35).

6.45. Synthesis of 2-Amino-3-(4-(4-amino-6-((R)-1-(naphthalen-2-yl)ethylamino)-1,3,5-triazin-2-yl)-2-fluorophenyl)propanoic acid

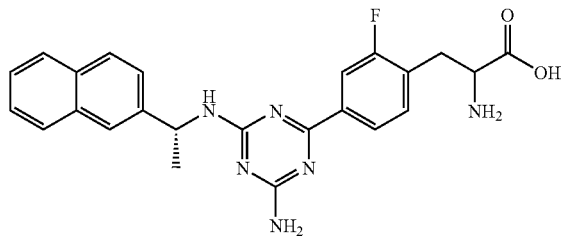

To a solution of tert-butyl 2-(diphenylmethylene-amino) acetate (1.1 g, 3.73 mmol) in THF (30 ml) was added a solution of LDA (1.8M in THF, 1 eq, 3.73 mmol, fresh bottle from Aldrich) over 5 minutes at −78° C., and the resulting mixture was stirred for 20 minutes. A solution of 4-bromo-1-(bromomethyl)-2-fluorobenezene (1 g, 3.74 mmol) in THF (10 ml) was added drop-wise to the reaction mixture over 5 minutes. The reaction was continued at −78° C. for 30 minutes, after which it was left at room temperature for 3 hours. The reaction was quenched with saturated NH$_4$Cl, after which water (30 ml) was added. Product was extracted with EtOAc (2×40 ml), and the organic fractions were combined and dried over Na$_2$SO$_4$. The solvent was concentrated at reduced pressure and crude tert-Butyl 3-(4-bromo-2-fluorophenyl)-2-(diphenylmethyleneamino)-propanoate was purified by column chromatography. The product was obtained as a solid.

An Emrys process vial (20 ml) for microwave was charged with tert-butyl 3-(4-bromo-2-fluorophenyl)-2-(diphenylmethylene-amino)propanoate (600 mg, 1.24 mmol), Pd(dba)$_2$ (71 mg, 0.124 mmol), PCy3 (35 mg, 0.124 mmol), 4,4,4',4', 5,5,5',5'-octamethyl-2,2'-bi(1,3,2-dioxaborolane (346 mg, 1.1 eq. 1.36 mmol) and KOAc (182 mg, 1.5 eq., 1.86 mmol) 20 ml of DMF. The reaction vessel was sealed and heated to 160° C. for 20 minutes by microwave. After cooling, the reaction mixture was evaporated to dryness under reduced pressure. The residue was dissolved in H$_2$O (30 ml), extracted with EtOAc (2×40 ml), and purified with Prep-LC to give 220 mg of tert-butyl 2-(diphenylmethyleneamino)-3-(2-fluoro-4-(4,4,5,5-tetramethyl-1,3,2-dioxaborolan-2-yl)phenyl)propanoate.

An Emrys process vial (5 ml) for microwave was charged with (R)-6-chloro-N$^2$-(1-(naphthalene-2-yl)ethyl)-1,3,5-triazine-2,4-diamine (67 mg, 0.22 mmol), tert-butyl-2-(diphenylmethyleneamino)-3-(2-fluoro-4-(4,4,5,5-tetramethyl-1,3,2-dioxaborolan-2-yl)phenyl)propanoate (120 mg, 0.22 mmol) and 2 ml of acetonitrile. Aqueous sodium carbonate (2 ml, 1M) was added to above solution followed by 10 mol percent dichlorobis(triphenylphosphine)-palladium(II). The reaction vessel was sealed and heated to 190° C. for 10 minutes by microwave. After cooling, the reaction mixture was evaporated to dryness. The residue was dissolved in 10 ml of THF, to which 5N.HCl (2 ml) was then added. The mixture was refluxed for 2 hours (deprotection of benzophone and tert-butyl groups). After deprotection of two groups, the mixture was concentrated, dissolved in methanol (5 ml), and purified with Prep-LC to afford 10 mg of 2-amino-3-(4-(4-amino-6-((R)-1-(naphthalene-2-yl)ethylamino)-1,3,5-trizin-2-yl)-2-fluorophenyl)propanoic acid. NMR: $^1$H-NMR (400 MHz, CD$_3$OD): δ 1.6 (d, 3H), 3.07 (m, 1H), 3.45 (m, 1H), 3.8 (m, 1H), 5.45 (m, 1H), 7.4 (m, 4H), 7.6 (m 1H), 7.8 (m, 4H), 8.08 (m, 1H), Analytical HPLC: RT 2.88, M+1: 447 (RT: 1.44).

6.46. Synthesis of (2S)-2-Amino-3-(4-(4-amino-6-(1-(adamantyll)ethylamino)-1,3,5-triazin-2-yl)phenyl)propanoic acid

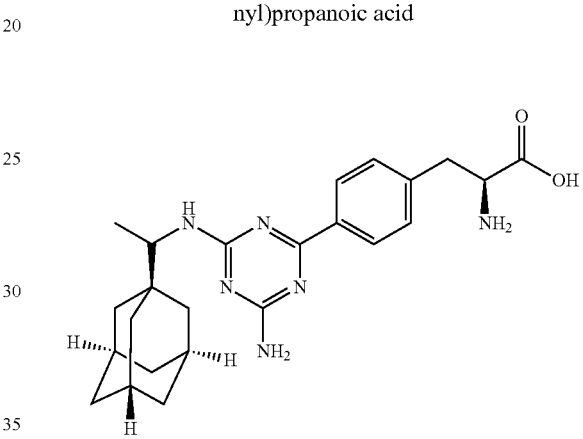

A solution of adamantine amine (1 equivalent), 2-amino-4,6-dichloro-[1,3,5]triazine (1 equivalent) and diisopropyl ethyl amine (5 equivalents, Aldrich) in anhydrous 1,4-dioxane was refluxed at 130° C. for 3 hours. After completion of the reaction, the dioxane was removed under reduced pressure. The reaction was then cooled to room temperature, water was added, and product was extracted with dichloromethane (2×40 ml). The combined organic solution was dried over Na$_2$SO$_4$ and concentrated to afford product, which was used in the next step without purification.

An Emrys process vial (20 ml) for microwave was charged with adamantine trizine chloride (200 mg, 0.65 mmol), 4-borono-L-phenylalanine (135 mg, 0.65 mmol) and 5 ml of acetonitrile. Aqueous sodium carbonate (5 ml, 1M) was added to above solution followed by 5 mol percent dichlorobis(triphenylphosphine)-palladium(II). The reaction vessel was sealed and heated to 190° C. for 20 minutes by microwave. After cooling, the reaction mixture was evaporated to dryness. The residue was dissolved in 4 ml of methanol and purified with Prep-LC to give 60 mg (yield 21%) of coupled product. NMR: $^1$H-NMR (400 MHz, CD$_3$OD): δ 1.22 (m, 3H), 1.6-1-8 (m, 12H), 2.01 (d, 3H), 3.25-3.42 (m, 2H), 4.0 (m, 1H), 4.40 (m, 1H), 7.6 (d, 2H), 8.2 (d, 2H), Analytical HPLC: RT 3.11, M+1: 437 (RT: 1.76).

6.47. Alternative Synthesis of (2S)-2-Amino-3-(4-(4-amino-6-(1-(adamantyll)ethylamino)-1,3,5-triazin-2-yl)phenyl)propanoic acid Adamantane (2-yl)ethyl cyanoguanidine was prepared by forming a solution of cyanoguanidine (1 equivalent), (S)-2- amino-3-(4-cyanophenyl)propanoic acid (1 equivalent) and potassium tertiary butaoxide (3.5 equivalent, Aldrich) in dry n-BuOH, which was vigorously refluxed at 160° C. in a sealed tube for 2 days. After completion of the reaction, the mixture was allowed to cool to room temperature, and the reaction was quenched with water. Solvent was removed under reduced pressure. Again, after allowing to cool to room temperature, the reaction mixture was brought to pH 12-14 by adding 1N NaOH. Then, impurities were removed while extracting with Ether:EtOAc (9:1, 2×100 ml). The aqueous solution was cooled to 0° C., 1N HCl was then added to adjust pH to 7. The pale yellow product was slowly crashed out in $H_2O$, the mixture was kept in a refrigerator for 30 minutes, and the solid was obtained by filtration with 92% purity. Compound was crystallized from MeOH to afford a white solid (>98% pure, 48-78% yield). $^1$H-NMR (400 MHz, $CD_3OD$): δ 1.0 (d, 3H), 1.45-1.6 (m, 6H), 4.62-4.8 (m, 4H) 2.0 (m, 2H), 3.3 (m, 1H), 3.5 (m, 1H); Analytical HPLC: RT 2.69; M+1: 462 (RT: 1.285).

The title compound was prepared from adamantane (2-yl) ethyl cyanoguanidine using the method shown in Scheme 6.

6.48. Synthesis of (S)-2-Amino-3-(4-(5-fluoro-4-((R)-1-(naphthalen-2-yl)ethylamino)pyrimidin-2-yl)phenyl)propanoic acid

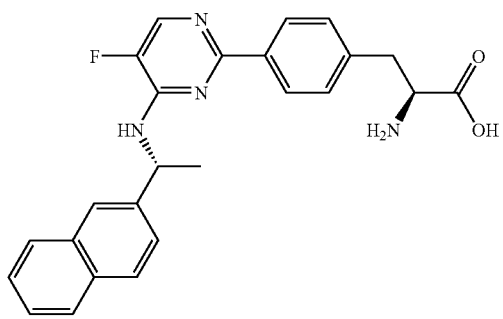

A mixture of (R)-(+)-1-(2-napthyl)ethylamine (102.6 mg, 0.599 mmol), 2,4-dichloro-5-fluororo pyrimidine (100 mg, 0.599 mmol) and cesium carbonate (390 mg, 1.2 mmol) was dissolved in 1,4-dioxane (3 ml) and $H_2O$ (3 ml) in a 10 ml microwave vial. The mixture was stirred in the microwave reactor at 80° C. for 10 minutes. The residue was dissolved in $CH_2Cl_2$ (50 ml), washed with water (20 ml), brine (20 ml) dried ($Na_2SO_4$) and concentrated to get the crude intermediate 2-chloro-5-fluoro-pyrimidin-4-yl)-(1-naphthalen-2-yl-ethyl)-amine.

The crude intermediate (250 mg, 0.83 mmol) was then dissolved in 6.0 ml of MeCN and 6 ml of $H_2O$ in a 20 ml microwave vial. To this solution were added L-p-boronophenylalanine (173.6 mg, 0.83 mmol), sodium carbonate (173.6 mg, 1.66 mmol) and catalytic amount of dichlorobis (triphenylphosphine)-palladium(I) (11.6 mg, 0.0166 mmol). The reaction vial was then sealed and stirred in the microwave reactor at 150° C. for 7 minutes. The contents were then filtered, and the filtrate was concentrated and dissolved in MeOH and $H_2O$ (1:1) and purified by preparative HPLC using MeOH/$H_2O$/TFA as the solvent system. The combined pure fraction were evaporated in vacuo and further dried on a lyophilizer to give 154 mg of 2-amino-3-{4-[5-fluoro-4-(1-naphthalen-2-yl-ethylamino)-pryrimidin-2-yl]-phenyl}-propionic acid. NMR: $^1$H-NMR (400 MHz, $CD_3OD$) δ 1.8 (d, 3H) 3.2-3.4 (m, 2H), 4.35 (m, 1H), 5.7 (q, 1H), 7.5 (m, 4H), 7.6 (d, 1H), 7.8-7.9 (m, 4H), 8.1 (d, 2H), 8.3 (d, 1H). LCMS: M+1=431.

6.49. Synthesis of (S)-2-Amino-3-(4-(2-amino-6-(4-(trifluoromethyl)-benzylamino)pyrimidin-4-yl)phenyl)propanoic acid

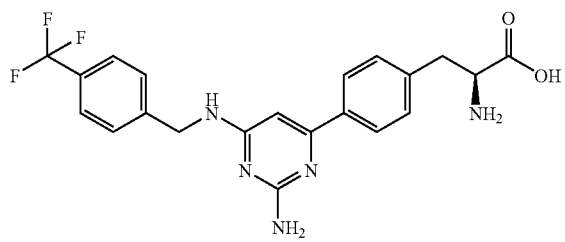

A mixture of trifluoromethyl benzylamine (106.8 mg, 0.610 mmol), 2-amino-4,6-dichloropyrimidine (100 mg, 0.610 mmol) and cesium carbonate (217 mg, 1.2 mmol) was dissolved in 1,4-dioxane (6 ml) and $H_2O$ (6 ml) in a 20 ml microwave vial. The mixture was stirred in the microwave reactor at 210° C. for 25 minutes. The solvent was then removed. The residue was dissolved in $CH_2Cl_2$ (50 ml), washed with water (20 ml), brine (20 ml), dried ($Na_2SO_4$) and concentrated to get the crude intermediate 6-chloro-N-4'-(trifluoromethyl-benzyl)-pryrimidine-2-4-diamine.

The crude intermediate (150 mg, 0.497 mmol) was then dissolved in 3.0 ml of MeCN and 3 ml of $H_2O$ in a 10 ml microwave vial. To this solution were added L-p-boronophenylalanine (104 mg, 0.497 mmol), sodium carbonate (150 mg, 0.994 mmol) and catalytic amount of dichlorobis(triphenylphosphine)-palladium(II) (6.9 mg, 0.00994 mmol). The reaction vial was then sealed and stirred in the microwave reactor at 150° C. for 5 minutes. The contents were filtered, and the filtrate was concentrated and dissolved in MeOH and $H_2O$ (1:1) and purified by preparative HPLC using a MeOH/$H_2O$/TFA solvent system. The combined pure fractions were evaporated in vacuo and further dried on a lyophilizer to afford 2-amino-3-{4-[2-amino-6-(4-trifluoromethyl-benzylamino)-pyrimidin-4-yl]-phenyl}-propionic acid. NMR: $^1$H-NMR (300 MHz, $CD_3OD$) δ 3.1-3.3 (m, 2H), 4.2 (t, 1H), 4.7 (s, 2H), 6.3 (s, 1H), 7.4-7.5 (m, 4H), 7.6 (d, 2H), 7.7 (d, 2H). LCMS: M+1=432.

6.50. Synthesis of 2-Amino-3-(5-(5-phenylthiophen-2-yl)-1H-indol-3-yl)propanoic acid

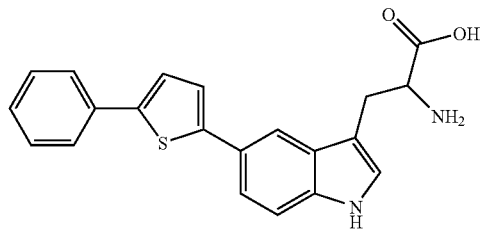

2-Amino-3-(5-bromo-1H-indol-3-yl)-propionic acid (0.020 g, 0.071 mmol) was added to a 5 ml microwave vial, which contained 5-phenyl-thiophen-2-boronic acid (0.016 g, 0.078 mmol), $Na_2CO_3$ (0.015 g, 0.142 mmol), acetonitrile (1.5 ml)/water (1.5 ml) and dichlorobis(triphenylphosphine)-palladium (3 mg, 0.003 mmol). Microwave vial was capped and stirred at 150° C. for 5 min under microwave radiation. Reaction mixture was cooled, filtered through a syringe filter and then separated by a reverse phase preparative-HPLC using YMC-Pack ODS 100×30 mm ID column (MeOH/$H_2O$/

TFA solvent system). The pure fractions were concentrated in vacuum. The product was then suspended in 5 ml of water, frozen and lyophilized to give 5 mg of pure product, 2-amino-3-[5-(5-phenyl-thiophen-2-yl)-1H-indol-3-yl]-propionic acid. $^1$H-NMR (300 MHz, CD$_3$OD): 3.21-3.26 (m, 2H), 4.25 (q, 1H), 7.15-7.35 (m, 8H), 7.58 (d, 2H), 7.82 (d, 1H).

6.51. Synthesis of (S)-2-Amino-3-(4-(4-(4-phenoxyphenyl)-1H-1,2,3-triazol-1-yl)phenyl)propanoic acid

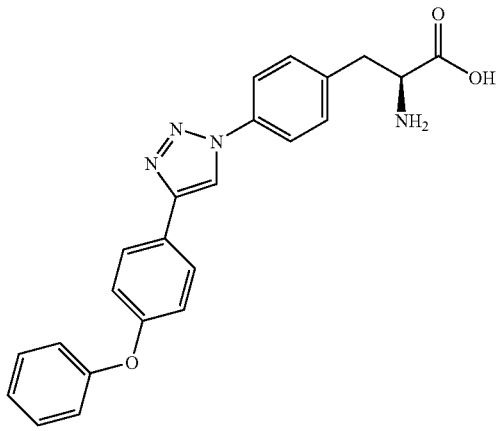

A mixture of 1-ethynyl-4-phenoxy-benzene (126 mg, 0.65 mmol) and (S)-3-(4-azido-phenyl)-2-tert-butoxycarbonylamino-propionic acid (200 mg, 0.65 mg) in H$_2$O:dioxane (5:1) was heated at 100° C. in a sealed tube for overnight. After completion of reaction, 3N HCl (5 ml) was added and the mixture was stirred for 2 hr at 50° C. Removal of solvent gave crude product which was dissolved in MeOH and purified by preparative HPLC to give 45 mg of desired product (yield: 29%). $^1$H-NMR (400 MHz, CD$_3$OD): δ (ppm) 3.2 (m, 1H), 3.4 (m, 1H), 4.3 (m, 1H), 6.9 (d, 2H), 7.0 (d, 2H), 7.2 (m, 1H), 7.3 (d, 2H), 7.4-7.55 (m, 6H), 8.0 (s, 1H).

6.52. Synthesis of (S)-2-Amino-3-(4-(4-(4-(thiophene-2-carboxamido)phenyl)-1H-1,2,3-triazol-1-yl)phenyl)propanoic acid and (S)-2-Amino-3-(4-(5-(4-(thiophene-2-carboxamido)phenyl)-1H-1,2,3-triazol-1-yl)phenyl)propanoic acid

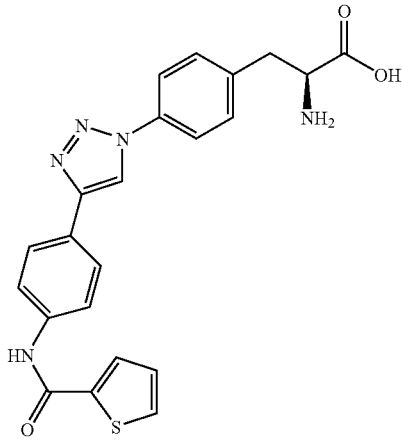

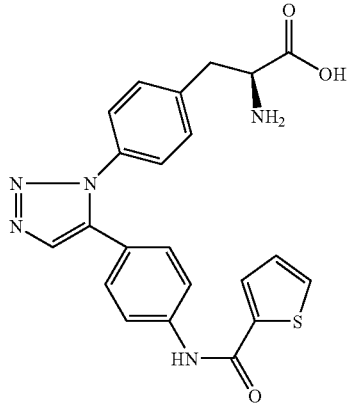

A mixture of thiophene-2-carboxylic acid (4-ethyl-phenyl) amide (117 mg, 0.49 mmol) and (S)-3-(4-azido-phenyl)-2-tert-butoxycarbonylamino-propionic acid (150 mg, 0.49 mg) in 5 ml of H$_2$O:dioxane (5:1) was heated at 100° C. in a sealed tube overnight. After completion of reaction, 3N HCl (5 ml) was added and the mixture was stirred for 2 hr at 50° C. Removal of solvent gave crude product which was dissolved in MeOH and purified by preparative HPLC. According to LCMS (retention time) and NMR, two regio-isomers were obtained (total yield: 70 mg, 66%). The major product is (S)-2-amino-3-(4-(4-(4-(thiophene-2-carboxamido)phenyl)-1H-1,2,3-triazol-1-yl)phenyl)propanoic acid. NMR: $^1$H-NMR (400 MHz, CD$_3$OD): δ 3.2 (m, 1H), 3.4 (m, 1H), 4.3 (m, 1H), 7.15 (m, 1H), 7.3 (d, 2H), 7.6 (m, 4H), 7.0 (m, 3H), 7.95 (d, 1H), 8.0 (s, 1H). The minor product is (S)-2-amino-3-(4-(5-(4-(thiophene-2-carboxamido)phenyl)-1H-1,2,3-triazol-1-yl)phenyl)propanoic acid. $^1$H-NMR (400 MHz, CD$_3$OD): δ 3.2 (m, 1H), 3.4 (m, 1H), 4.35 (m, 1H), 7.2 (m, 1H), 7.3 (d, 2H), 7.5-7.6 (m, 4H), 7.75 (m, 3H), 7.95 (d, 1H), 8.05 (s, 1H).

6.53. Synthesis of (S)-2-Amino-3-(4-(2-amino-6-(phenylethynyl)pyrimidin-4-yl)phenyl)propanoic acid

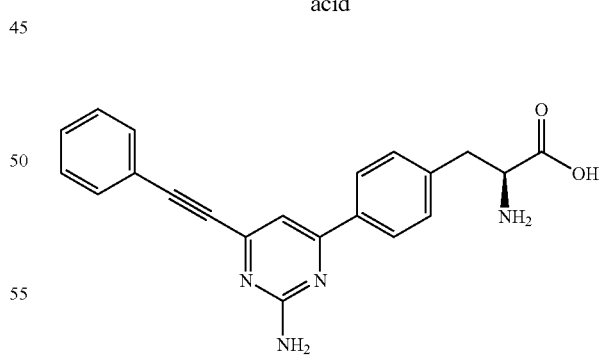

2-Amino 4,6-dichloro pyrimidine (0.180 g, 1.1 mmol), trimethyl-phenylethynyl-stannane (0.264 g, 1 mmol), were dissolved in THF (20 ml) and the mixture was stirred at 65° C. for 12 h. LCMS indicated the completion of reaction. Solvent was removed and the residue was directly used in the following step.

The crude intermediate (0.42 g), L-p-borono-phenylalanine (0.210 g, 1 mmol), sodium carbonate (0.210 g, 2 mmol), and dichlorobis (triphenylphosphine)-palladium(II) (25 mg, 0.036 mmol) were dissolved in a mixture of MeCN (3 ml) and $H_2O$ (3 ml) in a 10 ml microwave vial. The vial was sealed and stirred in the microwave reactor at 150° C. for 6 min. The mixture was filtered and the filtrate was concentrated. Residue was purified by preparative HPLC using $MeOH/H_2O$/TFA as solvent system to obtain (S)-2-amino-3-[4-(2-amino-6-phenylethynyl-pyrimidin-4-yl(-phenyl]-propionic acid as a TFA salt. $^1$H-NMR (400 MHz, $CD_3OD$): δ (ppm) 3.20-3.42 (m, 2H), 4.31 (m, 1H), 7.40-7.51 (m, 6H), 7.62 (d, 2H), 8.18 (d, 2H).

6.54. Additional Compounds

Additional compounds prepared using methods known in the art and/or described herein are listed below:

| Compound | LCMS (M + 1) | HPLC Method (Time (min)) |
|---|---|---|
| (S)-2-amino-3-(4-(5-(2-fluoro-4,5-dimethoxybenzylamino)pyrazin-2-yl)phenyl)propanoic acid | 426 | C (3.04) |
| (S)-2-amino-3-(4-(2-amino-6-(4-(2-methoxyphenyl)piperidin-1-yl)pyrimidin-4-yl)phenyl)propanoic acid | 448 | I (3.03) |
| (S)-2-amino-3-(4-(6-(3-(cyclopentyloxy)-4-methoxybenzylamino)-2-(dimethylamino)pyrimidin-4-yl)phenyl)propanoic acid | 507 | J (3.21) |
| (S)-2-amino-3-(4-(5-(3,4-dimethylbenzylamino)pyrazin-2-yl)phenyl)propanoic acid | 377 | C (3.15) |
| (S)-2-amino-3-(4-(5-(biphenyl-2-ylmethylamino)pyrazin-2-yl)phenyl)propanoic acid | 425 | D (4.00) |
| (S)-ethyl 2-amino-3-(4-(2-amino-6-(4-(trifluoromethyl)benzylamino)pyrimidin-4-yl)phenyl)propanoate | 460 | F (2.52) |
| (S)-2-amino-3-(4-(5-(cyclopentylmethylamino)pyrazin-2-yl)phenyl)propanoic acid | 341 | C (2.77) |
| (2S)-2-amino-3-(4-(2-amino-6-(3-(2-(trifluoromethyl)phenyl)pyrrolidin-1-yl)pyrimidin-4-yl)phenyl)propanoic acid | 472 | A (2.87) |
| (2S)-2-amino-3-(4-(2-amino-6-(1,2,3,4-tetrahydronaphthalen-1-ylamino)pyrimidin-4-yl)phenyl)propanoic acid | 404 | A (2.65) |
| (S)-2-amino-3-(4-(2-amino-6-((R)-1-(naphthalen-2-yl)ethoxy)pyrimidin-4-yl)phenyl)propanoic acid | 429 | A (2.73) |
| (2S)-2-amino-3-(4-(2-amino-6-(1,2-diphenylethylamino)pyrimidin-4-yl)phenyl)propanoic acid | 454 | K (1.34) |
| (S)-2-amino-3-(4-(2-amino-6-((R)-1-(4-(benzo[b]thiophen-3-yl)phenyl)ethylamino)pyrimidin-4-yl)phenyl)propanoic acid | 510 | D (2.02) |
| (S)-2-amino-3-(4-(4-amino-6-((R)-1-(4'-methoxybiphenyl-4-yl)ethylamino)-1,3,5-triazin-2-yl)phenyl)propanoic acid | 485 | J (2.99) |
| 2-amino-3-(1-(4-amino-6-((R)-1-(naphthalen-2-yl)ethylamino)-1,3,5-triazin-2-yl)piperidin-4-yl)propanoic acid | 436 | B (2.25) |
| (2S)-2-amino-3-(4-(4-amino-6-(1-(4-fluoronaphthalen-1-yl)ethylamino)-1,3,5-triazin-2-yl)phenyl)propanoic acid | 447 | H (1.68) |
| (S)-2-amino-3-(4-(4-amino-6-((3'-fluorobiphenyl-4-yl)methylamino)-1,3,5-triazin-2-yl)phenyl)propanoic acid | 459 | J (2.89) |
| 2-amino-3-(4-(4-amino-6-((R)-1-(naphthalen-2-yl)ethylamino)-1,3,5-triazin-2-yl)-2-fluorophenyl)propanoic acid | 447 | A (2.88) |
| (S)-2-amino-3-(4-(2-amino-6-((R)-2,2,2-trifluoro-1-(3'-methoxybiphenyl-4-yl)ethoxy)pyrimidin-4-yl)phenyl)propanoic acid | 539 | M (3.83) |
| (2S)-2-amino-3-(4-(4-amino-6-(2,2,2-trifluoro-1-(3'-fluorobiphenyl-2-yl)ethoxy)-1,3,5-triazin-2-yl)phenyl)propanoic acid | 528 | F (3.41) |
| (2S)-2-amino-3-(4-(4-amino-6-(1-(4-tert-butylphenyl)ethylamino)-1,3,5-triazin-2-yl)phenyl)propanoic acid | 435 | J (1.82) |
| (2S)-2-amino-3-(4-(2-amino-6-(2,2,2-trifluoro-1-(3'-fluorobiphenyl-4-yl)ethoxy)pyrimidin-4-yl)phenyl)propanoic acid | 527 | D (2.09) |
| (2S)-2-amino-3-(4-(4-amino-6-(6,7-dihydroxy-1-methyl-3,4-dihydroisoquinolin-2(1H)-yl)-1,3,5-triazin-2-yl)phenyl)propanoic acid | 437 | B (2.47) |
| (2S)-2-amino-3-(4-(4-amino-6-(2,2,2-trifluoro-1-(3'-methylbiphenyl-4-yl)ethoxy)-1,3,5-triazin-2-yl)phenyl)propanoic acid | 524 | D (2.22) |
| (S)-2-amino-3-(4-(4-amino-6-((R)-1-(naphthalen-2-yl)ethylamino)pyrimidin-2-yl)phenyl)propanoic acid | 428 | A (2.90) |
| (S)-2-amino-3-(4-(2-amino-6-(benzylthio)pyrimidin-4-yl)phenyl)propanoic acid | 379 | E (1.66) |
| (2S)-2-amino-3-(4-(2-amino-6-(2,2,2-trifluoro-1-(4'-fluorobiphenyl-4-yl)ethoxy)pyrimidin-4-yl)phenyl)propanoic acid | 527 | E (2.07) |
| (2S)-2-amino-3-(4-(6-(3-(4-chlorophenoxy)piperidin-1-yl)pyrimidin-4-yl)phenyl)propanoic acid | 453 | A (2.67) |
| (S)-3-(4-(4-amino-6-((R)-1-(naphthalen-2-yl)ethylamino)-1,3,5-triazin-2-yl)phenyl)-2-(2-aminoacetamido)propanoic acid | 486 | J (2.83) |

-continued

| Compound | LCMS (M + 1) | HPLC Method (Time (min)) |
|---|---|---|
| (S)-2-amino-3-(4-(6-((R)-1-(naphthalen-2-yl)ethylamino)-2-(trifluoromethyl)pyrimidin-4-yl)phenyl)propanoic acid | 481 | A (3.70) |
| (S)-2-amino-3-(4-(2-amino-6-(4-(3-chlorophenyl)piperazin-1-yl)pyrimidin-4-yl)phenyl)propanoic acid | 453 | L (0.72) |
| (S)-2-amino-3-(4-(2-amino-6-((R)-2,2,2-trifluoro-1-phenylethoxy)pyrimidin-4-yl)phenyl)propanoic acid | 433 | E (1.77) |
| (2S)-2-amino-3-(4-(2-amino-6-(1,4-diphenylbutylamino)pyrimidin-4-yl)phenyl)propanoic acid | 482 | A (3.15) |
| (2S)-2-amino-3-(4-(6-(1-(3'-chlorobiphenyl-2-yl)-2,2,2-trifluoroethoxy)pyrimidin-4-yl)phenyl)propanoic acid | 528 | E (2.35) |
| (2S)-2-amino-3-(4-(4-amino-6-(1-(biphenyl-4-yl)-2,2,2-trifluoroethoxy)-1,3,5-triazin-2-yl)phenyl)propanoic acid | 510 | D (2.14) |
| (2S)-2-amino-3-(4-(2-amino-6-(2,2,3,3,3-pentafluoro-1-(3-fluoro-4-methylphenyl)propoxy)pyrimidin-4-yl)phenyl)propanoic acid | 515 | N (3.34) |
| (S)-ethyl 2-amino-3-(4-(2-amino-6-((R)-2,2,2-trifluoro-1-(3'-methoxybiphenyl-4-yl)ethoxy)pyrimidin-4-yl)phenyl)propanoate | 567 | N (2.17) |
| (S)-2-amino-3-(4-(2-amino-6-((S)-2,2,2-trifluoro-1-(3'-methoxybiphenyl-4-yl)ethoxy)pyrimidin-4-yl)phenyl)propanoic acid | 539 | N (3.36) |
| (2S)-2-amino-3-(4-(2-amino-6-(2,2,2-trifluoro-1-(3-fluoro-3'-methoxybiphenyl-4-yl)ethoxy)pyrimidin-4-yl)phenyl)propanoic acid | 557 | O (3.52) |
| (2S)-2-amino-3-(4-(2-amino-6-(1-(3'-(dimethylamino)biphenyl-2-yl)-2,2,2-trifluoroethoxy)pyrimidin-4-yl)phenyl)propanoic acid | 552 | Q (3.00) |
| (2S)-2-amino-3-(4-(2-amino-6-(2,2,2-trifluoro-1-(3'-methoxy-5-methylbiphenyl-2-yl)ethoxy)pyrimidin-4-yl)phenyl)propanoic acid | 553 | N (3.63) |
| (2S)-2-amino-3-(4-(2-amino-6-(2,2,2-trifluoro-1-(4'-methoxy-5-methylbiphenyl-2-yl)ethoxy)pyrimidin-4-yl)phenyl)propanoic acid | 553 | N (3.61) |
| (2S)-2-amino-3-(4-(2-amino-6-(2,2,2-trifluoro-1-(3'-methoxy-3-(methylsulfonyl)biphenyl-4-yl)ethoxy)pyrimidin-4-yl)phenyl)propanoic acid | 617 | O (3.28) |
| (2S)-2-amino-3-(4-(2-amino-6-(1-(2-(cyclopropylmethoxy)-4-fluorophenyl)-2,2,2-trifluoroethoxy)pyrimidin-4-yl)phenyl)propanoic acid | 521 | N (1.57) |
| (2S)-2-amino-3-(4-(6-(1-(2-(cyclopropylmethoxy)-4-fluorophenyl)-2,2,2-trifluoroethoxy)pyrimidin-4-yl)phenyl)propanoic acid | 507 | N (1.62) |
| (2S)-2-amino-3-(4-(2-amino-6-(2,2,2-trifluoro-1-(2-(isopentyloxy)phenyl)ethoxy)pyrimidin-4-yl)phenyl)propanoic acid | 520 | N (1.69) |
| (2S)-2-amino-3-(4-(5-(2,2,2-trifluoro-1-(3'-fluorobiphenyl-4-yl)ethoxy)pyrazin-2-yl)phenyl)propanoic acid | 512 | — |
| (2S)-2-amino-3-(4-(2-amino-6-(2,2,2-trifluoro-1-(4'-methoxybiphenyl-2-yl)ethoxy)pyrimidin-4-yl)phenyl)propanoic acid | 539 | N (3.50) |
| (2S)-2-amino-3-(4-(2-amino-6-(1-(3'-carbamoylbiphenyl-2-yl)-2,2,2-trifluoroethoxy)pyrimidin-4-yl)phenyl)propanoic acid | 552 | N (3.14) |
| (2S)-2-amino-3-(4-(2-amino-6-(1-(4'-carbamoylbiphenyl-2-yl)-2,2,2-trifluoroethoxy)pyrimidin-4-yl)phenyl)propanoic acid | 552 | N (3.05) |
| (2S)-2-amino-3-(4-(2-amino-6-(2,2,2-trifluoro-1-(4-(2-methoxyphenoxy)phenyl)ethoxy)pyrimidin-4-yl)phenyl)propanoic acid | 555 | N (1.55) |
| (2S)-2-amino-3-(4-(6-(2,2,2-trifluoro-1-(4-(2-methoxyphenoxy)phenyl)ethoxy)pyrimidin-4-yl)phenyl)propanoic acid | 541 | N (1.59) |
| (2S)-2-amino-3-(4-(6-(2,2,2-trifluoro-1-(2-(isopentyloxy)phenyl)ethoxy)pyrimidin-4-yl)phenyl)propanoic acid | 505 | N (1.74) |
| (2S)-3-(4-(6-(1-(3'-acetamidobiphenyl-2-yl)-2,2,2-trifluoroethoxy)-2-aminopyrimidin-4-yl)phenyl)-2-aminopropanoic acid | 566 | N (3.18) |
| (2S)-3-(4-(6-(1-(4'-acetamidobiphenyl-2-yl)-2,2,2-trifluoroethoxy)-2-aminopyrimidin-4-yl)phenyl)-2-aminopropanoic acid | 566 | N (3.23) |
| (2S)-2-amino-3-(4-(2-amino-6-(1-(4-cyanophenyl)-2,2,2-trifluoroethoxy)pyrimidin-4-yl)phenyl)propanoic acid | 458 | — |
| (S)-ethyl 2-amino-3-(4-(2-amino-6-((R)-2,2,2-trifluoro-1-p-tolylethoxy)pyrimidin-4-yl)phenyl)propanoate | 475 | — |
| (2S)-2-amino-3-(4-(2-amino-6-(2,2,2-trifluoro-1-(1-methoxybicyclo[2.2.2]oct-5-en-2-yl)ethoxy)pyrimidin-4-yl)phenyl)propanoic acid | 493 | O (2.97) |

-continued

| Compound | LCMS (M + 1) | HPLC Method (Time (min)) |
|---|---|---|
| (2S)-2-amino-3-(4-(2-amino-6-(1-(4-(cyclopentyloxy)phenyl)-2,2,2-trifluoroethoxy)pyrimidin-4-yl)phenyl)propanoic acid | 517 | N (1.61) |
| (2S)-2-amino-3-(4-(6-(1-(4-(cyclopentyloxy)phenyl)-2,2,2-trifluoroethoxy)pyrimidin-4-yl)phenyl)propanoic acid | 503 | N (1.67) |
| (2S)-2-amino-3-(4-(2-amino-6-(2,2,2-trifluoro-1-(4-(3-methoxyphenoxy)phenyl)ethoxy)pyrimidin-4-yl)phenyl)propanoic acid | 556 | N (1.59) |
| (2S)-2-amino-3-(4-(2-amino-6-(1-(4,5-dimethoxybiphenyl-2-yl)-2,2,2-trifluoroethoxy)pyrimidin-4-yl)phenyl)propanoic acid | 569 | S (3.34) |
| (2S)-2-amino-3-(4-(2-amino-6-(1-(4,5-dimethoxy-3'-methylbiphenyl-2-yl)-2,2,2-trifluoroethoxy)pyrimidin-4-yl)phenyl)propanoic acid | 583 | S (3.50) |
| (2S)-2-amino-3-(4-(5-(2,2,2-trifluoro-1-(2'-methylbiphenyl-2-yl)ethoxy)pyrazin-2-yl)phenyl)propanoic acid | 508 | — |
| (2S)-2-amino-3-(4-(6-(2,2,2-trifluoro-1-(4-(3-methoxyphenoxy)phenyl)ethoxy)pyrimidin-4-yl)phenyl)propanoic acid | 541 | N (1.64) |
| (2S)-2-amino-3-(4-(2-amino-6-(1-(2-(3,5-difluorophenoxy)phenyl)-2,2,2-trifluoroethoxy)pyrimidin-4-yl)phenyl)propanoic acid | 561 | N (1.64) |
| (2S)-2-amino-3-(4-(2-amino-6-(2,2,2-trifluoro-1-(4-(4-methoxyphenoxy)phenyl)ethoxy)pyrimidin-4-yl)phenyl)propanoic acid | 556 | N (1.58) |
| (2S)-2-amino-3-(4-(2-amino-6-(1-(4'-((S)-2-amino-2-carboxyethyl)biphenyl-2-yl)-2,2,2-trifluoroethoxy)pyrimidin-4-yl)phenyl)propanoic acid | 596 | — |
| (2S)-2-amino-3-(4-(2-amino-6-(1-(2-bromophenyl)-2,2,2-trifluoroethoxy)pyrimidin-4-yl)phenyl)propanoic acid | 513 | — |
| (2S)-2-amino-3-(4-(5-(2,2,2-trifluoro-1-(3'-methylbiphenyl-2-yl)ethoxy)pyrazin-2-yl)phenyl)propanoic acid | 508 | — |
| (2S)-2-amino-3-(4-(2-amino-6-(2,2,2-trifluoro-1-(4-methoxybiphenyl-2-yl)ethoxy)pyrimidin-4-yl)phenyl)propanoic acid | 539 | S (3.51) |
| (2S)-2-amino-3-(4-(5-(2,2,2-trifluoro-1-(2-(4-methylthiophen-3-yl)phenyl)ethoxy)pyrazin-2-yl)phenyl)propanoic acid | 514 | — |
| (2S)-2-amino-3-(4-(2-amino-6-(2,2,2-trifluoro-1-(4-methoxy-3'-methylbiphenyl-2-yl)ethoxy)pyrimidin-4-yl)phenyl)propanoic acid | 553 | S (3.66) |
| (2S)-2-amino-3-(4-(2-amino-6-(2,2,2-trifluoro-1-(3'-(hydroxymethyl)biphenyl-2-yl)ethoxy)pyrimidin-4-yl)phenyl)propanoic acid | 539 | — |
| (2S)-2-amino-3-(4-(2-amino-6-(1-(3'-cyanobiphenyl-2-yl)-2,2,2-trifluoroethoxy)pyrimidin-4-yl)phenyl)propanoic acid | 534 | — |
| (2S)-2-amino-3-(4-(6-(1-(2-(3,5-difluorophenoxy)phenyl)-2,2,2-trifluoroethoxy)pyrimidin-4-yl)phenyl)propanoic acid | 547 | N (1.69) |
| (2S)-2-amino-3-(4-(6-(2,2,2-trifluoro-1-(4-(4-methoxyphenoxy)phenyl)ethoxy)pyrimidin-4-yl)phenyl)propanoic acid | 541 | N (1.63) |
| (2S)-2-amino-3-(4-(2-amino-6-(2,2,2-trifluoro-1-(2-(4-methylthiazol-2-yl)thiophen-3-yl)ethoxy)pyrimidin-4-yl)phenyl)propanoic acid | 536 | — |
| (2S)-2-amino-3-(4-(2-amino-6-(2,2,2-trifluoro-1-(5-(4-methoxyphenyl)isoxazol-3-yl)ethoxy)pyrimidin-4-yl)phenyl)propanoic acid | 530 | O (3.14) |
| (2S)-2-amino-3-(4-(2-amino-6-(2,2,2-trifluoro-1-(1-phenyl-5-(trifluoromethyl)-1H-pyrazol-4-yl)ethoxy)pyrimidin-4-yl)phenyl)propanoic acid | 567 | O (3.24) |
| (2S)-2-amino-3-(4-(2-amino-6-(1-(2-(cyclohexyloxy)-4-methylphenyl)-2,2,2-trifluoroethoxy)pyrimidin-4-yl)phenyl)propanoic acid | 545 | N (1.76) |
| (2S)-2-amino-3-(4-(2-amino-6-(1-(2-(cyclopentyloxy)-4-methylphenyl)-2,2,2-trifluoroethoxy)pyrimidin-4-yl)phenyl)propanoic acid | 532 | N (1.71) |
| (2S)-2-amino-3-(4-(2-amino-6-(1-(benzo[d]thiazol-6-yl)-2,2,2-trifluoroethoxy)pyrimidin-4-yl)phenyl)propanoic acid | 490 | O (2.66) |
| (2S)-2-amino-3-(4-(2-amino-6-(2,2,2-trifluoro-1-(1-methyl-1H-imidazol-5-yl)ethoxy)pyrimidin-4-yl)phenyl)propanoic acid | 437 | — |
| (2S)-2-amino-3-(4-(6-(1-(2-(cyclopentyloxy)-4-methylphenyl)-2,2,2-trifluoroethoxy)pyrimidin-4-yl)phenyl)propanoic acid | 517 | N (1.78) |
| (2S)-2-amino-3-(4-(6-(1-(2-(cyclohexyloxy)-4-methylphenyl)-2,2,2-trifluoroethoxy)pyrimidin-4-yl)phenyl)propanoic acid | 531 | N (1.87) |
| (2S)-2-amino-3-(4-(2-amino-6-(2,2,2-trifluoro-1-(pyridin-3-yl)ethoxy)pyrimidin-4-yl)phenyl)propanoic acid | 434 | — |
| (2S)-2-amino-3-(4-(2-amino-6-(1-(1,3-dimethyl-1H-pyrazol-5-yl)-2,2,2-trifluoroethoxy)pyrimidin-4-yl)phenyl)propanoic acid | 451 | — |

-continued

| Compound | LCMS (M + 1) | HPLC Method (Time (min)) |
|---|---|---|
| (S)-2-amino-3-(4-(2-amino-6-(3-hydroxyphenyl)pyrimidin-4-yl)phenyl)propanoic acid | 351 | — |
| (2S)-2-amino-3-(4-(2-amino-6-(2,2,2-trifluoro-1-(3'-hydroxybiphenyl-2-yl)ethoxy)pyrimidin-4-yl)phenyl)propanoic acid | 526 | — |
| (S)-2-amino-3-(4-(2-amino-6-(3,5-difluorophenyl)pyrimidin-4-yl)phenyl)propanoic acid | 371 | — |
| (2S)-2-amino-3-(4-(2-amino-6-(1-(3',5'-difluorobiphenyl-2-yl)-2,2,2-trifluoroethoxy)pyrimidin-4-yl)phenyl)propanoic acid | 546 | — |
| (2S)-2-amino-3-(4-(6-(2,2,2-trifluoro-1-(3'-fluorobiphenyl-3-yl)ethoxy)pyrazin-2-yl)phenyl)propanoic acid | 512 | — |
| (2S)-2-amino-3-(4-(2-amino-6-(1-(5-ethoxy-2-methyl-2,3-dihydrobenzofuran-6-yl)-2,2,2-trifluoroethoxy)pyrimidin-4-yl)phenyl)propanoic acid | 533 | O (3.16) |
| (2S)-2-amino-3-(4-(2-amino-6-(1-(benzofuran-5-yl)-2,2,2-trifluoroethoxy)pyrimidin-4-yl)phenyl)propanoic acid | 473 | — |
| (2S)-2-amino-3-(4-(2-amino-6-(2,2,2-trifluoro-1-(2-m-tolylfuran-3-yl)ethoxy)pyrimidin-4-yl)phenyl)propanoic acid | 513 | — |
| (S)-ethyl 3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoate | 596 | N (3.55) |
| (2S)-2-amino-3-(4-(6-(2,2,2-trifluoro-1-(2-(4-methylthiophen-3-yl)phenyl)ethoxy)pyrazin-2-yl)phenyl)propanoic acid | 514 | — |
| (2S)-2-amino-3-(4-(2-amino-6-(2,2,2-trifluoro-1-(5-methyl-3-phenylisoxazol-4-yl)ethoxy)pyrimidin-4-yl)phenyl)propanoic acid | 514 | N (3.12) |
| (S)-2-amino-3-(4-(2-amino-6-(3-(methylthio)phenyl)pyrimidin-4-yl)phenyl)propanoic acid | 381 | — |
| (2S)-2-amino-3-(4-(2-amino-6-(2,2,2-trifluoro-1-(3'-(methylthio)biphenyl-2-yl)ethoxy)pyrimidin-4-yl)phenyl)propanoic acid | 555 | — |
| (2S)-2-amino-3-(4-(2-amino-6-(1-(3'-((dimethylamino)methyl)biphenyl-2-yl)-2,2,2-trifluoroethoxy)pyrimidin-4-yl)phenyl)propanoic acid | 566 | — |
| (S)-2-amino-3-(4-(2-amino-6-(3-(trifluoromethoxy)phenyl)pyrimidin-4-yl)phenyl)propanoic acid | 419 | — |
| (2S)-2-amino-3-(4-(2-amino-6-(2,2,2-trifluoro-1-(3'-(trifluoromethoxy)biphenyl-2-yl)ethoxy)pyrimidin-4-yl)phenyl)propanoic acid | 593 | — |
| (S)-3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoic acid | 596 | N (1.51) |
| (2S)-2-amino-3-(4-(2-amino-6-(2,2,2-trifluoro-1-(1-methyl-5-phenyl-1H-pyrazol-4-yl)ethoxy)pyrimidin-4-yl)phenyl)propanoic acid | 513 | N (2.88) |
| (2S)-2-amino-3-(4-(2-amino-6-(2,2,2-trifluoro-1-(4-(methylsulfonyl)phenyl)ethoxy)pyrimidin-4-yl)phenyl)propanoic acid | 511 | — |
| (S)-2-amino-3-(4-(2-amino-6-((R)-1-(3'-(dimethylamino)biphenyl-2-yl)-2,2,2-trifluoroethoxy)pyrimidin-4-yl)phenyl)propanoic acid | 552 | S (3.09) |
| (2S)-2-amino-3-(4-(2-amino-6-(1-(2-chloro-4-(methylsulfonyl)phenyl)-2,2,2-trifluoroethoxy)pyrimidin-4-yl)phenyl)propanoic acid | 545 | — |
| (2S)-2-amino-3-(4-(2-amino-6-(2,2,2-trifluoro-1-(3-(furan-2-yl)thiophen-2-yl)ethoxy)pyrimidin-4-yl)phenyl)propanoic acid | 505 | — |
| (2S)-2-amino-3-(4-(2-amino-6-(1-(2-(cyclopentyloxy)-4-fluorophenyl)-2,2,2-trifluoroethoxy)pyrimidin-4-yl)phenyl)propanoic acid | 543 | N (1.66) |
| (2S)-2-amino-3-(4-(2-amino-6-(2,2,2-trifluoro-1-(2-(3-methoxyphenyl)cyclohex-1-enyl)ethoxy)pyrimidin-4-yl)phenyl)propanoic acid | 543 | O (3.59) |
| (2S)-2-amino-3-(4-(2-amino-6-(2,2,2-trifluoro-1-(pyrimidin-5-yl)ethoxy)pyrimidin-4-yl)phenyl)propanoic acid | 435 | — |
| (2S)-2-amino-3-(4-(5-(2,2,2-trifluoro-1-(3'-methoxybiphenyl-3-yl)ethoxy)pyrazin-2-yl)phenyl)propanoic acid | 524 | — |
| (S)-2-amino-3-(4-(2-amino-6-((S)-1-(3'-(dimethylamino)biphenyl-2-yl)-2,2,2-trifluoroethoxy)pyrimidin-4-yl)phenyl)propanoic acid | 552 | N (3.08) |
| (2S)-2-amino-3-(4-(2-amino-6-(2,2,2-trifluoro-1-(2-(furan-2-carboxamido)phenyl)ethoxy)pyrimidin-4-yl)phenyl)propanoic acid | 542 | N (2.61) |
| (2S)-2-amino-3-(4-(2-amino-6-(1-(4-chloro-2-(methylsulfonyl)phenyl)-2,2,2-trifluoroethoxy)pyrimidin-4-yl)phenyl)propanoic acid | 545 | — |

| Compound | LCMS (M + 1) | HPLC Method (Time (min)) |
|---|---|---|
| (S)-isopropyl 2-amino-3-(4-(2-amino-6-((R)-2,2,2-trifluoro-1-(3'-methoxybiphenyl-4-yl)ethoxy)pyrimidin-4-yl)phenyl)propanoate | 581 | — |
| (2S)-2-amino-3-(4-(6-(1-(2-(cyclopentyloxy)-4-fluorophenyl)-2,2,2-trifluoroethoxy)pyrimidin-4-yl)phenyl)propanoic acid | 520 | N (1.73) |
| (2S)-2-amino-3-(4-(6-(1-(2-(cyclohexyloxy)-4-fluorophenyl)-2,2,2-trifluoroethoxy)pyrimidin-4-yl)phenyl)propanoic acid | 534 | N (1.81) |
| (2S)-2-amino-3-(4-(2-amino-6-(2,2,2-trifluoro-1-(1-(thiophen-2-yl)cyclohexyl)ethoxy)pyrimidin-4-yl)phenyl)propanoic acid | 521 | O (3.36) |
| (2S)-2-amino-3-(4-(2-(2,2,2-trifluoro-1-(3'-methoxybiphenyl-4-yl)ethoxy)thiazol-5-yl)phenyl)propanoic acid | 529 | Q (2.30) |
| (2S)-2-amino-3-(4-(2-amino-6-(1-(2-(cyclohexyloxy)-4-fluorophenyl)-2,2,2-trifluoroethoxy)pyrimidin-4-yl)phenyl)propanoic acid | 549 | N (1.70) |
| (2S)-2-amino-3-(4-(2-amino-6-(2,2,2-trifluoro-1-(1-(4-methoxyphenyl)cyclohexyl)ethoxy)pyrimidin-4-yl)phenyl)propanoic acid | 545 | O (3.41) |
| (2S)-2-amino-3-(4-(6-(2,2,2-trifluoro-1-(4-fluoro-2-methylphenyl)ethoxy)pyrimidin-4-yl)phenyl)propanoic acid | 450 | N (1.50) |
| (2S)-2-amino-3-(4-(2-amino-6-(2,2,2-trifluoro-1-(4-fluoro-2-methylphenyl)ethoxy)pyrimidin-4-yl)phenyl)propanoic acid | 465 | N (1.45) |
| (2S)-2-amino-3-(4-(2-amino-6-(oxazol-2-yl(phenyl)methoxy)pyrimidin-4-yl)phenyl)propanoic acid | 432 | O (1.76) |
| (S)-2-amino-3-(4-(2-amino-6-(1-cyclohexyl-2,2,2-trifluoroethylideneaminooxy)pyrimidin-4-yl)phenyl)propanoic acid | 452 | O (3.47) |
| (2S)-2-amino-3-(4-(2-amino-6-(1-(2-(3-(dimethylamino)phenyl)furan-3-yl)-2,2,2-trifluoroethoxy)pyrimidin-4-yl)phenyl)propanoic acid | 543 | N (3.02) |
| (2S)-2-amino-3-(4-(2-amino-6-(2,2,2-trifluoro-1-(5-phenylthiophen-2-yl)ethoxy)pyrimidin-4-yl)phenyl)propanoic acid | 515 | N (3.39) |
| (S)-phenyl 2-amino-3-(4-(2-amino-6-((R)-2,2,2-trifluoro-1-(3'-methoxybiphenyl-4-yl)ethoxy)pyrimidin-4-yl)phenyl)propanoate | 615 | Q (3.00) |
| (S)-2-amino-3-(4-(2-amino-6-((R)-1-(3'-((dimethylamino)methyl)biphenyl-4-yl)-2,2,2-trifluoroethoxy)pyrimidin-4-yl)phenyl)propanoic acid | 566 | N (2.60) |
| (S)-2-amino-3-(4-(1-(3-methoxybenzoyl)-1H-pyrazol-4-yl)phenyl)propanoic acid | 366 | O (2.55) |
| (2S)-2-amino-3-(4-(6-(2,2,2-trifluoro-1-(5-phenylfuran-2-yl)ethoxy)pyrimidin-4-yl)phenyl)propanoic acid | 484 | N (3.65) |
| (2S)-2-amino-3-(4-(2-amino-6-(1-(4-chloro-2-fluorophenyl)-2,2,2-trifluoroethoxy)pyrimidin-4-yl)phenyl)propanoic acid | 486 | N (3.14) |
| (S,E)-2-amino-3-(4-(2-amino-6-(4-(trifluoromethyl)styryl)pyrimidin-4-yl)phenyl)propanoic acid | 429 | N (2.94) |
| (2S)-2-amino-3-(4-(2-amino-6-(1-(3,4-dichlorophenyl)-2,2,2-trifluoroethoxy)pyrimidin-4-yl)phenyl)propanoic acid | 502 | N (3.31) |
| (2S)-2-amino-3-(4-(2-amino-6-(1-(4-chloro-3-fluorophenyl)-2,2,2-trifluoroethoxy)pyrimidin-4-yl)phenyl)propanoic acid | 486 | N (3.13) |
| (S)-2-amino-3-(4-(2-amino-6-((R)-1-(3'-(dimethylamino)biphenyl-4-yl)-2,2,2-trifluoroethoxy)pyrimidin-4-yl)phenyl)propanoic acid | 552 | N (2.66) |
| (2S)-2-amino-3-(4-(2-amino-6-(1-chloro-2,2,2-trifluoro-1-(4-methoxybiphenyl-2-yl)ethoxy)pyrimidin-4-yl)phenyl)propanoic acid | 573 | N (3.77) |
| (2S)-2-amino-3-(4-(6-(2,2,2-trifluoro-1-(5-phenylthiophen-2-yl)ethoxy)pyrimidin-4-yl)phenyl)propanoic acid | 500 | N (3.75) |
| (S)-2-amino-3-(4-(5-(4-phenoxyphenyl)-1H-1,2,3-triazol-1-yl)phenyl)propanoic acid | 401 | O (3.20) |
| (S,E)-2-amino-3-(4-(2-amino-6-(2-(biphenyl-4-yl)vinyl)pyrimidin-4-yl)phenyl)propanoic acid | 437 | N (3.17) |
| (S)-2-amino-3-(4-(4-amino-6-((R)-2,2,2-trifluoro-1-(3'-methoxybiphenyl-4-yl)ethoxy)pyrimidin-2-yl)phenyl)propanoic acid | 539 | — |
| (S)-2-amino-3-(4-(4'-methoxybiphenyl-4-ylsulfonamido)phenyl)propanoic acid | 428 | N (2.78) |
| (2S)-2-amino-3-(4-(2-amino-6-(2,2,2-trifluoro-1-(6-(3-methoxyphenyl)pyridin-3-yl)ethoxy)pyrimidin-4-yl)phenyl)propanoic acid | 540 | N (3.09) |
| (2S)-2-amino-3-(4-(2-amino-6-(2,2,2-trifluoro-1-(6-(2-fluoro-3-methoxyphenyl)pyridin-3-yl)ethoxy)pyrimidin-4-yl)phenyl)propanoic acid | 558 | N (3.00) |
| 2-amino-3-(5-(4'-methylbiphenyl-4-yl)-1H-indol-3-yl)propanoic acid | 371 | N (1.48) |

-continued

| Compound | LCMS (M + 1) | HPLC Method (Time (min)) |
|---|---|---|
| 2-amino-3-(5-m-tolyl-1H-indol-3-yl)propanoic acid | 295 | N (1.19) |
| (2S)-2-amino-3-(4-(2-(2-methoxyphenyl)furan-3-carboxamido)phenyl)propanoic acid | 358 | O (2.68) |
| 2-amino-3-(5-(1-benzyl-1H-pyrazol-4-yl)-1H-indol-3-yl)propanoic acid | 361 | N (1.10) |
| (2S)-2-amino-3-(4-(2-amino-6-(2,2,2-trifluoro-1-(6-(thiophen-2-yl)pyridin-3-yl)ethoxy)pyrimidin-4-yl)phenyl)propanoic acid | 516 | N (1.42) |
| 2-amino-3-(6-(1-benzyl-1H-pyrazol-4-yl)-1H-indol-3-yl)propanoic acid | 361 | N (1.09) |
| (S)-2-amino-3-(4-((2-(4-(trifluoromethyl)phenyl)thiazol-4-yl)methylamino)phenyl)propanoic acid | 422 | O (3.00) |
| (S)-2-amino-3-(4-((4'-methoxybiphenyl-4-ylsulfonamido)methyl)phenyl)propanoic acid | 441 | O (2.94) |
| (S)-2-amino-3-(4-(3-(2-methoxydibenzo[b,d]furan-3-yl)ureido)phenyl)propanoic acid | 420 | O (3.36) |
| (S)-2-amino-3-(4-(3-(2,2-diphenylethyl)ureido)phenyl)propanoic acid | 404 | O (2.97) |
| (S)-2-amino-3-(4-(phenylethynyl)phenyl)propanoic acid | 266 | N (2.91) |
| (S)-2-amino-3-(4-(2-amino-6-((5-(1-methyl-5-(trifluoromethyl)-1H-pyrazol-3-yl)thiophen-2-yl)methoxy)pyrimidin-4-yl)phenyl)propanoic acid | 410 | N (1.39) |
| (2S)-2-amino-3-(4-(2-amino-6-(1,1,1-trifluoro-3-((R)-2,2,3-trimethylcyclopent-3-enyl)propan-2-yloxy)pyrimidin-4-yl)phenyl)propanoic acid | 479 | O (3.42) |
| (2S)-2-amino-3-(4-(2-amino-6-(3-(2-hydroxyethylcarbamoyl)piperidin-1-yl)pyrimidin-4-yl)phenyl)propanoic acid | 429 | N (1.53) |
| (2S)-2-amino-3-(4-(2-amino-6-(3-(pyridin-2-yloxy)piperidin-1-yl)pyrimidin-4-yl)phenyl)propanoic acid | 435 | N (2.11) |
| (S)-2-amino-3-(4-(2-amino-6-(4-chloro-3-(piperidine-1-carbonyl)phenyl)pyrimidin-4-yl)phenyl)propanoic acid | 480 | N (2.75) |

6.55. In Vitro Inhibition Assays

Human TPH1, TPH2, tyrosine hydroxylase (TH) and phenylalanine hydroxylase (PH) were all generated using genes having the following accession numbers, respectively: X52836, AY098914, X05290, and U49897.

The full-length coding sequence of human TPH1 was cloned into the bacterial expression vector pET24 (Novagen, Madison, Wis., USA). A single colony of BL21(DE3) cells harboring the expression vector was inoculated into 50 ml of L broth (LB)-kanamycin media and grown up at 37° C. overnight with shaking. Half of the culture (25 ml) was then transferred into 3 L of media containing 1.5% yeast extract, 2% Bacto Peptone, 0.1 mM tryptophan, 0.1 mM ferrous ammonium sulfate, and 50 mM phosphate buffer (pH 7.0), and grown to $OD_{600}$=6 at 37° C. with oxygen supplemented at 40%, pH maintained at 7.0, and glucose added. Expression of TPH1 was induced with 15% D-lactose over a period of 10 hours at 25° C. The cells were spun down and washed once with phosphate buffered saline (PBS).

TPH1 was purified by affinity chromatography based on its binding to pterin. The cell pellet was resuspended in a lysis buffer (100 ml/20 g) containing 50 mM Tris-Cl, pH 7.6, 0.5 M NaCl, 0.1% Tween-20, 2 mM EDTA, 5 mM DTT, protease inhibitor mixture (Roche Applied Science, Indianapolis, Ind., USA) and 1 mM phenylmethanesulfonyl fluoride (PMSF), and the cells were lyzed with a microfluidizer. The lysate was centrifuged and the supernatant was loaded onto a pterin-coupled sepharose 4B column that was equilibrated with a buffer containing 50 mM Tris, pH 8.0, 2 M NaCl, 0.1% Tween-20, 0.5 mM EDTA, and 2 mM DTT. The column was washed with 50 ml of this buffer and TPH1 was eluded with a buffer containing 30 mM $NaHCO_3$, pH 10.5, 0.5 M NaCl, 0.1% Tween-20, 0.5 mM EDTA, 2 mM DTT, and 10% glycerol. Eluted enzyme was immediately neutralized with 200 mM $KH_2PO_4$, pH 7.0, 0.5 M NaCl, 20 mM DTT, 0.5 mM EDTA, and 10% glycerol, and stored at −80° C.

Human tryptophan hydroxylase type II (TPH2), tyrosine hydroxylase (TH) and phenylalanine hydroxylase (PAH) were expressed and purified essentially in the same way, except the cells were supplemented with tyrosine for TH and phenylalanine for PAH during growth.

TPH1 and TPH2 activities were measured in a reaction mixture containing 50 mM 4-morpholinepropanesulfonic acid (MOPS), pH 7.0, 60 µM tryptophan, 100 mM ammonium sulfate, 100 µM ferrous ammonium sulfate, 0.5 mM tris(2-carboxyethyl)phosphine (TCEP), 0.3 mM 6-methyl tetrahydropterin, 0.05 mg/ml catalase, and 0.9 mM DTT. The reactions were initiated by adding TPH1 to a final concentration of 7.5 nM. Initial velocity of the reactions was determined by following the change of fluorescence at 360 nm (excitation wavelength=300 nm). TPH1 and TPH2 inhibition was determined by measuring their activities at various compound concentrations, and the potency of a given compound was calculated using the equation:

$$v = b + \frac{v_0 - b}{1 + \left(\frac{[C]}{[I_{c50}]}\right)^D}$$

where v is the initial velocity at a given compound concentration C, v o is the v when C=0, b is the background signal, D is the Hill slope which is approximately equal to 1, and $I_{c50}$ is the concentration of the compound that inhibits half of the maximum enzyme activity.

Human TH and PAH activities were determined by measuring the amount of $^3H_2O$ generated using L-[3,4-$^3$H]-tyrosine and L-[4-$^3$H]-phenylalanine, respectively. The enzyme (100 nM) was first incubated with its substrate at 0.1 mM for about 10 minutes, and added to a reaction mixture containing 50 mM MOPS, pH 7.2, 100 mM ammonium sulfate, 0.05% Tween-20, 1.5 mM TCEP, 100 µM ferrous ammonium sulfate, 0.1 mM tyrosine or phenylalanine, 0.2 mM 6-methyl tetrahydropterin, 0.05 mg/ml of catalase, and 2 mM DTT. The reactions were allowed to proceed for 10-15 minutes and stopped by the addition of 2 M HCl. The mixtures were then filtered through activated charcoal and the radioactivity in the filtrate was determined by scintillation counting. Activities of compounds on TH and PAH were determined using this assay and calculated in the same way as on TPH1 and TPH2.

6.56. Cell-Based Inhibition Assays

Two types of cell lines were used for screening: RBL2H3 is a rat mastocytoma cell line, which contains TPH1 and makes 5-hydroxytrypotamine (5HT) spontaneously; BON is a human carcinoid cell line, which contains TPH1 and makes 5-hydroxytryptophan (5HTP). The CBAs were performed in 96-well plate format. The mobile phase used in HPLC contained 97% of 100 mM sodium acetate, pH 3.5 and 3% acetonitrile. A Waters C18 column (4.6×50 mm) was used with Waters HPLC (model 2795). A multi-channel fluorometer (model 2475) was used to monitor the flow through by setting at 280 nm as the excitation wavelength and 360 nm as the emission wavelength.

RBL CBA: Cells were grown in complete media (containing 5% bovine serum) for 3-4 hours to allow cells to attach to plate wells (7K cell/well). Compounds were then added to each well in the concentration range of 0.016 µM to 11.36 µM. The controls were cells in complete media without any compound present. Cells were harvested after 3 days of incubation at 37° C. Cells were >95% confluent without compound present. Media were removed from plate and cells were lysed with equal volume of 0.1 N NaOH. A large portion of the cell lysate was treated by mixing with equal volume of 1M TCA and then filtered through glass fiber. The filtrates were loaded on reverse phase HPLC for analyzing 5HT concentrations. A small portion of the cell lysate was also taken to measure protein concentration of the cells that reflects the cytotoxicity of the compounds at the concentration used. The protein concentration was measured by using BCA method.

The average of 5HT level in cells without compound treated was used as the maximum value in the $IC_{50}$ derivation according to the equation provided above. The minimum value of 5HT is either set at 0 or from cells that treated with the highest concentration of compound If a compound is not cytotoxic at that concentration.

BON CBA: Cells were grown in equal volume of DMEM and F12K with 5% bovine serum for 3-4 hours (20K cell/well) and compound was added at a concentration range of 0.07 µM to 50 µM. The cells were incubated at 37° C. overnight. Fifty µM of the culture supernatant was then taken for 5HTP measurement. The supernatant was mixed with equal volume of 1M TCA, then filtered through glass fiber. The filtrate was loaded on reverse phase HPLC for 5HTP concentration measurement. The cell viability was measured by treating the remaining cells with Promega Celltiter-Glo Luminescent Cell Viability Assay. The compound potency was then calculated in the same way as in the RBL CBA.

6.57. In Vivo Effects

The in vivo effects of a potent TPH1 inhibitor of the invention were evaluated in several studies by determining the change of 5-HT levels in the intestines and brains of mice following oral administration of the compound.

The compound was formulated in different vehicles to provide either a suspension or solution. Generally, 14-week-old male C57 albino mice were dosed once daily by oral gavage at 5 ml/kg for four consecutive days. Five hours after the last dose, the animals were quickly sacrificed. Various regions of the intestinal tract and whole brain were taken and frozen immediately. 5-HT was extracted from the tissues and measured by HPLC. Blood samples were taken for exposure analysis.

The potent TPH1 inhibitor was found to reduce 5-HT levels in both the small and large intestine, but not in the brain. In one study, the compound was formulated in $H_2O$ and administered to mice at four different dose levels: 15, 50, 150, and 500 mg/kg, once daily by oral gavage. As shown in FIG. 1, the compound caused significant reduction of 5-HT in the jejunum and ileum in a dose-dependent fashion. In the colon, statistically significant reduction of 5-HT was seen at the 50, 150, and 500 mg/kg/day dose levels. No significant change of 5-HT levels was observed in the brain at any of the dose levels.

All publications (e.g., patents and patent applications) cited above are incorporated herein by reference in their entireties.

What is claimed is:
1. A method of treating pulmonary hypertension, which comprises administering to a patient in need thereof therapeutically effective amounts of an endothelin receptor antagonist and a compound of the formula:

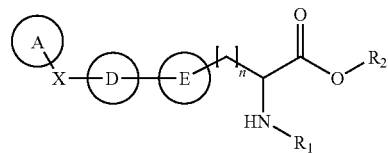

or a pharmaceutically acceptable salt thereof, wherein:
A is optionally substituted cycloalkyl, aryl, or heterocycle;
X is a bond, —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$), —C($R_3R_4$)S($O_2$)—, or —S($O_2$)C($R_3R_4$)—;
D is optionally substituted aryl or heterocycle;
E is optionally substituted aryl or heterocycle;
$R_1$ is hydrogen or optionally substituted alkyl, alkyl-aryl, alkyl-heterocycle, aryl, or heterocycle;
$R_2$ is hydrogen or optionally substituted alkyl, alkyl-aryl, alkyl-heterocycle, aryl, or heterocycle;
$R_3$ is hydrogen, alkoxy, amino, cyano, halogen, hydroxyl, or optionally substituted alkyl;
$R_4$ is hydrogen, alkoxy, amino, cyano, halogen, hydroxyl, or optionally substituted alkyl or aryl;
$R_5$ is hydrogen or optionally substituted alkyl or aryl; and
n is 0-3.
2. The method of claim 1, wherein the compound is of the formula:

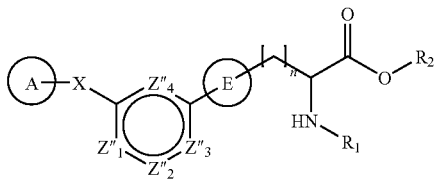

wherein:
each of $Z''_1$, $Z''_2$, $Z''_3$, and $Z''_4$ is independently N or $CR_{10}$;
each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle;
each $R_{11}$ is independently hydrogen or optionally substituted alkyl, alkyl-aryl or alkyl-heterocycle;
each $R_{12}$ is independently hydrogen or optionally substituted alkyl, alkyl-aryl or alkyl-heterocycle; and
each $R_{13}$ is independently hydrogen or optionally substituted alkyl, alkyl-aryl or alkyl-heterocycle.

3. The method of claim 2, wherein the compound is of the formula:

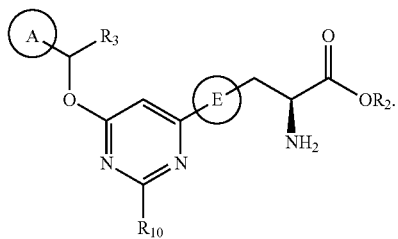

4. The method of claim 3, wherein A is optionally substituted biphenyl.

5. The method of claim 3, wherein $R_3$ is trifluoromethyl.

6. The method of claim 3, wherein E is optionally substituted phenyl.

7. The method of claim 3, wherein $R_{10}$ is amino.

8. The method of claim 1, wherein the endothelin receptor antagonist is ambrisentan, BMS-193884, bosentan, darusentan, SB-234551, sitaxsentan, or tezosentan.

9. The method of claim 8, wherein the endothelin receptor antagonist is bosentan.

10. A method of treating pulmonary hypertension, which comprises administering to a patient in need thereof therapeutically effective amounts of an endothelin receptor antagonist and a compound of the formula:

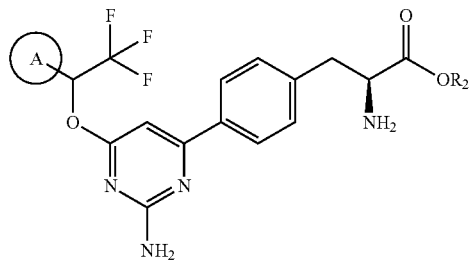

or a pharmaceutically acceptable salt thereof, wherein A is optionally substituted cycloalkyl, aryl, or heterocycle; and $R_2$ is hydrogen or lower alkyl.

11. The method of claim 10, wherein A is optionally substituted biphenyl.

12. The method of claim 10, wherein the endothelin receptor antagonist is ambrisentan, BMS-193884, bosentan, darusentan, SB-234551, sitaxsentan, or tezosentan.

13. The method of claim 12, wherein the endothelin receptor antagonist is bosentan.

14. A method of treating pulmonary hypertension, which comprises administering to a patient in need thereof therapeutically effective amounts of an endothelin receptor antagonist and (S)-2-amino-3-(4-(2-amino-6-((R)-2,2,2-trifluoro-1-(3'-methoxybiphenyl-4-yl)ethoxy)pyrimidin-4-yl)phenyl)propanoic acid, or a pharmaceutically acceptable salt thereof.

15. The method of claim 14, wherein the endothelin receptor antagonist is ambrisentan, BMS-193884, bosentan, darusentan, SB-234551, sitaxsentan, or tezosentan.

16. The method of claim 15, wherein the endothelin receptor antagonist is bosentan.

* * * * *